US008766040B2

(12) United States Patent
Patel et al.

(10) Patent No.: US 8,766,040 B2

(45) Date of Patent: Jul. 1, 2014

(54) ***BRASSICA OGURA* RESTORER LINES WITH SHORTENED *RAPHANUS* FRAGMENT (SRF)**

(71) Applicant: Pioneer Hi Bred International Inc, Johnston, IA (US)

(72) Inventors: Jayantilal Patel, Thornhill (CA); Lomas Tulsieram, Mississauga (CA); Yongping Zhang, Branpton (CA)

(73) Assignee: Pioneer Hi-Bred International, Inc., Johnston, IA (US)

( * ) Notice: Subject to any disclaimer, the term of this patent is extended or adjusted under 35 U.S.C. 154(b) by 0 days.

(21) Appl. No.: 13/904,135

(22) Filed: May 29, 2013

(65) Prior Publication Data

US 2013/0254946 A1 Sep. 26, 2013

Related U.S. Application Data

(62) Division of application No. 12/366,155, filed on Feb. 5, 2009, now Pat. No. 8,466,347.

(60) Provisional application No. 61/054,857, filed on May 21, 2008, provisional application No. 61/026,604, filed on Feb. 6, 2008.

(51) Int. Cl.

| | |
|---|---|
| ***A01H 1/04*** | (2006.01) |
| ***A01H 1/02*** | (2006.01) |
| ***A01H 5/00*** | (2006.01) |
| ***A01H 5/10*** | (2006.01) |
| ***C12N 5/04*** | (2006.01) |

(52) U.S. Cl.

USPC ............ 800/306; 800/267; 800/274; 435/410

(58) Field of Classification Search

None

See application file for complete search history.

(56) References Cited

U.S. PATENT DOCUMENTS

| | | | |
|---|---|---|---|
| 5,789,566 | A | 8/1998 | Bonhomme et al. |
| 5,973,233 | A | 10/1999 | Burns et al. |
| 6,229,072 | B1 | 5/2001 | Burns et al. |
| 6,392,127 | B1 | 5/2002 | Charne et al. |
| 7,071,375 | B2 | 7/2006 | Brown et al. |
| 7,314,971 | B2 | 1/2008 | Brown et al. |
| 2007/0256150 | A1 | 11/2007 | Primard-Breisset et al. |
| 2007/0294792 | A1 | 12/2007 | Pleines et al. |

FOREIGN PATENT DOCUMENTS

| | | | |
|---|---|---|---|
| EP | 1 493 328 | A1 | 1/2005 |
| WO | 9702737 | A1 | 1/1997 |
| WO | 9856948 | A1 | 12/1998 |
| WO | 0054574 | A2 | 9/2000 |

OTHER PUBLICATIONS

Hong, et al.; AFLP and SCAR markers linked to the suppressor gene (Rf) of a dominant genetic male sterility in rapeseed (*Brassica napus* L.); Euphytica (2006) 151:401-409; Kluwer Academic Press; Amsterdam, Netherlands.

Delourme, et al.; "Identification of RAPD markers linked to a fertility restorer gene for the Ogura radish cytoplasmic male sterility of rapeseed (*Brassica napus* L.)"; Thoretical and Applied Genetics (1994) 88(6/7):741-748; Springer; Berlin, Germany.

Y. Shen et al., Database EMBL (Online) Feb. 2, 2006, Strongly *Locentrotus purpuratus* clone R-3-3024G19, Working Draft Sequence, 16 unordered pieces, XP002543896, Database Accession No. AC180800, Nucleotides 9096-9076.

Primard-Brisset, C., et al.; "A new recombined double low restorer line for the Ogu-INRA cms in rapeseed (*Brassica napus* L.)"; Theor Appl Genet (2005) 111:736-746; Springer-Verlag; Berlin/Heidelberg, Germany.

*Primary Examiner* — David T Fox

(57) ABSTRACT

New *Brassica Ogura* fertility restorer lines with a shortened *Raphanus* fragment are provided. The new lines lack the OPC2 marker and are capable of fully restoring fertility in *Ogura* cytoplasmic male sterile (cms) plants. The improved lines were developed using a new breeding method. The new breeding method can be used to shorten an exotic insertion comprising a gene of interest in any plant.

6 Claims, 5 Drawing Sheets

Fig. 1 *Raphanus* Fragment Reduction in SRF Lines

(Marker distance is not scaled genetically)

Fig. 3 Crossing Chart for SRF Development
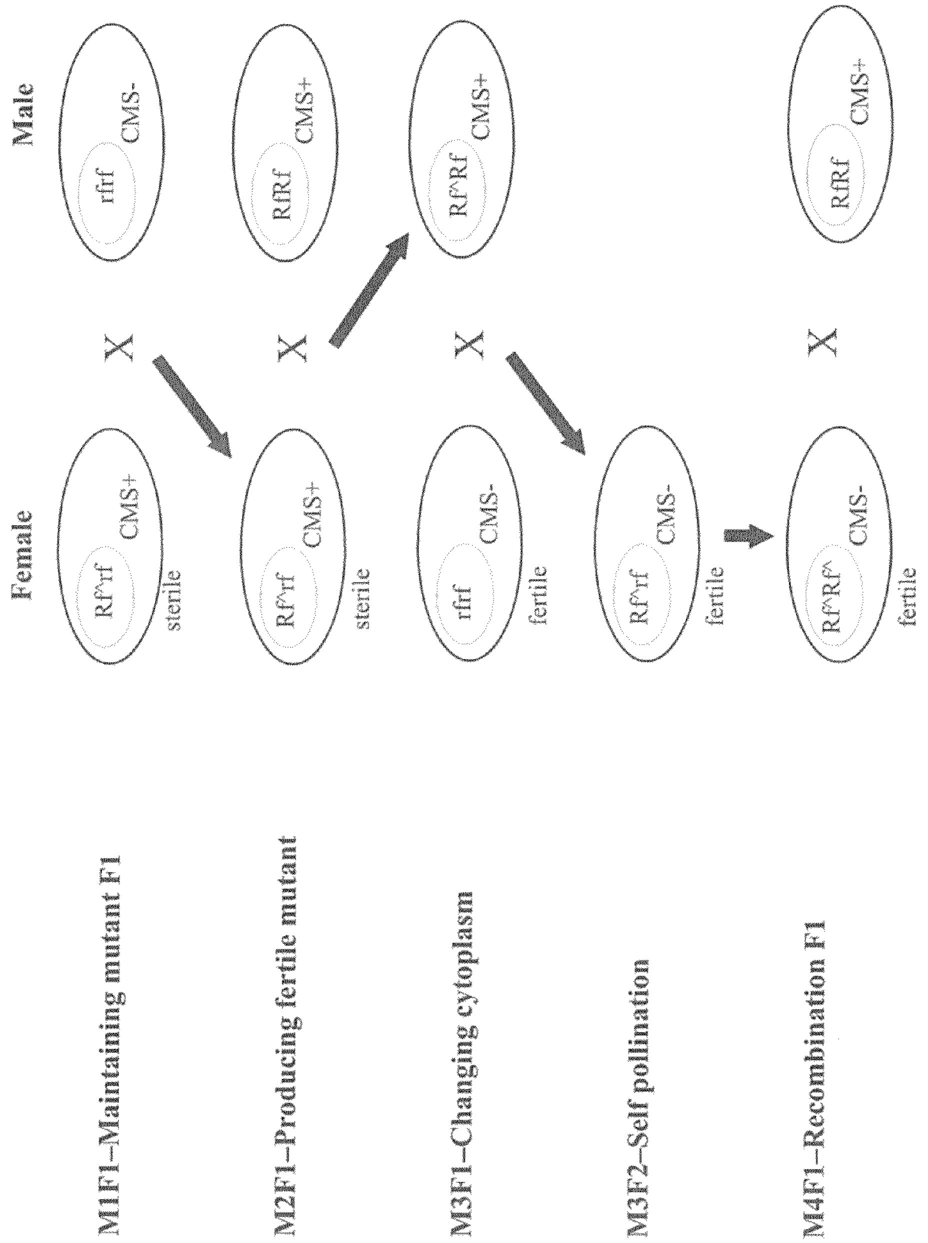

Fig. 3 Continue...
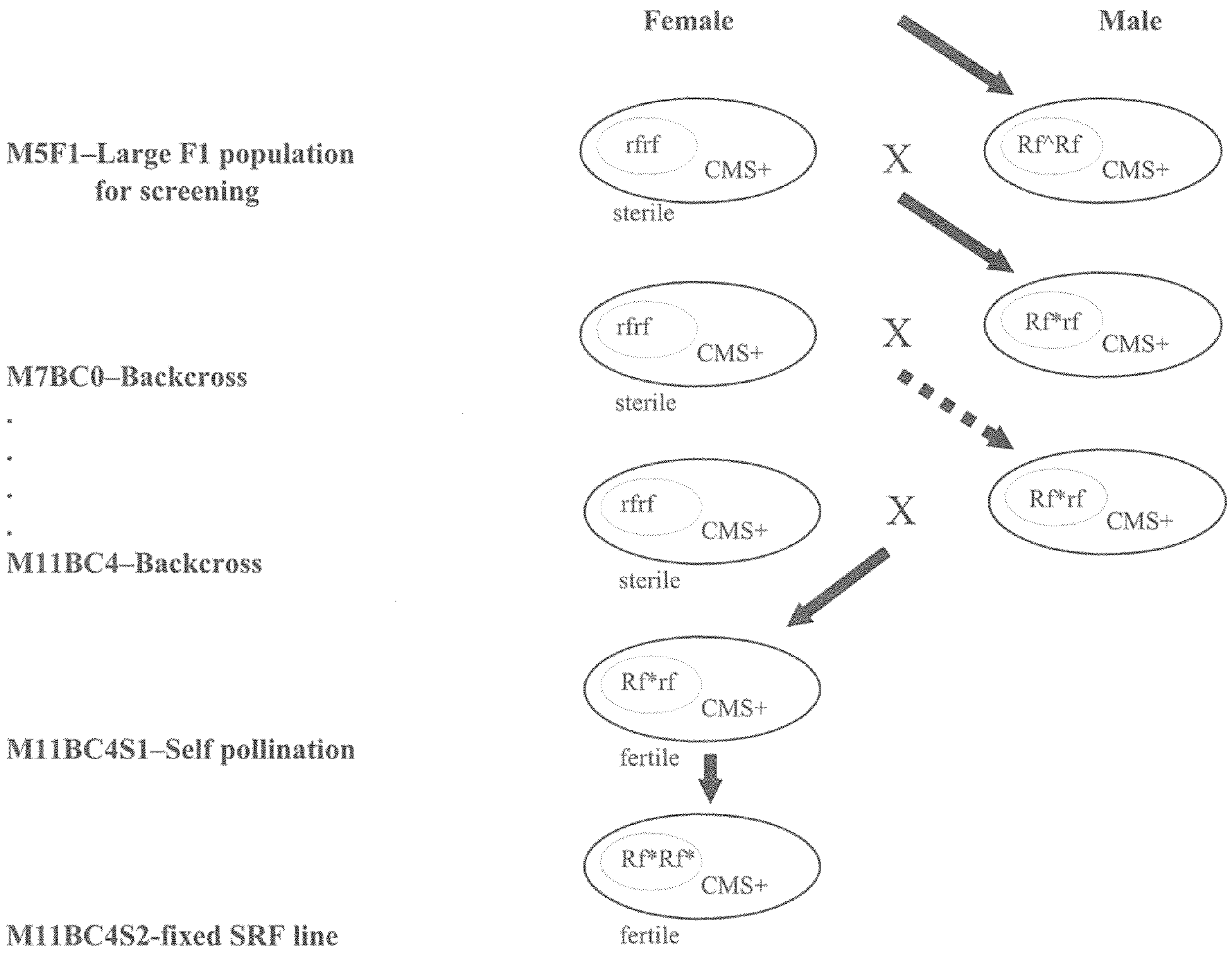

Fig. 4 Method for Shortening an Exotic Insertion
(cartoon)
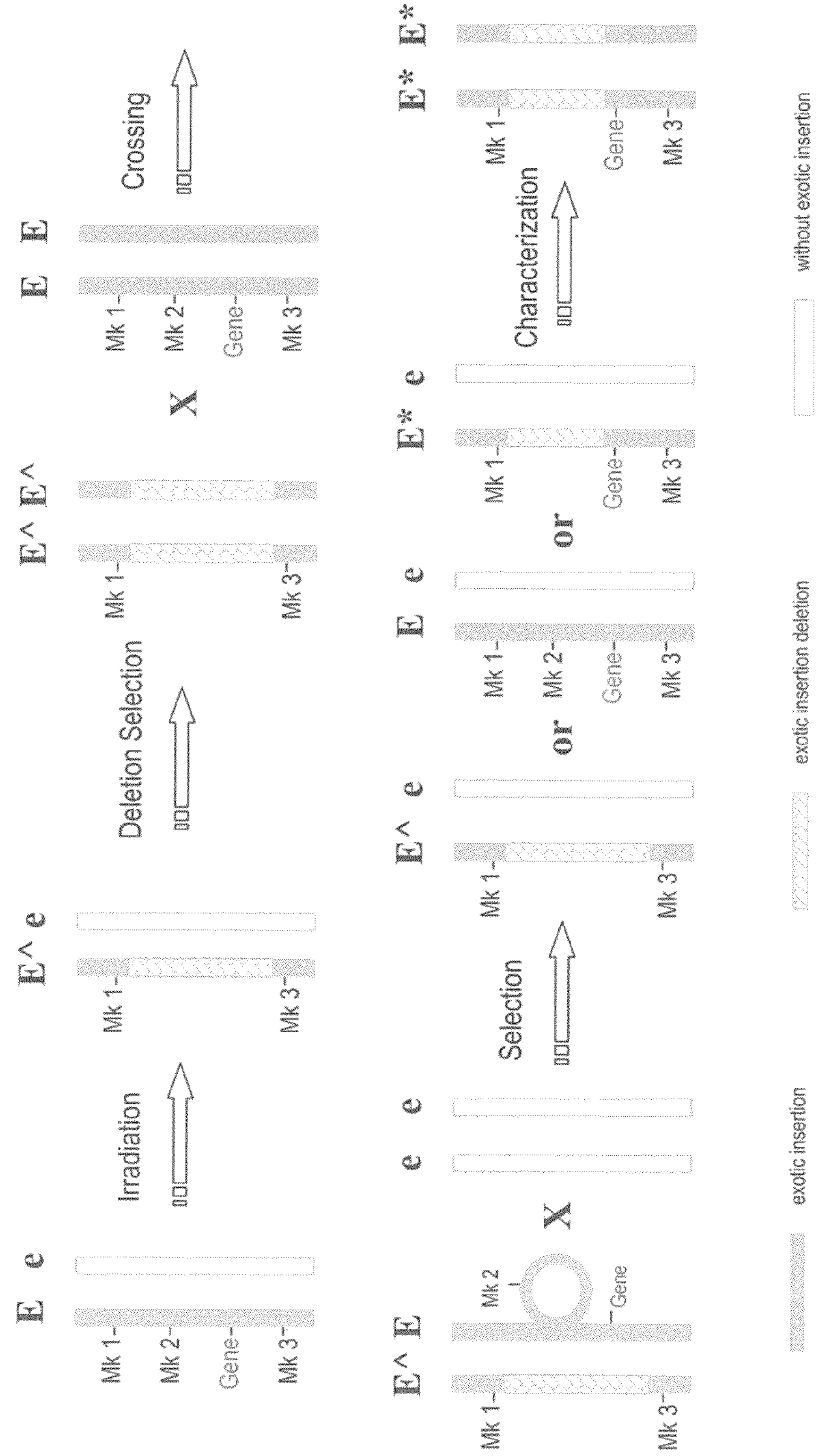

SEQUENCE LISTING

<160> NUMBER OF SEQ ID NOS: 237

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
gcttctactt ccataccaat gg 22

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 2
caagctcttc ggtatgaaac g 21

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 3
aagcttcagc ttatccttgg 20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 4
gttcgttgta gatcggatcc 20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 5
cttgctgcaa agcacttctc 20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 6
agcttcagac caagtcccag 20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 7
ggatcacgaa actcccaagg 20

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 8
tcatatctcc ctccttgtcc a 21

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 9
aagctcaggc tccttcaccg 20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gggaaggaga tccggactca                                                  20

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
aagcttatag agtagccatt gag                                              23

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tctaagatca gtatatggac agc                                              23

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cggactcttt agctccgcca                                                  20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cacctcctgt cggcatctca                                                  20

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tattctgctt catgtggtga tc                                               22

<210> SEQ ID NO 16
<211> LENGTH: 22
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 16
acgattgtta agttgacgaa ag 22

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tttttcaatg cttctgtgca g 21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gcacaaaatt acaatcagcg c 21

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
aagctttgtg ttgctaatgt at 22

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
agttgaaacg atataacttg tga 23

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
attgtcgttg tcgatgcatc 20

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 22
agaagaagaa agtgccaagc a 21

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 23
aaaattgcga ggttcaggaa t 21

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 24
ctccagctcc tgttagtgac tctt 24

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 25
aatttatggg gtgtcaattg a 21

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 26
tggctgattt gcaacataaa 20

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 27
gttctggcta tgtcgagacc ac 22

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 28
ccagagtttg gaggcagact 20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 29
gagttgtggg tttggccgtc 20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 30
acgcaccaga acgatcaatc 20

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 31
atcagagcaa aagagtgcgt ag 22

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 32
cgaaataccg aagaaccaaa tc 22

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 33
acatcggtcg aagaagttcc 20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 34
aatcttgagg caagcctgac 20

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 35
agcttctatt cagccaaaag g 21

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 36
gcattaccgt tggaaaattt c 21

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 37
accaaagaca ccataacgag g 21

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 38
cgcactttta gcagcagttc 20

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 39
cccactcttg ttaccttcag c 21

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 40
gttcccacag cctaccagta c 21

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 41
attggatttg aatgagatgg 20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 42
tccattgatc tctgcacatc 20

<210> SEQ ID NO 43
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 43
aactttttgt gtttgatttc ttgc 24

<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 44
actccttcta aacaaaacca aaca 24

<210> SEQ ID NO 45
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 45
aagcttgtct cctacgtact tc 22

<210> SEQ ID NO 46
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 46
tcagaaagat atttcacgtc ac 22

<210> SEQ ID NO 47
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 47
tggactaaga aagggtcagg ta 22

<210> SEQ ID NO 48
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 48
cgaagaatct ctactctgtt gt 22

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 49
aggaagtgag aggcagttgg 20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 50
tccatgggtg tcctaggatc 20

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 51
tgcgtaacac ttctttgctt c 21

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 52
tgcagaactc aaagccattc 20

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 53
aagcttattt tcatcctgca a 21

<210> SEQ ID NO 54
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 54
catcaccatc atcacagtaa tt 22

<210> SEQ ID NO 55
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 55
tccatagaag aaactctttg caac 24

<210> SEQ ID NO 56
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 56
tcgacacact tactaatctg agagtg 26

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 57
tattttgtcc tcggttagat c 21

<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 58
ttcctttgtg tttggttagg g 21

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 59
tgcgagttta atccggacgc 20

<210> SEQ ID NO 60
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 60
ccgcgttatt ctggttcaga ga 22

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 61
ttcctcggca agaacaacgc 20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 62
gccgtctaac agcaggtgca 20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 63
ccgtatttga aaacgtggcg 20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 64
tcaaccgtga atttgggtcg 20

```
<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65

gaggcgaaaa cataaacaag g                                               21


<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66

atcgccaaaa ctgtttcagg                                                 20


<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67

tcggtttttc gagggtatca                                                 20


<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68

tccgatttag aatcgaacct g                                               21


<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69

tcctgcagtt tgaaatcctt g                                               21


<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70

aagtttcccc aaaccaactt c                                               21


<210> SEQ ID NO 71
```

<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 71
aagcttaata gcgacttctt c 21

<210> SEQ ID NO 72
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 72
tgaaaaccct agtctctctc tc 22

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 73
aatggatgaa ctcgagacgg 20

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 74
tgataacccc tcgtttcctg 20

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 75
tgtcagcatt cagcagaagc 20

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 76
agggattgaa agctgggaac 20

<210> SEQ ID NO 77
<211> LENGTH: 22

<212> TYPE: DNA
<213> ORGANISM: Artificial Sequence
<220> FEATURE:
<223> OTHER INFORMATION: Description of Artificial Sequence: Synthetic
primer

<400> SEQUENCE: 77
ttgacggtta cccaaaatac cg 22

<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 78
ttgattgctt caccctcacc c 21

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 79
aaagcatcct ttgcaagggg 20

<210> SEQ ID NO 80
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 80
gaaccaaaaa tgagtggatg g 21

<210> SEQ ID NO 81
<211> LENGTH: 25
<212> TYPE: DNA
<213> ORGANISM: Artificial Sequence
<220> FEATURE:
<223> OTHER INFORMATION: Description of Artificial Sequence: Synthetic
primer

<400> SEQUENCE: 81
aaattgttac aaagtatgag aaatg 25

<210> SEQ ID NO 82
<211> LENGTH: 25
<212> TYPE: DNA
<213> ORGANISM: Artificial Sequence
<220> FEATURE:
<223> OTHER INFORMATION: Description of Artificial Sequence: Synthetic
primer

<400> SEQUENCE: 82
ttcagtaaac attttactca ttctc 25

<210> SEQ ID NO 83
<211> LENGTH: 22
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 83

tttccacaca aatcggattt aa                                              22


<210> SEQ ID NO 84
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84

tggccaatga aagtttactg at                                              22


<210> SEQ ID NO 85
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85

accaaaccga gaacaaaata ggtg                                            24


<210> SEQ ID NO 86
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86

ggttcgaata ctttggtttt ttgg                                            24


<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87

tggaggtgtc aaagtgtggc                                                 20


<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88

cgcaagtcac tttatttggc                                                 20


<210> SEQ ID NO 89
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 89

gaaccacgac tttgggtctg                                                   20


<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90

gctttggtta gaatgtcggc                                                   20


<210> SEQ ID NO 91
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91

gagaatattg gaagaaagcg g                                                 21


<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92

aagtcgtggt tcctttgagg                                                   20


<210> SEQ ID NO 93
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93

gctctacgag tgaggatcaa ag                                                22


<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94

cactttcgga atccaagctc                                                   20


<210> SEQ ID NO 95
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 95

agcttatagg cttctagacc c                                              21


<210> SEQ ID NO 96
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96

gtttctgttt ctgcaggctc                                                20


<210> SEQ ID NO 97
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97

agctttaatt catgtatttt taca                                           24


<210> SEQ ID NO 98
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98

aatttttttg tgatacattt caa                                            23


<210> SEQ ID NO 99
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99

ctgtaacttt caacccaact cgtagaa                                        27


<210> SEQ ID NO 100
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100

ttttggggat tactcttctt agctttc                                        27


<210> SEQ ID NO 101
<211> LENGTH: 21
<212> TYPE: DNA
<213> ORGANISM: Artificial Sequence
<220> FEATURE:
<223> OTHER INFORMATION: Description of Artificial Sequence: Synthetic
```

primer

<400> SEQUENCE: 101
aagcttgatc aaagatcaca g 21

<210> SEQ ID NO 102
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 102
aacaaactaa tgagcaacag g 21

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 103
cagaccgttc aagttcatgg 20

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 104
caagttgctc ggcatatgat 20

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 105
ccttctccaa accggtaaac 20

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 106
ttttgagaaa tgacggatcg 20

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 107
agaccaagag gaagcgtagc 20

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 108
aagaaacaac ccagactccg 20

<210> SEQ ID NO 109
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 109
caatgattta tacttcgttt ttgc 24

<210> SEQ ID NO 110
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 110
gcagcgtacg gtatgtctat ct 22

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 111
catttggttt gtccgtgtgt 20

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 112
aggcgacaac ctctttcaac 20

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 113
cattttcttt aacaacgcgc 20

<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 114
acgacggcga catgtagtac 20

<210> SEQ ID NO 115
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 115
tctctcacac tttctctcac 20

<210> SEQ ID NO 116
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 116
cgccgagaat ttccgcgcc 19

<210> SEQ ID NO 117
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 117
caaatcaata ccattaaaag tgg 23

<210> SEQ ID NO 118
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 118
tttttgatta atttcctttc aca 23

<210> SEQ ID NO 119
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 119
aatagaggga gaggatgaaa gaac 24

<210> SEQ ID NO 120
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 120
agctacctaa caggttttgt tataaag 27

<210> SEQ ID NO 121
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 121
tcacattagt aaaacgattg tccac 25

<210> SEQ ID NO 122
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 122
gattgatttt ttggactccg tt 22

<210> SEQ ID NO 123
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 123
ccttagttta gttgtaggtg gtgg 24

<210> SEQ ID NO 124
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 124
agaaaccgct caattttaac ataa 24

<210> SEQ ID NO 125
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 125
ccttggctat gtgcttatgt attt 24

<210> SEQ ID NO 126
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 126
taaaacacag agacaatcgt gagg 24

<210> SEQ ID NO 127
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 127
cattgataca tgaatgcaaa gaag 24

<210> SEQ ID NO 128
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 128
gatgaaaaca tttacagaca atgc 24

<210> SEQ ID NO 129
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 129
ctgcataaaa ttatcgaaga cagata 26

<210> SEQ ID NO 130
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 130
ttctgtttca gcgctaacaa atc 23

<210> SEQ ID NO 131
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 131
ctttgtcatt gtgtgtgtgt gtgt 24

<210> SEQ ID NO 132
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 132
aatatgattt ccaatttgcc aagt 24

<210> SEQ ID NO 133
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 133
aattcttgct ccattatgat ttca 24

<210> SEQ ID NO 134
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 134
cacaagacga tcaggaaaaa gaa 23

<210> SEQ ID NO 135
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 135
tccactccta gttcacaatc tatttt 26

<210> SEQ ID NO 136
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 136
tatacaaaat gttggaatac acaagg 26

<210> SEQ ID NO 137
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 137
cagaacacag ttctatgaca ctg 23

<210> SEQ ID NO 138
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 138
tataggagct ttgttctgta gtgg 24

<210> SEQ ID NO 139
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 139
tccattgcag aattcacctg 20

<210> SEQ ID NO 140
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 140
tgttttcttc gtcatgtcgg 20

<210> SEQ ID NO 141
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 141
cttgagggaa ggagacgaga 20

<210> SEQ ID NO 142
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 142
attttgggtc atgggttttt 20

<210> SEQ ID NO 143
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 143
atatccttaa acccttgcgc 20

<210> SEQ ID NO 144
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144
ttgaatacct ccaaggaccc 20

<210> SEQ ID NO 145
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
ggtctcaggt tttgtgggag 20

<210> SEQ ID NO 146
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
ggttctcaaa gattccgagg 20

<210> SEQ ID NO 147
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147
cttggtcaca cccatcttct c 21

<210> SEQ ID NO 148
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148
tgtccgataa actctctgcg 20

<210> SEQ ID NO 149
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
atcaaccacg ttcatccatg 20

<210> SEQ ID NO 150

-continued

<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 150
aactcaaata ctctcggcca g 21

<210> SEQ ID NO 151
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 151
atttaccaaa tggatcactc tgg 23

<210> SEQ ID NO 152
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 152
ccgagaattg aacattgtaa aga 23

<210> SEQ ID NO 153
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 153
caattccaca acgtagcaga g 21

<210> SEQ ID NO 154
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 154
cttttcgact aagaaccggc 20

<210> SEQ ID NO 155
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 155
agcttggact atgccgtttg 20

<210> SEQ ID NO 156
<211> LENGTH: 20

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 156

atttcaggac cggctatgtg                                                   20


<210> SEQ ID NO 157
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 157

tcgagaatcc tctacaaacg c                                                 21


<210> SEQ ID NO 158
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158

aagcaccact tattcgacag c                                                 21


<210> SEQ ID NO 159
<211> LENGTH: 247
<212> TYPE: DNA
<213> ORGANISM: Brassica napus

<400> SEQUENCE: 159

gcttctactt ccataccaat ggacattatc gcatagctgg ctatattctt ggagtcagct       60

gggagaaggt tagttccttg gtcttcgtat cggtgagcta tgtactgagt aatggctctt      120

gattctacac aaaaaaaaaa caaatcatgt tagtgaaatt ttcttcttat gcgtatttgt      180

tcaattcagg tttgagattg aagatgagat aatgattgct tataaacgtt tcataccgaa      240

gagcttg                                                                247


<210> SEQ ID NO 160
<211> LENGTH: 198
<212> TYPE: DNA
<213> ORGANISM: Brassica napus

<400> SEQUENCE: 160

aagcttcagc ttatccttgg cctagaagca acgtcaataa ctttccaacc gtgccttggt       60

tttacgatcg ggaagatgat ctggaaagct gacaacgaga tctttctatt gacatctcgc      120

tcgttttctg gttccttcta gatcaacggg aaaacactga tgaagttgac ttatcggcgg      180

atccgatcta caacgaac                                                    198


<210> SEQ ID NO 161
<211> LENGTH: 233
<212> TYPE: DNA
<213> ORGANISM: Brassica napus

<400> SEQUENCE: 161

cttgctgcaa agcacttctc tcatccactc ttagttcaac ttctgcttca agctttagta       60
```

-continued

```
ttgtttgctt taaacttgag acatcctctt gcaaactctt cactgatgct accgaggaga    120

gactgagctc actgagacct ttgttctcaa ccttggcttg ctgaatctcc tcatgcagct    180

cgttgtttcg gaactctcca tgtcattcat gatctgggac ttggtctgaa gct           233


<210> SEQ ID NO 162
<211> LENGTH: 348
<212> TYPE: DNA
<213> ORGANISM: Brassica napus

<400> SEQUENCE: 162

ggatcacgaa actcccaagg aaacttataa gtattttagg taagaccggt gtcaagaaga     60

acctgaggac tatcttttct tgagaagaag tatcagcttt catcaggatg aatctttcac    120

cggtagagat agtctaagag agacacaaga aagaacttcc tattcccttc ttcctttcaa    180

aaaaaaaact caggaaaaga gctgaagagg aagaccacta aaacacaagt agtaaggctg    240

acatatttaa ggctagacag aaacgtaaca gaaaggaaaa taagactcaa gaacatgaaa    300

gtagacaaag ggttgaaaga aaagatatgg acaaggaggg agatatga                 348


<210> SEQ ID NO 163
<211> LENGTH: 581
<212> TYPE: DNA
<213> ORGANISM: Brassica napus

<400> SEQUENCE: 163

aagctcaggc tccttcaccg cttcttctac atcaatgttc ttcccctttg atttgctacg     60

ttcttcccca gaagaagcac taatctcaga ttcttcatca ctgctctcat cagaatcact    120

gtacctcctc ttcctcctat gacctctcct cttcctacta cttccgcttt tcttcttctt    180

attccttctt ctacgcctcc tatcttcctc atccgaatca tcactctcgc tctcctcttc    240

cgattcgcta tcactccttc tcctacgctt actcctagac ctcttactct tcctcttctt    300

cctagatcta tcagattcag atcccgactt acccgaatca gattcgcctt tccgttgttt    360

cggatcgtca acatccttct ccggaaccac ctcctcgtca gcggcgttct catcggactc    420

ttcctcgtcg ggatctctgg gcggactcgg ccgtgttctc ccatatgcag tactttccag    480

atttcctcat ccttgaggcg tttaagccct cctgtactcc tcgtgacctc aattcctttc    540

aacctctttc gttccggagt ctgagtccgg atctccttcc c                        581


<210> SEQ ID NO 164
<211> LENGTH: 249
<212> TYPE: DNA
<213> ORGANISM: Brassica napus

<400> SEQUENCE: 164

aagcttatag agtagccatt gagtcgcctc tgattaactt tttgaaaagc caagtgtgaa     60

ctttttcctc cttcgtttcc caaaaaaaaa ccacttttct ttgataacat tctcttggat    120

ccaagcaacc caaactgaat cagttttgga agaataacat ccacatgagc ttgagcattc    180

aagatttgtt tcatacatgg atgttccggc tagtgataaa tattttgctg tccatatact    240

gatcttaga                                                            249


<210> SEQ ID NO 165
<211> LENGTH: 329
<212> TYPE: DNA
<213> ORGANISM: Brassica napus
```

<400> SEQUENCE: 165
cggactcttt agctccgcca taacaaccac agcagcctcc ggtgtgaaaa aactccactt 60
tttcacaaca acccaccgtc caagatccct ctccttcacc agaaccgcaa tccgcgccga 120
gaaaacagat tccgccgccg ccgccccagc ccccgccgtg aaagaagctc cggtgggatt 180
cacgccgcct cagctagacc caaacacacc gtcaccgatc ttcgcgggga gcaccggtgg 240
gcttctccgc aaagcccagg tggaagagat ctacgttatt acatggaact cgccgaaaga 300
acagatcttt gagatgccga caggaggtg 329

<210> SEQ ID NO 166
<211> LENGTH: 354
<212> TYPE: DNA
<213> ORGANISM: Brassica napus

<400> SEQUENCE: 166
tattctgctt catgtggtga tcatctccaa actcacatag ccaaaatatt gtttcaaaaa 60
gttcgataac cttatcaata tcgatccact ccagtggtct tttaataatg taatcaatgg 120
atagtcaatt cgtgaatcta ttgattcttg tatatatgga tatgtgaaag gagaacaaat 180
taaatcatgt acaagtcaaa cattggagta gtattagcct ccatttteta tagatatgaa 240 tgctccggaa aacaacttct tgttcaagat gaaatcagta catgaacatc gtacatatat 300
cgagtagatt ctctatgatg taagttcatt ttctttcgtc aacttaacaa tcgt 354

<210> SEQ ID NO 167
<211> LENGTH: 357
<212> TYPE: DNA
<213> ORGANISM: Brassica napus

<400> SEQUENCE: 167
tttttcaatg cttctgtgca gaatacccta attctcagga aattcaacat ggtctacctc 60
taatacattg gcaacaggtt caaggagatg atgctcctca ggtgattttt aaattatatt 120
tctcttttta aaggcagtta tttattataa ttattttctt gtcaataata ttcaccaaag 180
atatcctcac taatacattc actcttcctt ttaccttgat ttatacgttt tcccctggaa 240
tctatactta atattccatc aaaaatagtt attgtatgtt tactttgaaa ggtaccaaaa 300
ccacatattt aatttcaatc gttattatga ttatatgcgc tgattgtaat tttgtgc 357

<210> SEQ ID NO 168
<211> LENGTH: 208
<212> TYPE: DNA
<213> ORGANISM: Brassica napus

<400> SEQUENCE: 168
aagctttgtg ttgctaatgt atatattaac atcttgtcaa actactcatc ataattatat 60
atgctacaac ccgggctaca actaatgaaa tttgatcaac tgatcatcat ttttggtaaa 120
gttatacaaa atattatttc gctgataaat ttttcagtct ttcaaaaatg tggtttttat 180
ttttatcaca agttatatcg tttcaact 208

<210> SEQ ID NO 169
<211> LENGTH: 572
<212> TYPE: DNA
<213> ORGANISM: Brassica napus

<400> SEQUENCE: 169
attgtcgttg tcgatgcatc ctccagctgc tcttcaggcc atgttgttga tgatcctttc 60

```
atcggggaga aacagctgtc cattttccct atcttcttgt ccaaatctgt gatgcagtcg    120

ctcaggctgt tcctgtttgc ctgcctcagc caaggtatag ctacagacgc attctgcgag    180

ataaaactct cgcacgactt gattcttttc ggctttccgg aagacggctt cttgctaggt    240

aactgagagt tattattcca cacatgaatc cccgagtctt ctgttgttga cacgatgtgt    300

ttaccgtcca aagtaaacga ggcacgtgtt gtgcagacgc cagaagctgc aaaaaaggaa    360

gttagccaaa aggttataca tcttaattct taagtagaac aaaaaaaaat aaggcactaa    420

ttgtctctaa tactaacctt taagcttgca gatgacatca tcaccagata tgatacgaat    480

ctgtgaatca gcacaggtaa ccattacttt gtcggagtca ttgggaaaat actcaagacc    540

agtgatcctt ttgcttggca ctttcttctt ct                                  572
```

<210> SEQ ID NO 170
<211> LENGTH: 215
<212> TYPE: DNA
<213> ORGANISM: Brassica napus

<400> SEQUENCE: 170

```
aaaattgcga ggttcaggaa tgctgtttac agcgttgatg aagacttgat aggggtccga     60

aagggcatca taggacaagt agttagacat aggatgttca gtacaagagt tcactgagtc    120

acagtgataa tctcgcaggt agcttggagc cttatgaact ctgcgtgtag aagtgtctgg    180

aggtctgctt gaagagtcac taacaggagc tggag                               215
```

<210> SEQ ID NO 171
<211> LENGTH: 301
<212> TYPE: DNA
<213> ORGANISM: Brassica napus

<400> SEQUENCE: 171

```
aatttatggg gtgtcaattg aaccccctaa actgcatgta ggtccgccac gggatggaaa     60

tgaaactagt aaaataataa caattttaaa gatgctgata atagtaaata accaattaat    120

ttgcataata aaaataatta ccatcaggac gagcatatag taaatcatga cagggtccat    180

gacatagtta catatgcatc tttaaaaact actagaacaa tagtcgatga aattggaaat    240

attgaaaaac ctaacttgaa tgcaaaatga ttttataaag ttttatgttg caaatcagcc    300

a                                                                    301
```

<210> SEQ ID NO 172
<211> LENGTH: 459
<212> TYPE: DNA
<213> ORGANISM: Brassica napus

<400> SEQUENCE: 172

```
gttctggcta tgtcgagacc actgaaccac catgcctcat gtctgaatcg tgagctcgac     60

ttcttcttct tcttcgtggg tttcgtcatc atcaactcgc aaccgccgtg aacatgctca    120

ttcttaatct acgattctca gccgtgtgtg ctatgaaact cacattgagc tcctaatctc    180

caccgtaatc ctcctttctg ttaccatgat cttagacgta atcaaaacga tgtagaaccg    240

gtggcgtcat tctctgacac agatccaatt caacaagatc tcaccggaat ccatggtcat    300

gacaagctca acatcgtcgt ccagaatcaa gccttgtcgt ctcagctcac ctttggtcgg    360

attgaaatct cgatcgaaca ctaacaatgg tcatctttag cttatttgca tctgggtccc    420

tcaaatttca gttattttca gtctgcctcc aaactctgg                           459
```

<210> SEQ ID NO 173
<211> LENGTH: 168
<212> TYPE: DNA
<213> ORGANISM: Brassica napus

<400> SEQUENCE: 173

| gagttgtggg tttggccgtc tctgctggga ttagcacccc tggaatgtgt gcgagtcttg | 60 |
| cgtattttga tacgtatagg cgtgcgagat tgccggcgaa tctggttcag gcgcagagag | 120 |
| atctctttgg agctcatact tacgagagga ttgatcgttc tggtgcgt | 168 |

<210> SEQ ID NO 174
<211> LENGTH: 325
<212> TYPE: DNA
<213> ORGANISM: Brassica napus

<400> SEQUENCE: 174

| atcagagcaa aagagtgcgt agatgggttt tgagttttga aggaggaaac attggtttct | 60 |
| ccatgcattt tgaagtttga gtgaggataa tgttttctgt tttagttcgg ctcggataaa | 120 |
| aattgtgacc gctttttttt gttgttgttt tgatttggaa tctatttttt tgatgttttg | 180 |
| gtctgcccat ccatatctag attatatagt tagattatat agttggatag gaaaagtttt | 240 |
| tttttttggg tcaacaggat aggaaaagtc tatccagtga aagtggtgtt caatctaaat | 300 |
| attgatttgg ttcttcggta tttcg | 325 |

<210> SEQ ID NO 175
<211> LENGTH: 504
<212> TYPE: DNA
<213> ORGANISM: Brassica napus

<400> SEQUENCE: 175

| acatcggtcg aagaagttcc tgcatcaatt agtacgtgga gttatctttt gtctctttct | 60 |
| ataagaggca ctggaaatct caagaccata acacagctcc accaaagcct atatatgctg | 120 |
| gacttaagct acacagatat tgagaagatt ccagagtgca acaatggcct tgacggggtg | 180 |
| gaataccttt atctagctgg ctgtagaaga ctcacatcat tgccagagct ccctggttcg | 240 |
| ctcatatccc tattggcaga aaattgtgaa tcactggaga ccgtttcttc cccgttgaac | 300 |
| actccaaagg cacacctcaa tttcaccaac tgcttcaaac tggaccaaca aacaagaaga | 360 |
| gccattatgc aaccacgacc gtctctctac aggctggcaa tcttaccagg aagggaaata | 420 |
| cctgcagagt ttgatcaccg aggtcatgag accaccattg gtccttttc tgcatcctcc | 480 |
| aggtgtcagg cttgcctcaa gatt | 504 |

<210> SEQ ID NO 176
<211> LENGTH: 537
<212> TYPE: DNA
<213> ORGANISM: Brassica napus

<400> SEQUENCE: 176

| agcttctatt cagccaaaag gttttgattt tgaccaattt agagattttg tattggattc | 60 |
| agttgtactt gtgcacaaaa agaagtattg gaatcagtta gggttctagc ttttgcaaag | 120 |
| aactttattt ttcttgtatc agcttcgata atgtagatca aactgaataa atgttaaaca | 180 |
| aaataattat tcaaagcaaa tacaattatg cagaacaaat gcacattata tgtttatcaa | 240 |
| acaatttact aaatatcata tatattaaat gttaaactca ttatttaagg ctagcacaaa | 300 |
| atttgtacgt ggaaatttat gcatgatatt cttaaaattc atgtccctgg caatgagcaa | 360 |

aacattttct attcccatga ggattttcat gagtatgtgg atgtgtatat gtacgtccgc 420
gacatctgta tttttcataa cgttttctga aaaacaaaga aaaagaaaga ttaacacaat 480
tgaaaaacta aaaagtcaac ttgaaaatac taaaatgaaa ttttccaacg gtaatgc 537

<210> SEQ ID NO 177
<211> LENGTH: 524
<212> TYPE: DNA
<213> ORGANISM: Brassica napus

<400> SEQUENCE: 177
accaaagaca ccataacgag ggccatggga aaaggcaccg gcacggttgg ctagatcgtg 60
actggttacc ttagcaagat acgagttatc acccgtggca tagtagagcc acgctccccc 120
ccatatgagg tcatcccagt gatctgcgct tttccgcttg gcgctcatag cctcggcgta 180
aaggtaaacg gctttggcac tgttaacaag tgttgcagag tactcgactt ggtcacggaa 240
tacgatcgag gctgaggcca gggaagctgc catctctgca gcgagatgcg ggcagtctgt 300
gtaacataga ttgacagacc tttggtaatc aatgtcttct ggtcgcatcc agcagtatag 360
gtcactagtc acttggcttc cttgattcat tcctatctgt gaaaagaaaa acaaaaaaag 420
tttaggactg aaccgaattg agtatgcaag aaggaaggga aacaaaactt ttatacctga 480
tacaccattt catagatcgt atcagaactg ctgctaaaag tgcg 524

<210> SEQ ID NO 178
<211> LENGTH: 316
<212> TYPE: DNA
<213> ORGANISM: Brassica napus

<400> SEQUENCE: 178
cccactcttg ttaccttcag caccctgctc cacggattat gtgtggatgt aagtttgaga 60
acttgcttat ctttattcat cttgcgtaca aggtatataa cagagttctt gttacaacag 120
atttctacag actcctatat tacaggaaga taatatattt acaaaacaga tatgagaata 180
tccggagtat attctttcac cctcccgcag tgagaacgtc ggagtctctg acgtttaagc 240
tggttctgaa cgatcggaag agggaagttg gcaaaccttt tgtgaatata tcagcgtact 300
ggtaggctgt gggaac 316

<210> SEQ ID NO 179
<211> LENGTH: 358
<212> TYPE: DNA
<213> ORGANISM: Brassica napus

<400> SEQUENCE: 179
attggatttg aatgagatgg aagatttggt gtcggaaaat ggtataaaca aaaagatttg 60
ttatgcagaa aatcccaatg aagctatgtc caagaagagc tggagatgca acagctgttt 120
atgcttcaac tgagagagct gagaaagaac tcaaatggaa gtaagtcatt ggctttatca 180
tttttccgca tatagatcat acaatcttgc ttgtgaatca agatacaata atatgttcac 240
tctttgctac atagaagatt tttactgttg gcatgaataa aggactgatt ctttgtgatt 300
tttgttttgt ttattagggc acaatatgga gtggatgaga tgtgcagaga tcaatgga 358

<210> SEQ ID NO 180
<211> LENGTH: 496
<212> TYPE: DNA
<213> ORGANISM: Brassica napus

<400> SEQUENCE: 180
aactttttgt gtttgatttc ttgcagattt ggttcggtgg catatcttca gcaaatctgg 60
tggtttcaag tggatggaga aatcgatttc ccgttcccag ctggaaccta cagcgtcttc 120
ttcaggcttc acctaggcaa accgggaaag cggtttgggt tgggaaggtt tgcaacactg 180
aacagattca cggttgggaa cattaaaccg gttcgggttt cagatttgga ctgaagatgg 240
tcaacactct tcgtctcaat gcatgttaac cggatcggga agctggaatc actaccatgc 300
tggagacttg tgggttggaa atcccaaaag ctcgtcgatg actaagctta agttcctcca 360
tgacgcagat cgattgtaca catacccaag ggagggttgt gtgtggattc tgtgattgtg 420
tatccgagct cgtgtaagga ccggttgagg cgggtttaag tgtctaaacc gatgtttggt 480
tttgtttaga aggagt 496

<210> SEQ ID NO 181
<211> LENGTH: 317
<212> TYPE: DNA
<213> ORGANISM: Brassica napus

<400> SEQUENCE: 181
aagcttgtct cctacgtact tcttctatgt tcaaccgata atgtccttgt cagttttctt 60
gtatatttga ttttacagtt gttctgaaga ttttttattt ttgggttctt tattgctctg 120
aagctaaatt atcttttgtc gttctaatct ttgtcatata agctccatca aagtcttgtc 180
actcatgtat cactctccac atagaaagag aaacacgaga attgatgttt tttttaatcg 240
acgaattgga tgttttaaaa aaaaaaaatt ctcttttttc ttttttgaaa atttagtgac 300
gtgaaatatc tttctga 317

<210> SEQ ID NO 182
<211> LENGTH: 321
<212> TYPE: DNA
<213> ORGANISM: Brassica napus

<400> SEQUENCE: 182
tggactaaga aagggtcagg taatggttgt ggttctacca aacgtggccg agtatgggat 60
tattgccctt ggcattatgt ccgccggtgg agttttctcc ggcgctaatc ctacggctct 120
tgtctcggag atcaagaagc aagttgaagc ttctggtgct agaggaatca tcactgattc 180
tactaacttc gaaaaggtta agaatttggg tctaccggta atattgttag gtgaagagaa 240
gatcgaagga gcagtgaact ggaaagatat tctagaagca ggagataaat gtggagataa 300
caacagagta gagattcttc g 321

<210> SEQ ID NO 183
<211> LENGTH: 356
<212> TYPE: DNA
<213> ORGANISM: Brassica napus

<400> SEQUENCE: 183
aggaagtgag aggcagttgg cctcgtcacg ggttttagag tttagaaagc gtgtgcttga 60
aagtgttcag cagcgcgcat aggatcattg tgacaggggg agagtagctc gacctgtcct 120
tgggtagatt aggaattggt tcgtatcaag ttcagttgaa cgttgtgtaa ttcgaattag 180
acaagtcaag tgtgattgtc taagagattc ttaataaaac aagttgtgtg tttgagtatt 240
gatcgagttc cataaggaat cggtgtccac ttggttttac atttggtatc agagcgggtc 300
acctctgtgg actcacagag tctactcaca ggttgagatc ctaggacacc catgga 356

<210> SEQ ID NO 184
<211> LENGTH: 479
<212> TYPE: DNA
<213> ORGANISM: Brassica napus

<400> SEQUENCE: 184
tgcgtaacac ttctttgctt cactcgtgaa cagctccact cctggaacta acattctccc 60
tctttttatc tcaatgtgac ttccctgcta cctgcaacag aaacacacta gaacacacat 120
tctgacaggc aacacgatta tgatagtcag caaatcaagg agaacacccc aagagattat 180
ccttaaattt catcatgaaa actaggatat tacagccgat agaaaaagag ttcacaggtt 240
catgataatt caaataaaca ccgaaacaag gattaaacat ctgagcaaca acacattcat 300
tagtcgttgt cttggtttgc cgaggctgag gtgccaccga tgtctccata atctccccct 360
gcagtgaagc acaatgagat aaaaaaacga aaagaagtta gcaagatcaa gagttaccaa 420
gaaacctccc cagagaaacc ttactcttga gccgaatgtg aatggctttg agttctgca 479

<210> SEQ ID NO 185
<211> LENGTH: 266
<212> TYPE: DNA
<213> ORGANISM: Brassica napus

<400> SEQUENCE: 185
aagcttattt tcatcctgca atgtcaacaa catacataaa tctactcagc ttctctatac 60
acataacaca agaaagtaaa cacatatagg cataaggcat ggttgtttta aaaagatatt 120
tataagtata tacttacgtc ttcaaaatga aatatcattt atacttaaat cacgtttaaa 180
tacactattt ttactctttc aaacaaatat actatagttt acataaacac aaatttaact 240
atataattac tgtgatgatg gtgatg 266

<210> SEQ ID NO 186
<211> LENGTH: 116
<212> TYPE: DNA
<213> ORGANISM: Brassica napus
<220> FEATURE:
<221> NAME/KEY: modified_base
<222> LOCATION: (39)..(39)
<223> OTHER INFORMATION: a, c, g, t, unknown or other

<400> SEQUENCE: 186
tccatagaag aaactctttg caactatttt cctttgaana atgaaatcaa tcgtctcttc 60
cacaatttgc agaaacgtaa aatctattta cactctcaga ttagtaagtg tgtcga 116

<210> SEQ ID NO 187
<211> LENGTH: 213
<212> TYPE: DNA
<213> ORGANISM: Brassica napus

<400> SEQUENCE: 187
tattttgtcc tcggttagat cttctgttgt acattctgat gctcagagtg agagtcacac 60
atacattttc agtttctagg ttttgtctgt gattctgcaa gtgatgaagt tattggtttg 120
gtgttgagct ttttattatg tgtgtgtctc tgtcttcacg ttttgatgta tctgctgttc 180 gttttttaa aaccctaacc aaacacaaag gaa 213

<210> SEQ ID NO 188
<211> LENGTH: 500
<212> TYPE: DNA

<213> ORGANISM: Brassica napus

<400> SEQUENCE: 188
tgcgagttta atccggacgc caaagacctg acgaagctcg ccaagaacat agatttcgcg 60
tgcactttct cggactgtac cgcgctcggt tacgggtctt cttgcaatgg tctggatgcg 120
aacgggaacg cttcgtatgc gtttaacatg tattttcagg tgaagaacca ggatgagatg 180
gcttgtgtgt tccaaggttt ggccagagtt acagataaga atatatctca gggacagtgt 240
gagttccctg ttcagattgt tgcttcttcg tcttcttctt cttctgtgtc tctttttgtt 300
tggttgatca tcgctggagt tttgtttgtc ttgatgtttt gaggtccctt attgattata 360
tatatttcta ttttggtcta tgtgataata tgttggattt gggttaatcg tacaagacaa 420
agacaaaaac aaaacattgt tgaaataagt ctagcatgta agtcggttaa tttggttatc 480
tctgaaccag aataacgcgg 500

<210> SEQ ID NO 189
<211> LENGTH: 482
<212> TYPE: DNA
<213> ORGANISM: Brassica napus

<400> SEQUENCE: 189
ttcctcggca agaacaacgc accgatcacg atcaacatct accctttctt gagcctctac 60
ggtaacgacg acttcccgct caactacgcc ttcttcgacg gtgctcaacc gatagacgac 120
cacggtgtta gctacacgaa cgtcttcgac gccaacttcg acactttggt gtcgtctctg 180
aaagctgttg gtcatggaga tatgccgatt atagtaggag aagttggctg gccaacagag 240
ggtgacaaac acgctaacac cggtaacata tctctgaaac taacatagtg ctcaggccgt 300
ctcgaattat ttatggacca tgttaaaaaa atattaatga tatatttaat atataataga 360
atagttttaa aaatttatag ttttatatta taacttatat atttatttta aaaattctta 420
atttttcttt tgtttttcaa cttggatcat gttagttccg tttgcacctg ctgttagacg 480
gc 482

<210> SEQ ID NO 190
<211> LENGTH: 466
<212> TYPE: DNA
<213> ORGANISM: Brassica napus

<400> SEQUENCE: 190
ccgtatttga aaacgtggcg atctataaga tattttgtat gcgtcttccc gtcttccgaa 60
ttaatcatat agcatttttg tatggaacag ggaatataca tgaaggataa gttctgagca 120
tcattttttt aagactgatt catagaacta gtgatgttgt gttacttgtc gcttctcttg 180
gtgctcacga ctttgcatgt atggctttct tttgatctga tgtttatatc tgctttaggt 240
tttacttgga gacccaaggg caggatccaa tcagccagag atgcagagct ctattgtctt 300
ccatgcagga tacgttgatt ttgtgagtat tcctttactt gtatgggttt ttactctcac 360
gttgtcttta cgcatgattt caatattaca ttttcttttc tagaatctga tttgagagat 420
ttcccttggc accgtgtttt catattcgac ccaaattcac ggttga 466

<210> SEQ ID NO 191
<211> LENGTH: 547
<212> TYPE: DNA
<213> ORGANISM: Brassica napus

<400> SEQUENCE: 191

```
gaggcgaaaa cataaacaag gttcaaacaa ataattgaca attctttgga catacaaaaa      60

attatttaat ttttccaaat aaaacataat tgttgaactt ttttttgaac tgaacataat     120

tgcttaactt aagaagtaaa tctattcata attgagtttt aactgcaatt attaaaaaaa     180

attttgtaat atttgatcaa atatcaaaat atatattaaa ttaaaatact gaatggatta     240

tacatttaat agtaaatatt cggtttggta taatattttg gggagaaatt ttaactttac     300

ttaaaattta acatcacttt ttaaatgata gttatgttta taaacatctt aatgtgatat     360

attcactaat cactgacaag aacatgtgtt acaaacatct taatgtgata tattcactaa     420

tcactgacaa gaacatgtgt tacaattcgc tgacagctct attgccatcc atgcgcgata     480

cgtcaatttg ctttacattt atacatttgc attctcttct tctttttcct gaaacagttt     540

tggcgat                                                               547


<210> SEQ ID NO 192
<211> LENGTH: 327
<212> TYPE: DNA
<213> ORGANISM: Brassica napus

<400> SEQUENCE: 192

tcggtttttc gagggtatca aatttaattc tattaggata ttcttaattt ttagggaaat      60

taagcctaat aacaaaaaaa ctataattca ctaaataaca aaatcctcac tctcactcct     120

acttttcttc ttcctatttc tctttactct cattcctaaa agttaatttc catttttttgg    180

gttatttgac aaataaacca taaattttaa ttcggattcg ttttaagttt tttcccaatt     240

cagttcggat atagtaacac atcgcaaacc cagctgaacc cactaacacc ggattatgtt     300

ctaaaacagg ttcgattcta aatcgga                                         327


<210> SEQ ID NO 193
<211> LENGTH: 466
<212> TYPE: DNA
<213> ORGANISM: Brassica napus
<220> FEATURE:
<221> NAME/KEY: modified_base
<222> LOCATION: (419)..(419)
<223> OTHER INFORMATION: a, c, g, t, unknown or other
<220> FEATURE:
<221> NAME/KEY: modified_base
<222> LOCATION: (440)..(440)
<223> OTHER INFORMATION: a, c, g, t, unknown or other
<220> FEATURE:
<221> NAME/KEY: modified_base
<222> LOCATION: (443)..(443)
<223> OTHER INFORMATION: a, c, g, t, unknown or other

<400> SEQUENCE: 193

tcctgcagtt tgaaatcctt ggtaaatcca atgattttaa tatcagacaa ttagatttta      60

aaataaatca gatgaacttc aaaatcaaat caatggatta ttataaatca acaaaatgga     120

tttgtagtat tagtttatga taaagttaat aaatataaaa atatatcttt ttcatttttt     180

tcttatatgt tctcaaattc tcataacata tagaatatcc ccacctattt gttgtaatag     240

ttgttcttaa ctgattgata tgttctatat gctgattttg gttacaagaa gtcaagaact     300

tcttcatcat tattattttt agattttttt catcatcaaa atcttttttt ttggggttat     360

ttgtaaaaaa tgtgtaatta aaaatataat tttttgaact agaaaatatg atattaaana     420

tagtgataat agaatcgagn acncggaagt tggtttgggg aaactt                    466


<210> SEQ ID NO 194
```

<211> LENGTH: 273
<212> TYPE: DNA
<213> ORGANISM: Brassica napus

<400> SEQUENCE: 194
aagcttaata gcgacttctt cgttagtctg aacatcagtt cctgtaacca ccaacaagag 60
tcatcagaga ttcaacatac ctaattgacg cctagtctag tcacacatga atgaaagaaa 120
aagtagaaga gtgagagagt gagaagagga agaaggaacc gaggtaaatc tctccgaaag 180
agccgctccc gattttgcgg ccaagtcgga acttattccc aatacgagac tccatcttcc 240
cgagagagag agagagagag actagggttt tca 273

<210> SEQ ID NO 195
<211> LENGTH: 347
<212> TYPE: DNA
<213> ORGANISM: Brassica napus

<400> SEQUENCE: 195
aatggatgaa ctcgagacgg tttatctgac acaagaagca aaacaagtta atccatcagt 60
gaaagttgta ataacaattg caatacagtg tacaaagcaa gagataccat ttgatcagca 120
agcatgagaa cagtcttcaa agaaaacttg cggttgcaat agccaaagag atcctcaagg 180
ctaggaccaa gcaaatccat gactaagaca ttgtagtcac cctcaacacc aaaccactta 240
atgtttggaa tcccagctgg gcattaaaaa cgcaaaaaag aaaatgaaca aaactaataa 300
taaactgtaa aaagaagaag aagaagacag gaaacgaggg gttatca 347

<210> SEQ ID NO 196
<211> LENGTH: 382
<212> TYPE: DNA
<213> ORGANISM: Brassica napus

<400> SEQUENCE: 196
tgtcagcatt cagcagaagc ttattatgag tttaatagcc ggagagagga aatgaattaa 60
accttcacga atgaaaaggt tgcggaagag tctcttcaaa taagcatagt ctggcttatc 120
atcaaaccta agtgagcggc agtaatgaaa gtaggatgca aactctgttg gatgacctct 180
gcataacgtc tgaaaataac acggactcaa agttacattt ctatctatat aatcaacctt 240
ctctacttca tcattatttc cttcgtacat agactcatat aagtttctga gagtgcacaa 300
gaacttactt cgatggaagt agaaaccttc ttttcactaa tcttgtcgta tttctgtttc 360
ttgttcccag ctttcaatcc ct 382

<210> SEQ ID NO 197
<211> LENGTH: 533
<212> TYPE: DNA
<213> ORGANISM: Brassica napus

<400> SEQUENCE: 197
ttgacggtta cccaaaatac cgagaaaaaa taataataag cctttgaatg taaatgcatt 60
ttattcatga tgattcaaca tttcaaattc aggataaaga aatataataa aataataaat 120
tcaaacaaaa aataataata atagataatt actagtatta atttatgttg ataaactatt 180
ttactcataa actttcgttg aatatgctgt tttagtcgca gtgttaatca accattataa 240
ttgacaaata gtagacctaa actgacttta aagtttttat ttagcaaaaa cactttttcc 300
acaaaatggg tttttaactt ttgaaataat tatcagagat aaggaactta aaatacttcg 360
gtttgtttta tctatacaat ggagaagacc aatgaaccat ataatttaag cactttggta 420
taaataaatc tctatccctc ccttatatca aatctctaac ttcaaagcct ttcttcagaa 480
gaatcataga ctaccttcaa atcctcaaga aggggtgagg gtgaagcaat caa 533

<210> SEQ ID NO 198
<211> LENGTH: 711
<212> TYPE: DNA
<213> ORGANISM: Brassica napus

<400> SEQUENCE: 198
aaagcatcct ttgcaagggg atcttctata tgctattgaa agagtgttga agctttcagt 60
cccaaatcta tacgtgtggc tctgcatgtt ctactgcttc ttccaccttt ggtatgtatg 120
ccgtgatcct ttctccaaag atgaacaaca gaaaaaggat atatctcatg aagaaattga 180
taacattagt tttctcacac agttttgaga tgtaatttca gtttctgatc acaaatctct 240
ttgcattgtg ttcttgtcca caggttaaac atattggcag agctactctg ctttggggac 300
cgtgagttct acaaagattg gtggaatgca aaaagcgtag gagatgtgag ttgtcattaa 360
ccttttgtta ctaaagaaca ttgacgtttt atgttgtcac acatgactaa ccaaatttca 420
tgtattcact ttcttccttt gtcagtattg gagaatgtgg aatatggtat ggctctcttc 480
ctaaaacatc gtcgtcttct tttctatacg aaacagaagc agaaagctaa cggagagctt 540
tttgtttttg ttttaacagc cggttcataa atggatggtt cgacatgttt actttccgtg 600
cctgcgcata aagataccaa aagtgagtgt gtatatgtag attagtgatt tgagatgatc 660
gagattgttt tctgtgtttc atagctttaa ccatccactc atttttggtt c 711

<210> SEQ ID NO 199
<211> LENGTH: 400
<212> TYPE: DNA
<213> ORGANISM: Brassica napus

<400> SEQUENCE: 199
aaattgttac aaagtatgag aaatgaatat atcaaatcat actcttaaag tgatttgtgt 60
ttggtttcaa agtgaatgaa tttattgaaa taatttatac aattgaaagg gaaaaataag 120
cttatcttat tggctctctg cattttaata atttattgaa ataatctata caattaatag 180
gaaaaaataa atttacctta ttaccttaat taattaaaca aaaaataaaa atgtatgcat 240
gtgttataat acatagtatt caactattac cagcataatt tatatttaac tatttttatt 300
agtattttat aaaggagcct aaaattaatt aaataaaata ttaaaaatgc atgcttatgt 360
cataatatat ttgtagagaa tgagtaaaat gtttactgaa 400

<210> SEQ ID NO 200
<211> LENGTH: 554
<212> TYPE: DNA
<213> ORGANISM: Brassica napus

<400> SEQUENCE: 200
tttccacaca aatcggattt aataattaaa aatccaataa aactaaaata tttgctatta 60
acctgttaat ctactctggc aaaacctaaa agaaaaactt ataatacttt ttgaaaaatt 120
aaataaactt ctcttatact ttatataaag tacataaaac taaataaatt atttgatttg 180
tcatagtata tttttaaatt acacataaag aagaaggttt gtttgttatt agttattcct 240
ttcatatata tatatatcta tcttattaaa acaggaacat tacaactttt tctaggtgga 300
tttttaaaga tggacctcat atatttaaat taaatgtctc attctttata tataatatgt 360

```
accatactct aactttgcat tgatgtattt ccttaaatac agttcttctt tttgtccata    420

ttccatatat gatttttaca tttattacat gtcgatttaa ataagatata tactaagaat    480

actaaaaata ttaatcgttc tataattacc ctatacaatt cattttaaat tgatcagtaa    540

actttcattg gcca                                                      554
```

<210> SEQ ID NO 201
<211> LENGTH: 525
<212> TYPE: DNA
<213> ORGANISM: Brassica napus

<400> SEQUENCE: 201

```
accaaaccga gaacaaaata ggtgtctaaa tttttaaaat acaaattata ttctttcaaa     60

tattacgtct attcgatttc taaataaccg agtatcctga aagtactatt tataagctaa    120

attatccata aaaataccag aatattgttt tcaaaatatt taaagtattt gcattatctg    180

atattttaac ccaacaatat gaactaccta atattaaatt gaaaatccta aattatccga    240

tatatttatc tataaattcg tgattaccgg aaaactcagg acaaagcaaa actgaattgg    300

acctatattt ttctggaata ttagtcggtt tccaactata ctactaaaaa acaaaccaaa    360

ataacaaaat aacaacacaa ctaaaaccag accattttgt aaataattga acggttcctg    420

aatttgtaga accataacac aactaaaacc agaccttttt gtaaataatt gaacggttcc    480

taaatttgta gaaccaaaac accaaaaaac caaagtattc gaacc                    525
```

<210> SEQ ID NO 202
<211> LENGTH: 543
<212> TYPE: DNA
<213> ORGANISM: Brassica napus

<400> SEQUENCE: 202

```
tggaggtgtc aaagtgtggc atcacataag agttttaaga gtttgttgtg ctttagtttt     60

tgagtgagtt ttctaaggca ataagaagag ttatttcttt acgagcaagc ttcttagttt    120

cttaagttct ctgtttctac agattttctg tttatattac ttacttgaaa tattcttttc    180

ctataaattc ttatgcaaat tttcagaaca atcttgtctg cagatacatt ttgattttat    240

agtctgcgca aggcaaatac agttttgatt taatgataca gaacagagtg ggttagttcc    300

aggtttggtc acgaacaatc atcttttaca ttggtctatg taaatcaagt catatccaga    360

aagcagatag gcttgtttaa gagatgtggg agatgggtat ttgtacacac tgagtttttt    420

ataacacttt taccaagggt gtttctagtg ttaacaatat cgataaagat cttagatctc    480

tatctcttcg ctactatatg gagaataatc atcatggtat taagccaaat aaagtgactt    540

gcg                                                                  543
```

<210> SEQ ID NO 203
<211> LENGTH: 463
<212> TYPE: DNA
<213> ORGANISM: Brassica napus
<220> FEATURE:
<221> NAME/KEY: modified_base
<222> LOCATION: (22)..(22)
<223> OTHER INFORMATION: a, c, g, t, unknown or other
<220> FEATURE:
<221> NAME/KEY: modified_base
<222> LOCATION: (88)..(88)
<223> OTHER INFORMATION: a, c, g, t, unknown or other
<220> FEATURE:
<221> NAME/KEY: modified_base
<222> LOCATION: (93)..(93)
<223> OTHER INFORMATION: a, c, g, t, unknown or other
<220> FEATURE:
<221> NAME/KEY: modified_base
<222> LOCATION: (96)..(96)
<223> OTHER INFORMATION: a, c, g, t, unknown or other

<400> SEQUENCE: 203
gaaccacgac tttgggtctg anatttaacg ggacagaaca gagtatacca agactcatgg 60
gttacagtga ctcgtcttat aacactgntc canacnatgg gaagagcatc acaggccatg 120
tattctacct caacgacagc atgatcactt ggtgttcaca aaaacaagaa attgttgcat 180
tatcatcatg tgaggcagaa tttatggcag gtacagaagc agccaaacaa gctatatggt 240
tacaagagtt actcggtgaa atcttggagc agtcgtgtgt aaaggtgact atacggatcg 300
ataatcagtc tgctatcgct cttaccaaga atccggtctt tcacggaaga agcaagcata 360
tacattcacg ataccacttc ataagagaat gtgttgaaaa gggactggtg agtgtagaac 420
atgttgcagg gagtcaacag aaagccgaca ttctaaccaa agc 463

<210> SEQ ID NO 204
<211> LENGTH: 269
<212> TYPE: DNA
<213> ORGANISM: Brassica napus

<400> SEQUENCE: 204
gagaatattg gaagaaagcg gaatgaaaga ctgtaacttg gtacacacgc caatggagtt 60
aggactaaag ctttgcagag ccgatgaaga ggaggagatt gatgctacaa tatatcgaag 120
aaacgtgggg tgtcttaggt atttgcttca caccagaccg gacctagctt atacggttgg 180
agttctgagc cgttatatgt cgtcacctaa aacttcgcat ggagctgcca tgaaacattg 240
tttgagatac ctcaaaggaa ccacgactt 269

<210> SEQ ID NO 205
<211> LENGTH: 747
<212> TYPE: DNA
<213> ORGANISM: Brassica napus

<400> SEQUENCE: 205
gctctacgag tgaggatcaa agtcacgaga atatgatcaa agcagagcct gcagaaacag 60
aaacattgaa gaagaagaca gtcatgagaa tcaagaacct gaaagtgaga atgaagcggt 120
acctctaaga agaagcgtga gacaaaccat gacacctaag tacctggagg attacgttat 180
ggttgcggaa gaagaaggag agttgctgtt gctaagtatt aacaacgaac ctattaactt 240
tgcagaggca agtgagcgtg aagaatggat agcagcctgc aaagacgaga tagcaagcat 300
agaaagaaac agagtatggg atctagttga tcttccactc ggagtaaagc ctattggttt 360
acgttggatc ttcaagataa agcgaaactc ggatggatca atcaataagt ttaaagctcg 420
actggttgca aaagggtatg tacaacaata tggaattgat tttgaagaag tatttgcacc 480
ggtggctcgt cttgagacta taagattgct tgtgggtata gcagctgcaa aaggatggga 540
agtacatcac ctagatgtta aaacggcgtt cttacatgga gaattaaaag agaccattta 600
tgtaactcaa ccagagggct ttgtggtgaa aggaagtgaa cgaaaggtgt ataaactcaa 660
taacgcattg tacggattga ggcaagcacc aagggcgtgg aaccataagt tgaatactat 720
tttacttgag cttggattcc gaaagtg 747

<210> SEQ ID NO 206
<211> LENGTH: 219
<212> TYPE: DNA

<213> ORGANISM: Brassica napus

<400> SEQUENCE: 206
agcttatagg cttctagacc caaaatctcg aaagatagta gtaagccgag atgttgtttt 60
cgatgaaact aaagggtgga attggggtga acaaaacaag gaagatgaaa attttactgt 120
cagtcttgga gaattcggaa atcatggtat tcaaagctct acgagtgagg atcaaagtca 180
cgagaatatg atcaaagcag agcctgcaga aacagaaac 219

<210> SEQ ID NO 207
<211> LENGTH: 363
<212> TYPE: DNA
<213> ORGANISM: Brassica napus

<400> SEQUENCE: 207
agctttaatt catgtatttt tacaaatttt gttactagaa aaaaaaaaaa tttagtatta 60
attaaaataa ttagtgacta gtcaatttta cttataacaa aatcttttta gaaaaaataa 120
gaaaatcttt aaaaaattca aatatatttt tagaaaatac tgaattagtt tagtaacaaa 180
aaaatcaaaa atcatataat cttccaaact aaaaaataat tgtgtaattt tctaaatgcc 240
tcttgaccaa gtatacaatt taaaaaataa attaaaactc aaaatgataa tattccaagt 300
tttataaaat ataaagtcat acaagttaaa atataaattt ttgaaatgta tcacaaaaaa 360
att 363

<210> SEQ ID NO 208
<211> LENGTH: 678
<212> TYPE: DNA
<213> ORGANISM: Brassica napus

<400> SEQUENCE: 208
ctgtaacttt caacccaact cgtagaagta aggacatcgt gatcaaagat ccacacatgc 60
ttcatcagcc tgcatctcca acctcgtcct gaataaacac acacagagct atgaaagggt 120
acaaaaaaaa acaagtactt aggcagctat ctggaatcta aacagttcaa gaaggttcta 180
gatgaaaacc ctaagaaaga aagaaagatt ctgaatgcca ctcaaagcat taacagtagg 240
aagctgactt acttttgacc gaaacaggca ggaaggttaa tggaggggca catgtcaatc 300
acataaaata aaatgacact taacttacat tagctttagt ggcctctgaa gtaaagtatg 360
tggtgaggag gccattcagt ttgggtataa tatcaactct gccacgggat tgtctttgag 420
aagacccgtt gctaatactt cttcctgaaa aaagccaatt aacacaagct ttgataccca 480
aagacataat taagatgtga agatatggtt catagataag ctttatacct tcattgcttc 540
agatcttgaa ggtgcgtcaa cagcaagaac agctcttcga gctcttcgca cagtctgtcc 600
taccagttca tatggcagca attctcctct atgctgctgt gtgaacctga agaaagctaa 660
gaagagtaat ccccaaaa 678

<210> SEQ ID NO 209
<211> LENGTH: 364
<212> TYPE: DNA
<213> ORGANISM: Brassica napus

<400> SEQUENCE: 209
aagcttgatc aaagatcaca gtcttacaaa gaaacagaaa acaatttcag tgaaagaaca 60
gtatttacct tatttactct aaaattttta aaacagattt ttttcatgtt cagtaccaac 120
atagatggaa tcaaaaatat tattaaatca tcatactcca tcatgtatta caaactggtg 180
gatttagtat ttttgaagac cagacatatg cttaaaatca taagattccc gttactgcta 240
ctgtgctaca ccagtctagc cggtgacaga cacatagctg atattgaaag ttccttgaag 300
aacaatgagt gtggtcagaa gttgcaatta tattgtttgc aaacctgttg ctcattagtt 360
tgtt 364

<210> SEQ ID NO 210
<211> LENGTH: 201
<212> TYPE: DNA
<213> ORGANISM: Brassica napus

<400> SEQUENCE: 210
cagaccgttc aagttcatgg cgaagagaga aagagggttc agtttcgcat tgttgacgaa 60
gagtttgttt tcacaatttt tttatttcgt tagcttatat acgtgatatt ggttgcttag 120
tttaatagtt tatatgcttt tatattgaca gaggaaacaa tattgcatgc tgtctttggg 180
gatcatatgc cgagcaactt g 201

<210> SEQ ID NO 211
<211> LENGTH: 238
<212> TYPE: DNA
<213> ORGANISM: Brassica napus

<400> SEQUENCE: 211
ccttctccaa accggtaaac ggttagccac cgccgcgtcc cgtcgccaga gcatatcctt 60
atccgacgac agcttcatcc tcttctcctc cgccgacgcc gcttcctctt ctctcaccga 120
atccgaaagc gtcgctcacg tgctatctca catcaagctc ctcttacgac ggcgcgccgc 180
cgcactcgcc gctctcgacg ccggactcta caccgaatcg atccgtcatt tctcaaaa 238

<210> SEQ ID NO 212
<211> LENGTH: 623
<212> TYPE: DNA
<213> ORGANISM: Brassica napus

<400> SEQUENCE: 212
agaccaagag gaagcgtagc ttccgccttc cccttcctga tgttatgagt ggtcctacga 60
tatccatgga ccacttcatg aacgggacgg agcggatatt gaggatagtt tttccgcagg 120
ctgatgtata atcggtgtat gcctttggca tttatcacat gaagaggagt aaacctcaca 180
gtcagcgata atggtgggcc agaaatagcc ctgtcttttg attcagatag ctagagctct 240
gcccccaagg tggtttccac aggagccgtc gtgcatttct ttcataagat tgatagcatc 300
gagaccatgg acgcatttta ggtaaggtcc ggaaatactt cgtttatgga gggctgactc 360
gattatgcag tatcttgcgc ttaatgcttt gagttttcgg gccttaccct ccaagatgta 420
ctgcatgatt ggtattctcc aatcctctct cccaaagatt ttttcatgaa gagatgaggg 480
cgggtgttgt tcaggtccct gtgtgtcgtg acctgatgtc ttattgcccc cggagatatt 540
ggtcggatta ggctcgaagg agtctgaatt ctgaggaata tctccagttc tggtgttgtt 600
ctccggagtc tgggttgttt ctt 623

<210> SEQ ID NO 213
<211> LENGTH: 198
<212> TYPE: DNA
<213> ORGANISM: Brassica napus
<220> FEATURE:
<221> NAME/KEY: modified_base
<222> LOCATION: (43)..(43)

<223> OTHER INFORMATION: a, c, g, t, unknown or other

<400> SEQUENCE: 213
caatgattta tacttcgttt ttgctttttt tttttgtttt tgngagcagg tggatgccgt 60
ggtgtaccta gtggatgcat acgacaagga gagattcgca gaatcgaaaa aggaactgga 120
cgcacttctc tcagacgaat ctttagccac cgtccccttc ctcatcctag gaaacaagat 180
agacataccg tacgctgc 198

<210> SEQ ID NO 214
<211> LENGTH: 525
<212> TYPE: DNA
<213> ORGANISM: Brassica napus

<400> SEQUENCE: 214
catttggttt gtccgtgtgt cccatatgat tcaaaatctg agagcttatt atgtctatat 60
aaaacacctt attaaaatta aggtcaatat ctcataggat tgtgtataga ttcggctgtg 120
tgtacttagc tactcaagta attagagccc cacttatctt atccactttc actaataaat 180
cactcgtgct tgaataaaga agctggaacc gcttaatttt tatcaaaatc aaataccggt 240
ttaacagccg ccgagatgca cattctcgac accggagctc gtttctccgc cgttagattc 300
tcaccggtat tcaatcctac tccccgcaga agatacgtca tcgtaaggta tcttcttcat 360
ttctccatct tcttctactt cacactgagt tgtctctctc tcgctgcatc caaatcattg 420
agtctctctc tctctcaggg ccaatctccc gtttccgaag catcaagcta agtaccacaa 480
agagctcgaa gccgccatcg atgctgttga aagaggttgt cgcct 525

<210> SEQ ID NO 215
<211> LENGTH: 379
<212> TYPE: DNA
<213> ORGANISM: Brassica napus

<400> SEQUENCE: 215
cattttcttt aacaacgcgc ttttgatttc cattgaccgt actttgaaaa acactcaatt 60
cggcccatca catgtcatac ctttttctca gcaatagttc atttcgtatt ttattaacta 120
ttttagctct gttctgatca tacatctata tatatggatc atatacaata tgaaatagga 180
gtcaaacatg aagctccgaa gaaacaaaca tcctaagcag caacggctag caacatagcc 240
tagttggcca cctactttaa tagttttaaa cgacgactaa gaaaaatata aaatgagcac 300
accgtctttt aaaatattcc atgtggtgat gtatccacgg tttgcacacc ttcctaaccg 360
tactacatgt cgccgtcgt 379

<210> SEQ ID NO 216
<211> LENGTH: 446
<212> TYPE: DNA
<213> ORGANISM: Brassica napus
<220> FEATURE:
<221> NAME/KEY: modified_base
<222> LOCATION: (416)..(416)
<223> OTHER INFORMATION: a, c, g, t, unknown or other

<400> SEQUENCE: 216
tctctcacac tttctctcac cagatctaaa gctgaccaca gtcagcgatc acaaccttct 60
tcgaggtcct tccactgtca gatccaacct tctcaatgtt cctaacgaca tccatcccct 120
cgacaacctg accgaacaca acgtgcttcc catccagcca cgacgtcttc tcagtgcaga 180
tgaaaaactg agatccgttc gtgttcggac cagcgttggc catggacagg atgcccggac 240
cggtgtgttt cttgacaaag ttctcgtcct tgaacttcat gccgtagatc gactctcccc 300
cggtcccgtt cccggcggtg aaatctcctc cctggcacat gaacttgggg atcacgcggt 360
ggaaggccga gcccttgtag tggagcggct ttccggattt gccgactccc ttctcnccgg 420
tgcagagggc gcggaaattc tcggcg 446

<210> SEQ ID NO 217
<211> LENGTH: 275
<212> TYPE: DNA
<213> ORGANISM: Brassica napus

<400> SEQUENCE: 217
caaatcaata ccattaaaag tggatcatta tcattttata ccattaatga aaatttcatg 60
tttttcaaaa atatcctaat tttacaaagg attattaact ttcattaata gcatttttgt 120
cttttgattt tggtcatgca gacataaatt taaatagatc aatgaataat gagcttacac 180
atacttactt ataaaatatg ctattttta ttttatataa atattctaat tttaaatatt 240
atacatatat attgtgaaag gaaattaatc aaaaa 275

<210> SEQ ID NO 218
<211> LENGTH: 122
<212> TYPE: DNA
<213> ORGANISM: Brassica napus

<400> SEQUENCE: 218
aatagaggga gaggatgaaa gaaccacaac cgcatacaga tacacatgtg ttagtatatg 60
aaaacgcacg tatgttttat aaataaaatc ccttacttta taacaaaacc tgttaggtag 120
ct 122

<210> SEQ ID NO 219
<211> LENGTH: 252
<212> TYPE: DNA
<213> ORGANISM: Brassica napus

<400> SEQUENCE: 219
tcacattagt aaaacgattg tccacccaat tataaccaaa agcggatccc tattcgttac 60
ccgtaaacca taaacacatt ttttttctat tttctaaaac cacacgatgt atctcttctt 120
ttctagaatt agtgttcata gaaagtgagt catgattact tttcaagacg aaaaatcgat 180
ctgaggaagt tttctaagat gagtacgtgc ggttcctttt taggaccaca aacggagtcc 240
aaaaaatcaa tc 252

<210> SEQ ID NO 220
<211> LENGTH: 587
<212> TYPE: DNA
<213> ORGANISM: Brassica napus

<400> SEQUENCE: 220
ccttagttta gttgtaggtg gtggaaacat atatggacga cggtttctgt tctcacctgt 60
cgtctgtttt cttcttaatt tttgctctca gatcatcaga gtttggtggg aatggttaaa 120
tcggacactt ccttatttgg aatttaccat tgggaagcat cagagggagg gaactgagag 180
tatgcttgga gggatggaac tgtcttgtgt agccttctga atcagcttag tcctggttct 240
gtgacaacgg tacttatgaa tttctattta ctaggataat gtaccttgtc gttttctttt 300
tttttcttcc ttgtctttgt catttgttgc tagcagggcc ggctctgaga attcgggga 360

```
tatagacggt ttaagaagga atttataaat ttgggggctg aaattcctat ttatataaac    420

tgggggtcta tccatatata atttttcaaa aaaatttcgg gggcttaaag gctaatgtct    480

catccggctt ggctcagggc cggacctggt tgctaccctc acactcttcg gatatttata    540

tagggaggca gctttgagcc tgcttatgtt aaaattgagc ggtttct                  587


<210> SEQ ID NO 221
<211> LENGTH: 637
<212> TYPE: DNA
<213> ORGANISM: Brassica napus

<400> SEQUENCE: 221

ccttggctat gtgcttatgt attttcttcg tggaaggtat atatctgctt cccatttgct     60

tttatttggt ttccatttca ccttaccctc tgtttcttct tgctagtctg ccttggcaag    120

gccttcgtgc gggtacgaag aagcagaagt atgacaagat cagcgaaaag aaaaggctta    180

cacccgttga ggtaattagt cttaaaaggc acctgaagtg tcatttactt atcaaaagat    240

ataatttatt atctccattg acaggttctc tgtaaatcct ttccacccga gttcacatcg    300

tactttctct atgtacgatc attgcggttt gaagacaaac cagattatcc atacctaaag    360

aggcttttca gggatcttgt tcatccgaga aggttgggga aaactactta tgctttaata    420

tttcacataa acacacaata tgtaaagttt tttttataat gttataatat atttgcaggt    480

tatcagtttg actatgtatt tgattggaca atcttgaagt atccacagtt cggttcaagc    540

tccagctcca gctccaaacc aagagtaagt aactatcatt ttcaattcct cttgagcata    600

ctatcaaaca aaccctcacg attgtctctg tgtttta                             637


<210> SEQ ID NO 222
<211> LENGTH: 235
<212> TYPE: DNA
<213> ORGANISM: Brassica napus

<400> SEQUENCE: 222

cattgataca tgaatgcaaa gaagaaaagt ccagaccttt gttcacattt tggcctccag     60

gaccaccgct tctagcaaag ttaagcgtaa catggtctgc aagtatatac caaacagata    120

aacaaatgaa accatgagta tgaacagatc gaactataat tgtaattcca tcaaaatcag    180

tataaaatag agttctataa taacatttgt agcattgtct gtaaatgttt tcatc         235


<210> SEQ ID NO 223
<211> LENGTH: 281
<212> TYPE: DNA
<213> ORGANISM: Brassica napus

<400> SEQUENCE: 223

ctgcataaaa ttatcgaaga cagataacac aaagaaagga cataattgtt acattgaaac     60

aacattgtta ttgttacatg taattccaac ccactgggtt ccacaaggat cagagccttt    120

ccagttctca ggaaacctgg tccattcact cttcaaggct tgtaatgcag aagctgcgcc    180

aattttgaaa agaaataaaa tattcctata tctgtctgaa taactcggat catgatctaa    240

tatacttacc gtctaaagga tttgttagcg ctgaaacaga a                        281


<210> SEQ ID NO 224
<211> LENGTH: 406
<212> TYPE: DNA
<213> ORGANISM: Brassica napus

<400> SEQUENCE: 224
```

```
ctttgtcatt gtgtgtgtgt gtgtgtgtgt accgggccga tctttgtcat tgtgtgtcat     60

ttttagctgc aacaatgcat ttgaaaaagc tggaaagaga cgagaatcta gtggctgcat    120

tctcttacat ccattgtgga tgagctccaa ctgtccaaca ggctttgaaa gagtttggta    180

taaatgattc acatcttgat gaaatgatca aagacattga tcaagacaat gtgagtagct    240

atctttacag ctttcattag agagatgctt atggtgtatg gtttttgtag gatggacaaa    300

tagactatgg acagtttgtg gcaataatga gaaaaggtaa tggcagtgga gggattggta    360

agagaacaat gagacacact ccacttggca aattggaaat catatt                   406


<210> SEQ ID NO 225
<211> LENGTH: 350
<212> TYPE: DNA
<213> ORGANISM: Brassica napus

<400> SEQUENCE: 225

aattcttgct ccattatgat ttcaccaagt caacaaaatc ttctttctac tagtgcgata     60

gatcactaag cagcgtagta caacaaccac atgggaggga acacgataat gaacaaacct    120

gttgaatatt gatgcggcgg gtgggtgctc aagaagctta ctcgtgaaat cgagtcttgc    180

aaagaaacct aagctgagtg tgagtaatga atttatacat aaaatataaa tgggcctgaa    240

ctccaagctt attccaagta ctatgggctt taggccgtaa ttctgtaagc aaaataaagc    300

ccaaataatc ttttgatttt tcttttttc ttttcctga tcgtcttgtg                 350


<210> SEQ ID NO 226
<211> LENGTH: 591
<212> TYPE: DNA
<213> ORGANISM: Brassica napus

<400> SEQUENCE: 226

tccactccta gttcacaatc tattttttc ttttaaaaac atagtaaaca tacaatataa     60

ctaatagtat tttatacgta ctatcatata aataatcaca tatattatat ttctaaaatt    120

taatgtgaag tacaaacact tgttacaatt ttgtttgaaa gattttattt gtatattaga    180

agaaacttgt tacaatatcc ttctttaaaa aatcatgtgc aattttttta aaaaaatatg    240

gttaaagatt ggagctggtt aaagatggtt agacagaaga taaatactct ttaaccataa    300

cacaacccat taaaatgttg aaaaaaagaa aggtataggg ctttaataat gaaagatccg    360

tgagatgcaa gattaatata taatccaaac tcaatgttta ataccagtgg cattctgatg    420

taaataatga gaaaaattta gggttatttc tcatttgcac ttcactttta ataggataga    480

taagaccatg ctttaaaaaa ttgttagtag tgtagacaga tatggtgttt gttagatata    540

tcgatcaatt tcagatgttt ttgtcccttg tgtattccaa cattttgtat a             591


<210> SEQ ID NO 227
<211> LENGTH: 454
<212> TYPE: DNA
<213> ORGANISM: Brassica napus

<400> SEQUENCE: 227

tccattgcag aattcacctg cggaatgtaa tttccttcac ctagtcgtcc acctgcaaca     60

caatccgcaa gggtgtgttg tagcttctcc attccttgag ataaagcgtc ttcagcttgc    120

tggcaagatt gtcttagatt gcatacatct agaatctgct gatccgtcat gacatcaaaa    180

tgtggcaaaa gaacctgcaa aacaaagatt taaaaacatt gtattagata caacgttcca    240
```

agtcaaaagt tagaagagat cttaaataat atataaagag aacggcctat aagattgatt 300
tttaggttaa cacattattt tagttgtgtt tattttgatt gttctttgtt acttgttttc 360
taccttgata agatccgagg gtcgaaagcc gccaatccat atgaaaaaac gttctgcaga 420
agttctccac attcccgaca tgacgaagaa aaca 454

<210> SEQ ID NO 228
<211> LENGTH: 233
<212> TYPE: DNA
<213> ORGANISM: Brassica napus

<400> SEQUENCE: 228
cttgagggaa ggagacgaga tgagagtcgt catcaaagat tctacagtga agaagaagaa 60
gaagatattt tcgtctcttg ctaacggaga aagagagagt gaagtgaagt gtgtgatata 120
tcacgtgatc atcacgtgtg ttgatatctt cgtcaatggc gccatttttc aaggccgtat 180
tttgggcttt tagtgatggc ccccaaattt ttaaaaaacc catgacccaa aat 233

<210> SEQ ID NO 229
<211> LENGTH: 533
<212> TYPE: DNA
<213> ORGANISM: Brassica napus

<400> SEQUENCE: 229
atatccttaa acccttgcgc aatcttctga tcttctccca ctggcctttt agccttcgcc 60
tttgcagctt taacaccaac aggcctttcc atagcgtcat catccccatt aacacttggc 120
atagagcctg atgcctgaaa agattgttct tcccccaccc tctttctttt cgaacctgag 180
ctttgttgac tagttccttg agtcccacac catttctgat cattcctaag ctctctccac 240
gcatgttcca atgagaactt cacattgtaa tcgctgaaga atattgcata tgctgctttc 300
aagacgtcat cttcattctg cccactgctc ctctgttttg tggcagcttc aaatgacccc 360
acaaactagc agactccttc atttatcttc ccccaccttt gcttacagtg ggtcagctct 420
cttggaggca aaccaaccac ctttggactt gcgttgtagt aagccgtgat cctcttccaa 480
aaggttcctg ctttttgctc atttccaacg agtgggtcct tggaggtatt caa 533

<210> SEQ ID NO 230
<211> LENGTH: 699
<212> TYPE: DNA
<213> ORGANISM: Brassica napus

<400> SEQUENCE: 230
ggtctcaggt tttgtgggag taatatcggt tacctctttt cctattactt tgtcctgtat 60
agaaaaatac tcatacccat tatcatttcc cttgcgtaga actatatttt atataaatag 120
ttctattttt tttttaaatg agtcgttgaa acttagaacg caagaaaagc ttttatcttt 180
tgatcatgtc ctaattcata agaagatatc atttattttt ataaaatatc aagttatatc 240
taacgattct taaacatggt cgaatgttca gaaataaaaa tgaagtcttt ccaataataa 300
ataaaatctc ttctaaaaat atttattttc aaaacaaaca tgtttatgtt tttttttttt 360 gtttttttgtt tttttttgag aattcaaaac agccatgttc tgattgtata acccacttac 420
gtacaaacat ttaaatgatt tacgtacaga taaatgtgga aaacgttacc tcgtgaaaca 480
agggactgag agattggctt ttgccgtgtt ccttcttcac atcatcttca accagaatct 540
cttttccttt ctcgctccgt cgtgccgtaa gcagctgtat caaccgcctc gttaggagca 600
ttgctctggc tcttttccgc cgtaatcttg ttatgatcac tcggagccgc catatctctc 660
tcaaccggaa ccatatcctc ctcggaatct ttgagaacc 699

<210> SEQ ID NO 231
<211> LENGTH: 477
<212> TYPE: DNA
<213> ORGANISM: Brassica napus

<400> SEQUENCE: 231
cttggtcaca cccatcttct ctctgcgtaa atgttatgca gagtttgcaa aagcatttgt 60
cccttggtgt gagaatcctc tgtgtgctct aaatggaccc ggttcgaata tattcgatac 120
tatccataaa cacatcacaa accaagtaag ttcttttctt ctaatgggct gatgatgtcc 180
atttagtttc cgtccatttt ccgatttaac tttaacgtaa cgtttatatg tccatgcata 240
aggacaatta agatacaaag ataaatgaat cagccaatat ggaaatataa ttatttattt 300
cccttgttgt gtaatatccc ctgcttgatt cagtatcaaa aacattgaat atgcttccaa 360
ataaatatat ttgaatatat attctactac aaaacatatc aatttacgtc gtcttaggaa 420
acccttattt aatcaaatct ttgtctctct ttctggccgc agagagttta tcggaca 477

<210> SEQ ID NO 232
<211> LENGTH: 480
<212> TYPE: DNA
<213> ORGANISM: Brassica napus

<400> SEQUENCE: 232
atcaaccacg ttcatccatg gatttctgga aaaggtatca aataagagga agaagaagat 60
ggagaaaaag ggcatcaagt taagaaaaca agtttttttt gttcgaattg aacgtttgat 120
taaatctaca aactaagtgg atctaagaag aagtgcccaa gaagaagaac aaggagatcg 180
agtagcagag aacaagctac aaagaagtga gaagaagaag aagagacttg agccacaaga 240
aacaaaaaag tgaagaagaa aggtgagtgt gagaacaaaa acagagtaag tgagtaacca 300
agaacaaaga gagtaacaga gaataagcta caaagaagtg agaagaagaa gatacttgag 360
ccacgagaaa cagaaaagtg aagaagaagt gtgaatgtga gaacaaaaac agagagtaag 420
tgagtgaaca agagaaacaa agatgatgga gaggctgggc tggccgagag tatttgagtt 480

<210> SEQ ID NO 233
<211> LENGTH: 579
<212> TYPE: DNA
<213> ORGANISM: Brassica napus

<400> SEQUENCE: 233
atttaccaaa tggatcactc tggatatttg ggttagaatt taattttaaa tttgttaatg 60
ggacattatg tcaattaact tatttagtta attttattct tgataaaccc aaacaaaata 120
tattaaaatt tggtgacttg gtcaaagtca caatattact ttgcaaacta accttcaaga 180
tcaaggaaat caattccata attagaattg atatgtacgt tagttgactc ctttaatttg 240
cataacgtgt actttctctt caagttataa aaagagatca cttgtgcagt tttctacgca 300
cggagaaata acaattctcc atatttcttt tttcttttga tttgttattt tgagtctgag 360
agtatacaca aaactagttt cgtcgggctt ctgatagagt gacgcaaatc agaatatttt 420
ttgcatttgt atcttgggac tcattacgtt attgaaccgt cgcactacga gcgtattttg 480
aattaaagaa agagatctcg cctctgtagt tgaatcatca ttttcttaat ctttggtata 540
atcttatcaa atttattctt tacaatgttc aattctcgg 579

<210> SEQ ID NO 234
<211> LENGTH: 496
<212> TYPE: DNA
<213> ORGANISM: Brassica napus

<400> SEQUENCE: 234
caattccaca acgtagcaga gctttgaaac ggaatagata tctgactttt ctaaaatttg 60
gtcagattga accaaatatt acacatgtga aattcggtaa ttagttaata tttaagaact 120
aaaagtcgag agaaagaggc aggcggaaac gagaggtggg aaggattgga tacttccacg 180
caaaagggta tcttcttttt tttcctcctc ggatacttcc gatcatgtta ttaatttgag 240
gttcttaatt tttgatttga cagttttttt tgttttaatt aaactaagaa ccgacagttt 300
tttttgtttt ttttttcata attagtaaag ggttctttgg gtggagttct taccgaaata 360
taagactatg attaatccgg gtttttaggc tggggttctt agctttggtt aagaaccatt 420
tcttagcttt taactaaaaa aaactaaaaa cctgctctca aaaaatagat ataagagccg 480
gttcttagtc gaaaag 496

<210> SEQ ID NO 235
<211> LENGTH: 574
<212> TYPE: DNA
<213> ORGANISM: Brassica napus

<400> SEQUENCE: 235
agcttggact atgccgtttg cgttctgtac aagagagaag aaatggtgtg agtttgcaga 60
gcctgttgat ggcgaatcaa caaagtttct tcaagaacta gccaagaatt ataacatggt 120
gattgtgaat cctatcctcg aaagagatat ggatcacggt gaagtacttt ggaacacagc 180
tgtgattata gggaacaatg gaaacatcat tggcaaacat aggaaggtta acttgcacta 240
caagtctctt tttgcttctg tcttttctct tgtgagctaa cttgtacttc ttggtttgct 300
agaaccacat accgagggtg ggagatttta acgagagcac gtattacatg gaaggagaca 360
ctggacatcc tgtgtttgag acggtgtttg ggaaaattgc agtcaatata tgttatggaa 420
gacaccatcc tctaaactgg ttagcttttg gtctaaatgg tgctgagatt gtcttcaacc 480
cttcagctac tgttggtgaa ctcagtgaac caatgtggcc tattgaggtt taactcctaa 540
ctccccattt ttcacacata gccggtcctg aaat 574

<210> SEQ ID NO 236
<211> LENGTH: 570
<212> TYPE: DNA
<213> ORGANISM: Brassica napus

<400> SEQUENCE: 236
tcgagaatcc tctacaaacg cacaccttgg acatgctcag aacggatatt aaaatcgaca 60
aaaccgccgc accagtcatg aactggcatt ggtttctttg tgtcttcccc atttttaaca 120
gcggaaacac acctcatgaa catgttacga ttcactctgc tgtgtacaag cagagctcgt 180
aaacctgtcc tcgcagctag ttgactcatg actcgataca cacactcgtt tcagatcata 240
tggtctaatg gatttggata ttattcactt ctcggtaagt cttgcagatg ttaggagaaa 300
ggagaaaatg tgacagcagc tgtgttcgcg gcaagtgctg ctaagtacac gtggttcgag 360
tctaaccgtt gtttcatact aaaaatattt cttctaacgg tcgtgatttg atcatttgag 420
tagtgcaagc aagcgtaggt gaatacacta accagggtgc ttaagtgggg tgcttaataa 480

-continued

```
tttttggatt taaaacaaaa aaaaatatcc taaaaaataa aaaatgctac ttgaggggta    540

cttaattaag ctgtcgaata agtggtgctt                                     570


<210> SEQ ID NO 237
<211> LENGTH: 288
<212> TYPE: DNA
<213> ORGANISM: Brassica napus

<400> SEQUENCE: 237

cagaacacag ttctatgaca ctgtcgatag taacatcctc tgcaagtacc aaagagatag     60

caaatgaaac tatgtaaaca aatcaaaatt ctaaatttct ccatcacaag gacctacaga    120

atagagttat cataacattt tctgtaaata tttccatcaa aatgactaga gaacagagtt    180

cttataacat tatctgtaaa tgttccaaca aaaccactac atagcagagt tcttataaca    240

ttgtctgtaa atgtccaatc aaaaccacta cagaacaaag ctcctata                 288
```

*BRASSICA OGURA* RESTORER LINES WITH SHORTENED *RAPHANUS* FRAGMENT (SRF)

CROSS-REFERENCE

This application is a Divisional Application of U.S. application Ser. No. 12/366,155, filed Feb. 5, 2009, now U.S. Pat. No. 8,466,347, which claims the benefit of U.S. Provisional Application No. 61/026,604, filed Feb. 6, 2008 and U.S. Provisional Application No. 61/054,857 filed May 21, 2008, both of which are incorporated herein by reference.

FIELD OF THE INVENTION

The invention relates to new *Brassica* lines having a shortened *Raphanus* fragment which includes the fertility restorer gene for *Ogura* cytoplasmic male sterility. The invention also relates to a new breeding method to shorten an exotic insertion comprising a gene of interest in any plant.

BACKGROUND OF THE INVENTION

Oilseed from *Brassica* plants is an increasingly important crop. As a source of vegetable oil, it presently ranks behind only soybeans and palm in commercial market volume. The oil is used for many purposes such as salad oil and cooking oil. Upon extraction of the oil, the meal is used as a feed source.

In its original form, *Brassica* seed, known as rapeseed, was harmful to humans due to its relatively high level of erucic acid in the oil and high level of glucosinolates in the meal. Erucic acid is commonly present in native cultivars in concentrations of 30 to 50 percent by weight based upon the total fatty acid content. Glucosinolates are undesirable in *Brassica* seeds since they can lead to the production of anti-nutritional breakdown products upon enzymatic cleavage during oil extraction and digestion. The erucic acid problem was overcome when plant scientists identified a germplasm source of low erucic acid rapeseed oil (Stefansson, “The Development of Improved Rapeseed Cultivars.” (Chapter 6) in “High and Low Erucic Acid Rapeseed Oils” edited by John K. G. Kramer, Frank D. Sauer. and Wallace J. Pigden. Academic Press Canada, Toronto (1983)). More recently, plant scientists have focused their efforts on reducing the total glucosinolate content to levels less than 20 μmol/gram of whole seeds at 8.5% moisture. This can be determined by nuclear resonance imaging (NRI) or by high performance liquid chromatography (HPLC) (International Organization for Standardization, reference number ISO 91671:1992).

Particularly attractive to plant scientists were so-called “double-low” varieties: those varieties low in erucic acid in the oil and low in glucosinolates in the solid meal remaining after oil extraction (i.e., an erucic acid content of less than 2 percent by weight based upon the total fatty acid content, and a glucosinolate content of less than 30 μmol/gram of the oil-free meal). These higher quality forms of rape, first developed in Canada, are known as canola.

In addition, plant scientists have attempted to improve the fatty acid profile for rapeseed oil (Robbelen, “Changes and Limitations of Breeding for Improved Polyenic Fatty Acids Content in Rapeseed.” (Chapter 10) in “Biotechnology for the Oils and Fats Industry” edited by Colin Ratledge, Peter Dawson and James Rattray, American Oil Chemists’ Society, (1984); Ratledge, Colin, Dawson, Peter and Rattray, James, (1984) Biotechnology for the Oils and Fats Industry. American Oil Chemists’ Society, Champaign; 328 pp; Robbelen, and Nitsch. Genetical and Physiological Investigations on Mutants for Polyenic Fatty Acids in Rapeseed, *Brassica napus* L. Z. Planzenzuchta., 75:93-105, (1975); Rako and McGregor. “Opportunities and Problems in Modification of Levels of Rapeseed C18 Unsaturated Fatty Acids.” *J. Am. Oil Chem. Soc.* (1973) 50(10):400-403). These references are representative of those attempts.

Currently, both open pollinated varieties and hybrids of *Brassica* are grown. In developing improved *Brassica* hybrids, breeders can utilize different pollination control systems, such as self incompatible (SI), cytoplasmic male sterile (CMS) and nuclear male sterile (NMS) *Brassica* plants as the female parent. In hybrid crop breeding plant breeders exploit the phenomenon of heterosis or hybrid vigor which results in higher crop yields (grain or biomass) from the combination or hybridization of a male and a female line. Using these plants, breeders are attempting to improve the efficiency of seed production and the quality of the F1 hybrids and to reduce the breeding costs. When hybridisation is conducted without using SI, CMS or NMS plants in a two-way cross, it is more difficult to obtain and isolate the desired traits in the progeny (F1 generation) because the parents are capable of undergoing both cross-pollination and self-pollination. If one of the parents is a SI, CMS or NMS plant that is incapable of producing pollen, only cross pollination will occur. By eliminating the pollen of one parental variety in a two-way cross, a plant breeder is assured of obtaining hybrid seed of uniform quality, provided that the parents are of uniform quality and the breeder conducts a single cross.

In one instance, production of F1 hybrids includes crossing a CMS *Brassica* female parent, with a pollen producing male *Brassica* parent. To reproduce effectively, however, the male parent of the F1 hybrid must have a fertility restorer gene (Rf gene). The presence of an Rf gene means that the F1 generation will not be completely or partially sterile, so that either self-pollination or cross pollination may occur. Self pollination of the F1 generation is desirable to ensure the F1 plants produce an excellent yield for the grower. Self pollination of the F1 generation is also desirable to ensure that a desired trait is heritable and stable.

One type of *Brassica* plant which is cytoplasmic male sterile and is used in breeding is *Ogura* (OGU) cytoplasmic male sterile (Pellan-Delourme, et al., (1987) Male fertility restoration in *Brassica napus* with radish cytoplasmic male sterility Proc. 7th Int. Rapeseed Conf., Poznan, Poland, 199-203). A fertility restorer for *Ogura* cytoplasmic male sterile plants has been transferred from *Raphanus sativus* (radish) to *Brassica* by Institut National de Recherche Agricole (INRA) in Rennes, France (Pelletier and Primard, (1987) “Molecular, Phenotypic and Genetic Characterization of Mitochondrial Recombinants in Rapeseed.” Proc. 7th Int Rapeseed Conf., Poznau, Poland 113-118). The restorer gene, Rfl originating from radish, is described in WO 92/05251 and in Delourme, et al., (1991) “Radish Cytoplasmic Male Sterility in Rapeseed: Breeding Restorer Lines with a Good Female Fertility.” Proc 8th Int. Rapeseed Conf., Saskatoon, Canada. 1506-1510.

However, when the *Ogura Raphanus* restorer gene was transferred from radish to *Brassica*, a large segment of the *Raphanus* genome was introgressed into *Brassica* as well. This large *Raphanus* genomic fragment carried many undesirable traits, as well as the restorer gene. For example, the early restorer germplasm was inadequate in that restorer inbreds and hybrids carrying this large *Raphanus* fragment had elevated glucosinolate levels and the restorer was associated with a decrease in seed set—the number of ovules per silique (Pellan-Delourme and Renard, (1988) “Cytoplasmic male sterility in rapeseed (*Brassica napus* L.): Female fertility of restored rapeseed with "*Ogura*" and cybrids cytoplasms", *Genome* 30:234-238; Delourme, et al., (1994), "Identification of RAPD Markers Linked to a Fertility Restorer Gene for the *Ogura* Radish Cytoplasmic Male Sterility of Rapeseed (*Brassica napus* L.)", *Theor. Appl. Gener.* 88:741-748). In the case of hybrids, the glucosinolate levels were elevated even when the female parent had reduced glucosinolate content. These levels, typically more than 30 μmol/gram of oil-free meal, exceeded the levels of glucosinolates allowable for seed registration by most regulatory authorities in the world. Thus, the early restorer germplasm could be used for research purposes, but not to develop canola-quality commercial hybrid varieties directly.

INRA outlined the difficulties associated with obtaining restorer lines with low glucosinolate levels for *Ogura* cytoplasmic sterility (Delourme, et al., (1994) "Identification of RAPD Markers Linked to a Fertility Restorer Gene for the *Ogura* Radish Cytoplasmic Male Sterility of Rapeseed (*Brassica napus* L.)", *Theor. Appl. Gener.* 88:741-748; Delourme, et al., (1995) "Breeding Double Low Restorer Lines in Radish Cytoplasmic Male Sterility of Rapeseed (*Brassica Napus* L.)", Proc. 9th Int. Rapeseed Conf., Cambridge, England). INRA indicated that these difficulties were due to the linkage between male fertility restoration and glucosinolate content in its breeding material. INRA suggested that more radish genetic information needed to be eliminated in its restorer lines (Delourme, et al., (1995) "Breeding Double Low Restorer Lines in Radish Cytoplasmic Male Sterility of Rapeseed (*Brassica Napus* L.)", Proc. 9th Int. Rapeseed Conf., Cambridge, England). Although improvements were made to restorers during the early years, isozyme studies performed on the restorer lines indicated that large segments of radish genetic information still remained around the restorer gene (Delourme, et al., (1994) "Identification of RAPD Markers Linked to a Fertility Restorer Gene for the *Ogura* Radish Cytoplasmic Male Sterility of Rapeseed (*Brassica napus* L.)" *Theor. Appl. Gener.* 88:741-748).

INRA attempted to develop a restorer having decreased glucosinolate levels. It reported a heterozygous restorer with about 15 μmol per gram (Delourme, et al., (1995) "Breeding Double Low Restorer Lines in Radish Cytoplasmic Male Sterility of Rapeseed (*Brassica Napus* L.)", Proc. 9th Int. Rapeseed Conf., Cambridge, England). However, (i) this restorer was heterozygous (Rfrf) not homozygous (RfRf) for the restorer gene, (ii) this restorer was a single hybrid plant rather than an inbred line, (iii) there was only a single data point suggesting that this restorer had a low glucosinolate level rather than multiple data points to support a low glucosinolate level, (iv) there was no data to demonstrate whether the low glucosinolate trait was passed on to the progeny of the restorer, and (v) the restorer was selected and evaluated in a single environment—i.e. the low glucosinolate trait was not demonstrated to be stable in successive generations in field trials. Accordingly, the original *Brassica Ogura* restorer lines were not suitable for commercial use. For the purposes of this disclosure, this material is referred to as the "original" *Brassica* restorer lines.

Improved restorer lines were produced by Charne, et al., (1998) WO 98/27806 "Oilseed *Brassica* Containing an improved fertility restorer gene for *Ogura* cytoplasmic male sterility." The improved restorer had a homozygous (fixed) restorer gene (RfRf) for *Ogura* cytoplasmic male sterility and the oilseeds were low in glucosinolates. Since the restorer was homozygous (RfRf), it could be used to develop restorer inbreds or, as male inbreds, in making single cross hybrid combinations for commercial product development. The glucosinolate levels were below those set out in standards for canola in various countries and breeders could use the improved restorer to produce *Brassica* inbreds and hybrids having oilseeds with low glucosinolate levels. This was a benefit to farmers, who could then plant *Brassica* hybrids which, following pollination, yielded oilseeds having low glucosinolate levels. This breeding effort removed approximately two thirds of the original *Raphanus* fragment. This estimate is based on the loss of 10 of 14 RFLP, AFLP and SCAR markers (WO98/56948 Tulsieram, et al., 1998-12-17). However, the *Raphanus* fragment in this material is still unnecessarily large. For the purposes of this disclosure, this material is referred to as the "first phase recombinant" *Brassica* restorer lines or germplasm.

Despite the improvement in the "first phase recombinant" restorer germplasm, it is still associated with deleterious agronomic performance. These deleterious traits may result from genes within this *Raphanus* fragment unrelated to fertility. Practically, only the restorer gene in the *Raphanus* fragment is required for the canola CMS pollination system. Therefore, the shorter the *Raphanus* fragment in a restorer line, the better the restorer line is expected to perform.

The *Ogura* restorer gene has been isolated and cloned by DNA LandMarks Inc./McGill University (US Patent Application Publication Number 2003/0126646A1, WO 03/006622A2), Mitsubishi (US Patent Application Publication Nubmer 2004/0117868A1) and INRA (WO 2004/039988A1). The gene can be used to transform *Brassica* plants.

Others have tried to produce restorer lines with a shortened *Raphanus* fragment. For example, Institut National de la Recherche (INRA) developed a line with a shortened *Raphanus* fragment by crossing a restorer line, "R211", which had a deletion of the Pgi-2 allele and crossing it with a double low *B. napus* line, Drakkar. The progeny plants were irradiated before meiosis with gamma irradiation to induce recombination. This resulted in one progeny plant, "R2000", in which the Pgi-2 gene from *Brassica oleracea* was recombined (WO 2005/002324 and *Theor. Appl. Genet* (2005) 111:736-746). However, the *Raphanus* fragment in R2000 is larger than that of the first phase recombinant restorer material developed by the Applicant and described above.

Another example, WO 05074671 in the name of Syngenta describes a shortened *Raphanus* fragment in their BLR1 recombination event. The BLR1 recombination event was produced solely by crossing and selection, followed by screening with molecular markers; no mutagenesis was used. However, the *Raphanus* fragment can be shortened further.

SUMMARY OF THE INVENTION

An aspect of the invention is to provide a *Brassica* plant comprising a fertility gene for *Ogura* cytoplasmic male sterility, wherein the fertility gene is on a *Raphanus* fragment introgressed from *Raphanus sativa*, and the *Raphanus* fragment lacks a marker selected from the group consisting of RMA01, RMA02, RMA03, RMA04, RMA05, RMA06, RMA07, RMA08, RMA09, RMA10, RMC24, OPC2, RMC25, RMC26, RMC27, RMC28, RMC29, RMC30, RMC31, RMC32 and RMC33. The *Brassica* plant can lack the OPC2 marker in the *Raphanus* fragment.

Another aspect of the invention is to provide a *Brassica* plant comprising a fertility gene for *Ogura* cytoplasmic male sterility, wherein the fertility gene is on a *Raphanus* fragment introgressed from *Raphanus sativa*, and the *Raphanus* fragment (i) lacks a marker selected from the group consisting of RMA01, RMA02, RMA03, RMA04, RMA05, RMA06, RMA07, RMA08, RMA09, RMA10, RMC24, OPC2, RMC25, RMC26, RMC27, RMC28, RMC29, RMC30, RMC31, RMC32 and RMC33, and (ii) comprises a molecular marker selected from the group consisting of RMB01, E35M62, RMB02, RMB03, RMB04, RMB05, RMB06, RMB07, RMB08, RMB09, RMB10, OPF10, RMB11, RMB12, RMC01, RMC02, RMC03, E38M60, RMC04, RMC05, RMC06, RMC07, RMC08, RMC17, RMC18, RMC19, RMC20, RMC21, RMC22 and RMC23. The *Brassica* plant can be designated R1439, representative seed of which have been deposited under NCIMB Accession Number 41510, or a descendent or a plant produced by crossing R1439 with a second plant. The progeny or descendent plant of this *Brassica* plant can comprise a *Raphanus* fragment which lacks a marker selected from the group consisting of RMA01, RMA02, RMA03, RMA04, RMA05, RMA06, RMA07, RMA08, RMA09, RMA10, RMC09, RMC10, RMC11, RMC12, RMC13, RMC14, RMC15, RMC16, RMC24, OPC2, RMC25, RMC26, RMC27, RMC28, RMC29, RMC30, RMC31, RMC32 and RMC33.

Another aspect of the invention is to provide a *Brassica* plant comprising a fertility gene for *Ogura* cytoplasmic male sterility, wherein the fertility gene is on a *Raphanus* fragment introgressed from *Raphanus sativa*, and the *Raphanus* fragment (i) lacks a marker selected from the group consisting of RMA01, RMA02, RMA03, RMA04, RMA05, RMA06, RMA07, RMA08, RMA09, RMA10, RMC24, OPC2, RMC25, RMC26, RMC27, RMC28, RMC29, RMC30, RMC31, RMC32 and RMC33, and (ii) comprises a molecular marker selected from the group consisting of RMB01, E35M62, RMB02, RMB03, RMB04, RMB05, RMB06, RMB07, RMB08, RMB09, RMB10, OPF10, RMB11, RMB12, RMC01, RMC02, RMC03, E38M60, RMC04, RMC05, RMC06, RMC07, RMC08, RMC09, RMC10, RMC11, RMC12, RMC13, RMC14, RMC15, RMC16, RMC17, RMC18, RMC19, RMC20, RMC21, RMC22 AND RMC23. The *Brassica* plant can be designated R1815, representative seed of which have been deposited under NCIMB Accession Number 41511, or a descendent or a plant produced by crossing R1815 with a second plant. The progeny or descendent plant can comprise a *Raphanus* fragment which lacks a marker selected from the group consisting of RMA01, RMA02, RMA03, RMA04, RMA05, RMA06, RMA07, RMA08, RMA09, RMA10, RMC24, OPC2, RMC25, RMC26, RMC27, RMC28, RMC29, RMC30, RMC31, RMC32 and RMC33.

Another aspect of the invention is to provide a *Brassica* plant comprising a fertility gene for *Ogura* cytoplasmic male sterility, wherein the fertility gene is on a *Raphanus* fragment introgressed from *Raphanus sativa*, and the *Raphanus* fragment (i) lacks a marker selected from the group consisting of RMA01, RMA02, RMA03, RMA04, RMA05, RMA06, RMA07, RMA08, RMA09, RMA10, RMC24, OPC2, RMC25, RMC26, RMC27, RMC28, RMC29, RMC30, RMC31, RMC32 and RMC33, and (ii) comprises a molecular marker selected from the group consisting of RMB01, E35M62, RMB02, RMB03, RMB04, RMB05, RMB06, RMB07, RMB08, RMB09, RMB10, OPF10, RMB11, RMB12, RMC01, RMC02, RMC03, E38M60, RMC04, RMC05, RMC06, RMC07, RMC08, RMC09, RMC10, RMC11, RMC12, RMC13, RMC14, RMC15, and RMC16. The *Brassica* plant can be designated R1931, representative seed of which have been deposited under NCIMB Accession Number 41512, or a descendent or a plant produced by crossing R1931 with a second plant. The progeny or descendent plant can comprise a *Raphanus* fragment which lacks a marker selected from the group consisting of RMA01, RMA02, RMA03, RMA04, RMA05, RMA06, RMA07, RMA08, RMA09, RMA10, RMC17, RMC18, RMC19, RMC20, RMC21, RMC22, RMC23, RMC24, OPC2, RMC25, RMC26, RMC27, RMC28, RMC29, RMC30, RMC31, RMC32 and RMC33.

Any of the *Brassica* plants described above can be *Brassica napus, B. rapa* or *B. juncea*. The plants can be inbreds or hybrids.

Another aspect of the invention is to provide a *Brassica* seed from any of the *Brassica* plants described above. Another aspect is to provide a plant cell from any of the plants described above, or parts of the plants described above. The parts can be selected from the group consisting of nucleic acid sequences, tissue, cells, pollen, ovules, roots, leaves, oilseeds, microspores, vegetative parts, whether mature or embryonic.

Another aspect of the invention is to provide an assemblage of crushed *Brassica* seed of any one of the *Brassica* plants described above.

Another aspect of the invention is to provide a use of the seed of any of the *Brassica* plants described above for preparing oil and/or meal.

Another aspect of the invention is to provide a method of producing oil, comprising: (i) crushing seeds produced by the plant line designated R1439, R1815, or R1931 and having NCIMB Accession Number 41510, 41511 and 41512 respectively, or by a descendent of R1439, R1815, or R1931, or by a plant produced by crossing R1439, R1815, or R1931 with a second plant; and (ii) extracting oil from said seeds. The method can further comprise the step of: (i) refining, bleaching and deodorizing said oil.

Another aspect of the invention is to provide use of any of the plants described above for growing a crop.

Another aspect of the invention is to provide a method of growing a *Brassica* plant, comprising: (i) sowing seed designated R1439, R1815, or R1931 and having NCIMB Accession Number 41510, 41511 and 41512 respectively, or seed from a descendent of R1439, R1815, or R1931, or from a plant produced by crossing R1439, R1815, or R1931 with a second plant; and (ii) growing the resultant plant under *Brassica* growing conditions.

Another aspect of the invention is to provide use of any of the plants described above for breeding a *Brassica* line. The breeding can be selected from the group consisting of conventional breeding, pedigree breeding, crossing, self-pollination, doubling haploidy, single seed descent, backcrossing and breeding by genetic transformation.

Another aspect of the invention is to provide a method of breeding a *Brassica* plant having a fertility gene for *Ogura* cytoplasmic male sterility, wherein the fertility gene is on a *Raphanus* fragment introgressed from *Raphanus sativa*, and the *Raphanus* fragment lacks a molecular marker selected from the group consisting of RMA01, RMA02, RMA03, RMA04, RMA05, RMA06, RMA07, RMA08, RMA09, RMA10, RMC24, OPC2, RMC25, RMC26, RMC27, RMC28, RMC29, RMC30, RMC31, RMC32 and RMC33, comprising: (i) crossing any of the plants described above with another *Brassica* plant to produce a first generation progeny plant; (ii) screening the first generation progeny plant for the *Ogura Raphanus* restorer gene; and (iii) optionally repeating steps (i) and (ii). The first generation progeny plant can be an inbred plant. The first generation progeny plant can be a hybrid plant. The progeny plant produced by this method is also provided.

Another aspect of the invention is to provide a method for breeding a new line having a shortened *Raphanus* fragment compared to a *Raphanus* fragment in a first plant, wherein the shortened *Raphanus* fragment in the new line includes an *Ogura* fertility restorer gene, the method comprising: (i)

mutagenizing a first population of the first plant having a *Raphanus* fragment with an *Ogura* fertility restorer gene for cytoplasmic male sterility; (ii) screening the first population for deletions of the *Ogura* fertility restorer gene in the *Raphanus* fragment to identify a second plant with a deletion of the *Ogura* fertility restorer gene in the *Raphanus* fragment; (iii) crossing the second plant having the deletion of *Ogura* restorer gene in the *Raphanus* fragment with the first plant comprising the *Raphanus* fragment with an *Ogura* fertility restorer gene for cytoplasmic male sterility; (iv) identifying a third plant with a shortened *Raphanus* fragment compared to the first plant, wherein the shortened *Raphanus* fragment includes the restorer gene, and (v) breeding the third plant to produce a new line with a shortened *Raphanus* fragment which includes an *Ogura* fertility restorer gene. The first plant can be R1439, R1815 or R1931. The third plant can lack a molecular marker selected from the group consisting of RMA01, RMA02, RMA03, RMA04, RMA05, RMA06, RMA07, RMA08, RMA09, RMA10, RMC24, OPC2, RMC25, RMC26, RMC27, RMC28, RMC29, RMC30, RMC31, RMC32 and RMC33. The new line produced by this method is also provided.

Another aspect of the invention is to provide an isolated nucleic acid comprising the sequence set forth in any of the sequences listed in SEQ ID NO: 1 to SEQ ID NO: 158.

Another aspect of the invention is to provide use of an isolated nucleic acid comprising the sequence set forth in any of the sequences listed in SEQ ID NO: 1 to SEQ ID NO: 158 for molecular marker development.

Another aspect of the invention is to provide use of an isolated nucleic acid comprising the sequence set forth in any of the sequences listed in SEQ ID NO: 1 to SEQ ID NO: 158 as a primer.

Another aspect of the invention is to provide use of the isolated nucleic acid comprising the sequence set forth in any of the sequences listed in SEQ ID NO: 1 to SEQ ID NO: 158 as a probe.

Another aspect of the invention is to provide use of one or more of the sequences of SEQ ID NOS: 1 to 158 to screen a plant to characterize the *Raphanus* fragment.

Another aspect of the invention is to provide a method of screening a plant to characterize the *Raphanus* fragment, comprising; (i) hybridizing at least one primer sequence selected from the group consisting of SEQ ID NO: 1 to SEQ ID NO: 158 to a plant genome; (ii) performing a PCR assay; and (iii) characterizing the *Raphanus* fragment.

Another aspect of the invention is to provide a method of producing a deletion mutant in a genome having a *Raphanus* fragment with an *Ogura* fertility restorer gene, comprising: (i) providing a population of cells, wherein the cells are heterozygous for the *Raphanus* fragment and the cells have an *Ogura* CMS cytoplasm; (ii) mutagenizing the cells to produce mutagenized cells; (iii) producing plants from the mutagenized cells; and (iv) screening the plants for sterility to identify a deleted *Ogura* fertility restorer gene in a deletion mutant wherein the mutagenized *Ogura* gene is not able to restore fertility in a plant having the *Ogura* CMS cytoplasm. The step of mutagenizing the cells can include irradiation. The deletion mutant produced by this method is also provided.

Another aspect of the invention is to provide a method of recombining a *Raphanus* fragment having an *Ogura* restorer gene, comprising: (i) providing a plant having a *Raphanus* fragment with an *Ogura* restorer gene in the nuclear genome; (ii) crossing the plant of (i) with a plant having a *Raphanus* fragment in which an *Ogura* restorer gene has been deleted in the nuclear genome; and (iii) identifying progeny in which the *Raphanus* fragment has been recombined. The plant of (i) can be homozygous for the *Raphanus* fragment with an *Ogura* restorer gene (RfRf) and the plant of (ii) can be homozygous for the *Raphanus* fragment in which the *Ogura* restorer gene has been deleted (RfˆRfˆ), and the progeny from a first progeny population that are heterozygous for the *Raphanus* fragment (Rf Rfˆ) to allow for recombination at an efficient rate of (a) the *Raphanus* fragment with an *Ogura* restorer gene (Rf) and (b) the *Raphanus* fragment in which the *Ogura* restorer gene has been deleted (Rfˆ). The method can further comprise pollinating (a) a plant that does not contain a *Raphanus* fragment (rfrf) and has an *Ogura* CMS cytoplasm with (b) pollen from the progeny plant above that is heterozygous for both the *Raphanus* fragment with an *Ogura* restorer gene and the *Raphanus* fragment without an *Ogura* restorer gene in the nuclear genome (RfRfˆ), to produce a second progeny population that is heterozygous for the *Raphanus* gene in an *Ogura* CMS cytoplasm, wherein the second population comprises approximately 50% of plants with a rfRf genotype, approximately 50% of plants with rfRfˆ genotype and some progeny in which the *Raphanus* fragment has been recombined (rfRf*), and wherein analysis of the *Raphanus* fragment in the second progeny is facilitated because there is no interference in analyzing the *Raphanus* fragment. The second population progeny plants can be screened for fertility prior to analysis. The method can further comprise a step of identifying a plant comprising a homozygous recombined *Raphanus* fragment. The progeny plant having a recombined *Raphanus* fragment produced by this method is also provided.

Another aspect of the invention is to provide a method for shortening an exotic insertion in a first plant wherein the exotic insertion includes a gene of interest, the method comprising: (i) mutagenizing the first plant having the exotic insertion which includes a gene of interest to produce a second plant having a partially deleted exotic insertion lacking the gene of interest; (ii) crossing the second plant with the first plant to produce a first population in which both the exotic insertion from the first plant and the partially deleted exotic insertion from the second plant can recombine; (iii) crossing the plants of the first population with plants that do not have the exotic insertion to produce a second population of plants; and (iv) screening the second population of plants to identify a third plant with a shorter exotic insertion than the exotic insertion in the first plant, wherein the shorter exotic insertion in the third plant includes the gene of interest.

Another aspect of the invention is to provide a method for breeding a new line having an exotic insertion that is shorter than the exotic insertion in a first plant, wherein the exotic insertion includes a gene of interest, the method comprising; (i) mutagenizing the first plant having the exotic insertion which includes a gene of interest to produce a second plant having a partially deleted exotic insertion lacking the gene of interest; (ii) crossing the second plant with the first plant to produce a first population in which both the exotic insertion from the first plant and the partially deleted exotic insertion from the second plant can recombine; (iii) crossing the plants of the first population with plants that do not have the exotic insertion to produce a second population of plants; and (iv) screening the second population of plants to identify a third plant with a shorter exotic insertion than the exotic insertion in the first plant, wherein the shorter exotic insertion in the third plant includes the gene of interest.

The previous two methods can further comprise a step of generating genetic information of a genomic region surrounding and including the exotic insertion. Generating of genetic information can be selected from the group consisting of generating molecular markers, sequence information and a genetic map. The first plant can be heterozygous for the gene of interest when undergoing mutagenesis in step (i). The first plant can be homozygous for the gene of interest when crossed to the second plant in step (ii). The second plant can be homozygous for the partially deleted exotic insertion lacking the gene of interest when crossed to the first plant in step (ii). The methods can further comprise a step after the step (ii) of identifying plants having the exotic insertion from the first plant and the partially deleted exotic insertion from the second plant using the genetic information. The methods can further comprise the step of increasing the seed of step (ii). The methods can further comprise the step of breeding the third plant to generate a commercial line. The exotic insertion can be a *Raphanus* insertion and the gene of interest can be the *Ogura* fertility restorer gene. The exotic insertion can include a gene of interest selected from the group consisting of disease resistance, insect resistance, drought tolerance, heat tolerance, shattering resistance and improved grain quality. The third plant produced by either of the previous two methods is also provided.

Another aspect of the invention is to provide a molecular marker selected from the group consisting of SEQ ID NOS: 159 to 237.

Another aspect of the invention is to provide use of one or more of the sequences of SEQ ID NOS: 159 to 237 to screen a plant to characterize the *Raphanus* fragment.

Another aspect of the invention is to provide a method of characterizing a plant genome having a *Raphanus* fragment comprising an *Ogura* fertility restorer gene, comprising: (i) utilizing a sequence selected from the group consisting of SEQ ID NO:159 to SEQ ID NO:237 to screen the plant genome; and (ii) characterizing the *Raphanus* fragment.

Another aspect of the invention is to provide a combination of markers/primers for characterizing the *Raphanus* fragment comprising a marker selected from the group SEQ ID NOS: 159 to 237.

Another aspect of the invention is to provide a kit for characterizing the *Raphanus* fragment comprising a primer selected from the group consisting of SEQ ID NOS: 1 to 158. The kit can further comprise marker information.

Another aspect of the invention is to provide a *Brassica* plant comprising the recombination event of R1439, R1815 or R1931.

BRIEF DESCRIPTION OF THE DRAWINGS

The invention will now be described in relation to the figures in which:

FIG. 3 shows a crossing diagram for Shortened *Raphanus* Fragment (SRF) development.

FIG. 4 shows a cartoon depicting a general method for shortening an exotic insertion.

DEFINITIONS

CMS: Means cytoplasmic male sterility and is a type of male sterility useful in hybrid seed production.

Contig: Is a contiguous sequence of DNA created by assembling overlapping sequenced fragments of a chromosome. A contig is also a group of clones representing overlapping regions of the genome. The term contig can also be used to denote a chromosome map showing the locations of those regions of a chromosome where contiguous DNA segments overlap. Contig maps are important because they provide the ability to study a complete, and often large, segment of the genome by examining a series of overlapping clones which then provide an unbroken succession of information about that region such as physical size and orientation.

Maintainer line (also known as B-line): A maintainer line is a line that carries native cytoplasm (i.e. non CMS) and the same nuclear genetics as a cytoplasmic male sterile (CMS) line. When crossed to the CMS line it "maintains" the sterility of the progenies of the CMS line. Accordingly, it has essentially the same nuclear genetic information as the CMS line, but is not male sterile. The maintainer line is a fertile plant and it can produce its own fertile progenies.

Figure 1:
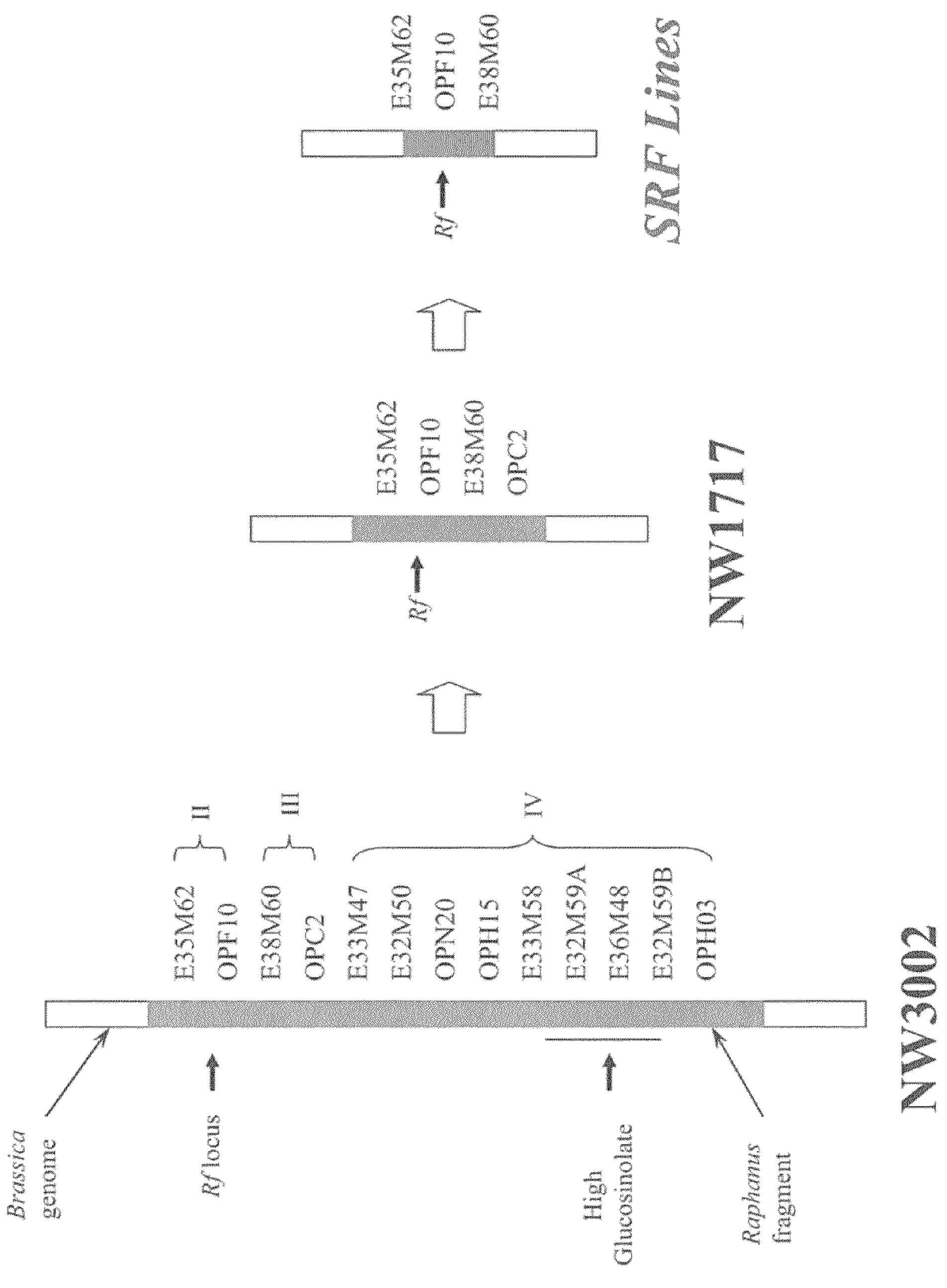
FIG. 1 illustrates the improvements made in (i) the original (NW3002), (ii) first phase recombinant (NW1717) and (iii) new second phase recombinant *Brassica Ogura* restorer lines with shortened *Raphanus* fragment (SRF).

Original restorer lines (also known as original *Brassica Ogura* restorer lines): These lines are the original *Brassica Ogura* restorer lines, and carry the high glucosinolate trait when the restorer gene is present in the homozygous condition. Accordingly, these lines can not be commercialized or used in commercial seed production. An example of these lines is NW3002 as shown in FIG. 1.

First phase recombinant restorer lines or germplasm (also known as first phase recombinant *Brassica Ogura* restorer lines or germplasm): These lines contain a smaller *Raphanus* fragment than the original restorer lines based on marker measurement. These lines do not carry the high glucosinolate trait when the restorer gene is in the homozygous condition. Accordingly, these lines are used commercially. An example of these lines is disclosed in Charne, et al., (1998) WO 98/27806 "Oilseed *Brassica* Containing an improved fertility restorer gene for *Ogura* cytoplasmic male sterility." A further example is NW1717 as shown in FIG. 1. The first phase recombinant restorer lines can be differentiated from the second phase recombinant restorer lines with shortened *Raphanus* fragment by the presence of many markers for example (i) the OPC2 marker as shown in FIG. 1 and (ii) the RMC24 to RMC33 inclusive and RMA01 to RMA10 inclusive markers shown in FIG. 2.

Deletion mutant lines (Rfˆ): These lines contain a mutated *Raphanus* fragment, in which the *Raphanus* restorer gene and other *Raphanus* genes on the fragment have been deleted. For the purposes of the applicant's teaching, these lines are designated Rfˆ. When the mutated *Raphanus* fragment (minus the restorer gene) is in the homozygous condition, the mutant lines are designated RfˆRfˆ and the lines are sterile when their cytoplasm is *Ogura* CMS. When the mutated *Raphanus* fragment is in the heterozygous condition, the lines are designated RfˆRf or Rfˆrf, as is known to those skilled in the art. For example, RfˆRf signifies that one allele comprises the mutated *Raphanus* fragment (minus the restorer gene), and the other allele comprises the first phase recombinant *Raphanus* fragment (with the restorer gene). In the case of RfˆRf, the lines are fertile when their cytoplasm is *Ogura* CMS. Rfˆrf signifies that one allele comprises the mutated *Raphanus* fragment (minus the restorer gene), and the other allele does not contain the *Raphanus* fragment at all. In the case of Rfˆrf, the lines are sterile when their cytoplasm is *Ogura* CMS. These mutant lines were used to generate the lines with the shortened *Raphanus* fragment (SRF), comprising the restorer gene (see below).

Second phase recombinant restorer lines or germplasm (also known as second phase recombinant *Brassica Ogura* restorer lines, second phase recombinant *Brassica Ogura* restorer lines with shortened *Raphanus* fragment (SRF) or Rf*): These lines contain approximately half of the *Raphanus* fragment (as estimated by number of markers lost) found in first phase recombinant restorer lines, and include the *Raphanus* restorer gene. Examples of these lines include R1439, R1815 and R1931 of the present invention, as shown in FIG. 1. For the purposes of the applicant's teaching, these lines are designated Rf*. When the SRF is in the homozygous condition, the lines are designated Rf*Rf*. When the SRF is in the heterozygous condition, the lines are designated Rf*Rf or Rf*rf, wherein Rf*Rf designates a line comprising one allele having a SRF and the other allele having the *Raphanus* fragment from the first phase recombinant lines, and Rf*rf designates a line comprising one allele having a SRF and the other allele not comprising a *Raphanus* fragment at all. All of these SRF lines, whether Rf*Rf*, Rf*Rf or Rf*rf, are fertile when their cytoplasm is *Ogura* CMS.

DESCRIPTION OF THE VARIOUS EMBODIMENTS

The original *Brassica Ogura* restorer lines were developed by INRA by transferring the *Ogura* restorer gene from *Raphanus sativa* to *Brassica napus* (Pelletier, et al., (1987) "Molecular, Phenotypic and Genetic Characterization of Mitochondrial Recombinants in Rapeseed." Proc. 7th Int Rapeseed Conf., Poznau, Poland 113-118). These lines included the gene or genes that conferred the high glucosinolate trait. In FIG. 1 these original lines are exemplified by NW3002.

The first phase recombinant *Brassica Ogura* restorer lines were developed by various institutions, among them the Applicant. The first phase recombinant restorer lines eliminated the gene or genes that confer the high glucosinolate trait. In FIG. 1, these first phase recombinant restorer lines are exemplified by NW1717. However, the first phase recombinant restorer lines still carry a substantial amount of the *Raphanus* genome (FIG. 1). Further, some lines can be associated with undesirable agronomic characteristics. These undesirable traits may result from the genes within the remaining *Raphanus* fragment or from the elimination/disruption of the genes on the *Brassica* chromosome.

The present teaching concerns second phase recombinant *Brassica Ogura* restorer lines with a shortened *Raphanus* fragment (SRF). The second phase recombinant *Brassica Ogura* restorer lines were developed by (i) preparing a physical map using bacterial artificial chromosome (BAC) contigs for the *Raphanus* fragment in the first phase recombinant restorer lines, (data not shown), (ii) mapping the *Raphanus* fragment with high density markers in the first phase recombinant restorer lines, (iii) producing knock-out mutant populations of first phase recombinant *Brassica Ogura* restorer lines, (iv) screening the knock-out mutant populations and identifying mutant lines with various deletions of the first phase recombinant *Raphanus* fragment including *Ogura* restorer gene, (v) crossing the mutant lines with first phase recombinant restorer lines to provide the opportunity for recombination at the *Raphanus* locus and produce second phase recombinant restorer lines with a shortened *Raphanus* fragment (SRF), (vi) identifying new recombinations in lines having the *Ogura* restorer gene with a shortened *Raphanus* fragment (SRF), (vii) characterizing the second phase recombinant restorer lines with a shortened *Raphanus* fragment (SRF), (viii) testing the second phase recombinant restorer lines with SRF for better fertility, embryogenesis and agronomy, and (ix) crossing the new second phase recombinant restorer lines with additional lines to produce commercial lines.

The following Examples are presented as specific illustrations of the present invention. It should be understood, however, that the invention is not limited to the specific details set forth in the Examples.

EXAMPLE 1

Preparing High Density Marker Map of the *Raphanus* Fragment in the First Phase Recombinant *Brassica ogura* Restorer Line, NW1717

Figure 2:
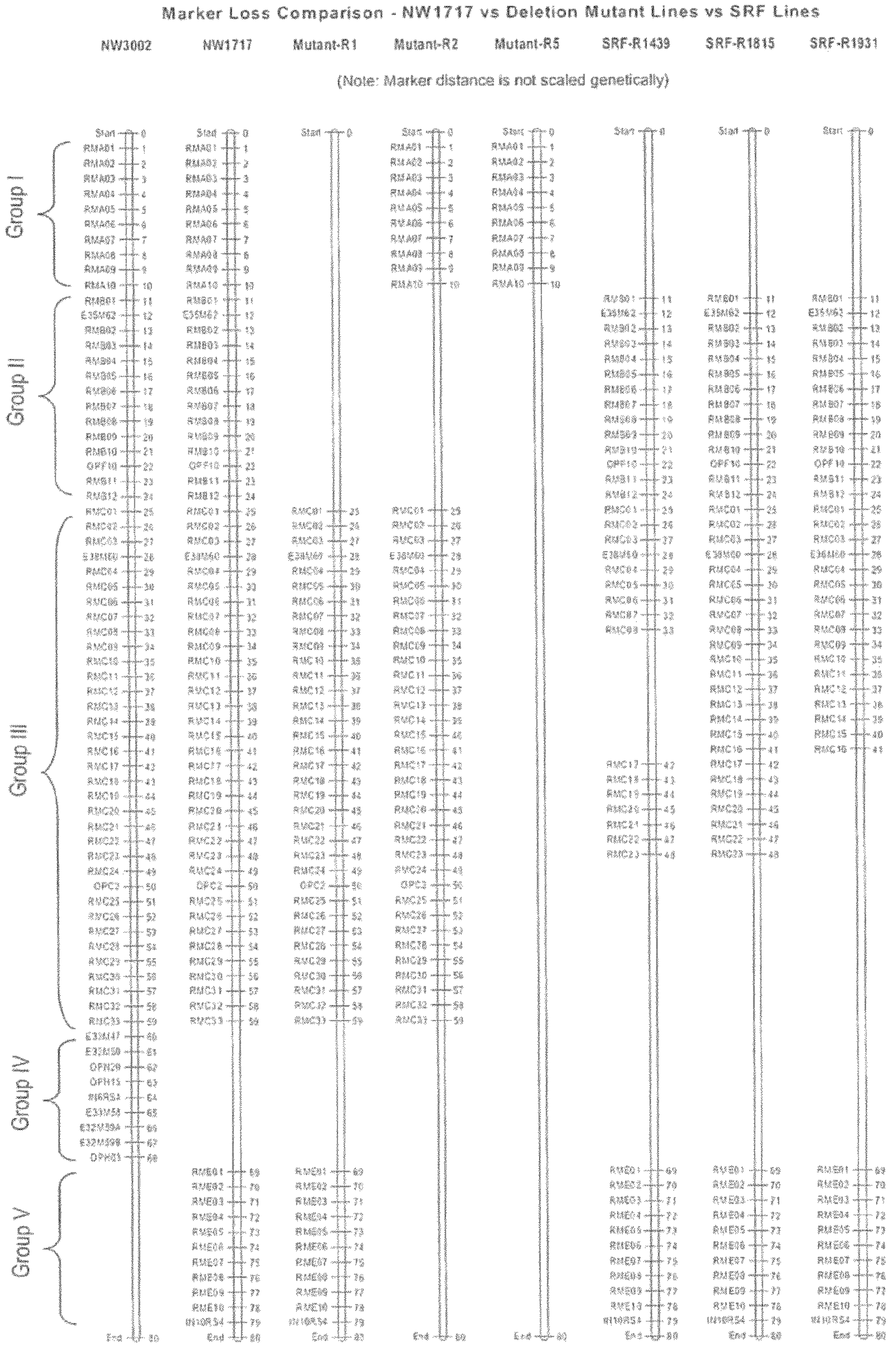
FIG. 2 shows molecular markers lost in mutant lines R1, R2 and R5, and SRF lines R1439, R1815 and R1931, compared to the first phase recombinant *Raphanus* fragment in NW1717 and the original line, NW3002

FIG. 2 shows high density markers on the first phase recombinant *Brassica Ogura* restorer line, NW1717. The marker specificity was investigated with a set of pedigree lines, 6 restorer lines and 6 non restorer lines. Only some of the markers that are specific to the *Ogura* restorer were used to screen the knock-out mutant populations and later the SRF materials of the present invention (see below). The markers are coded and their specifications are listed in Table 1a. The sequence information for the markers is provided in Table 1b.

Table 1a contains key marker information. Columns 1, 2, 3, 11 and 13 list the marker group, the marker name, the size of PCR band, forward primer sequence and reverse primer sequence, respectively. Columns 4 to 10 list the presence or absence of the markers in the first phase recombinant restorer NW1717, the deletion mutant lines R1, R2 and R5, and the SRF lines R1439, R1815 and R1931, respectively (as described in Examples 2-5 below). With the exception of Group IV, all markers are present on the *Raphanus* fragment in the first phase recombinant lines. These markers were used to characterize the original deletion mutants and the shortened *Raphanus* fragment lines (SRF lines) of the present invention.

A kit useful for characterizing the *Raphanus* fragment comprising the primers and/or markers is included within the scope of the invention. For example, a kit can include appropriate primers or probes for detecting marker loci associated with the *Raphanus* fragment and instructions in using the primers or probes for detecting the marker loci and correlating the loci with size of the *Raphanus* fragment present. The kits can further include materials for packaging the probes, primers or instructions, controls such as control amplification reactions that include probes, primers or template nucleic acids for amplifications, molecular size markers, or the like. The kits can also include markers, marker sequence information, physical sequential order information, and expected PCR band size.

EXAMPLE 2

Producing Knock-Out Mutant Populations of the First Phase Recombinant *Brassica ogura* Restorer Line, 00SNH09984

Seed from the $F_1$ line, 00SNH09984, which comprises the CMS cytoplasm and is heterozygous (Rfrf) for the *Ogura* restorer gene, was irradiated in the KFKI Atomic Energy Research Institute (AERI), Hungary. Hybrid seed (i.e., wherein the *Ogura* restorer gene is in the heterozygous state) was chosen for mutagenesis (i.e., irradiation treatment) because hybrid seed has only one copy of the restorer gene (i.e., it is heterozygous for the restorer gene) and therefore there is a higher probability that the mutation of the restorer gene will produce a phenotypic mutant population than homozygous seed which has two identical copies of the restorer gene. In addition, it is more efficient to screen the M0 mutagenized heterozygous population than a mutagenized homozygous population since knock-out mutants can be identified at the current generation (M0) in the heterozygous condition whereas mutants of homozygous seed would need to be identified at M1 or M2 generations if only one of the two gene copies was knocked out. Three groups of 500 g of seed were irradiated with the following dosages 30Gy, 60Gy, and 90Gy. Another 500 g untreated seeds served as control. All treatments were performed with the standard protocol as follows:

Seed mutagenesis was carried out at the Biological Irradiation Facility (BIF) of the Budapest Research Reactor (BRR) located in the Budapest Neutron Center (BNC) and operated by the KFKI Atomic Energy Research Institute (AERI). In general, for seed irradiation with fast neutrons the filter/absorber arrangement number 1A was used. The order of filters starting at the core towards the irradiation cavity was:

Internal: 143.6 mm Al+18 mm Pb+15 mm Al
External inside the borated water collimator: no external filter in front of the sample
Beam stop behind the sample: 30 mm Fe+45 mm Pb+8 mm Al+20 mm $B_4C$ The samples were irradiated inside a Cd capsule with a wall thickness of 2 mm. The irradiation temperature was less than 30° C., at normal air pressure and the humidity was less than 60%. The samples were rotated at 16 revolutions/minute. The samples were usually re-packed to avoid surface contamination and the activation of the original holder/bag. The nominal neutron dose rate (water kerma~absorbed dose in water) at 10.2 MW was 6.93 mGy/s.

During the irradiation there was a real time dose monitoring and the irradiation was terminated when the required dose was delivered.

EXAMPLE 3

Screening Knock-Out Mutant Populations for Deletions in the *Raphanus* Fragment

Treated seed and the untreated control were planted in a one acre licensed field in Canada, in May 2001 as described in Table 2. "PNT" refers to "Plant with Novel Trait". In addition, the corresponding maintainer B line, 96DHS-60, was planted twice as a control, as shown in the planting map as described in Table 3.

TABLE 2

Details of the mutagenized seed in the field trial

| | |
|---|---|
| Crop and recipient line | *Brassica napus* |
| Purpose of trial | Screening male sterile mutant |
| Containment method | 200 meter isolation |
| Location of trials | Ontario, Canada |
| Number of PNT plots/site | 4,000 rows, about one acre |
| Number of plants/site | 250,000 seeds Approx. |
| Proposed harvest dates | September 2001 |
| Treatments during growing season | None |

TABLE 3

Planting map of mutagenized seed field trial

| | Row | Material | Planting Date |
|---|---|---|---|
| 40.00 m | 1.45 m 1 × 4 | 1st planting B line (96DHS-60) | 9 May 2001 |
| | 8.70 m 6 × 4 | rm-30 Gy (00SNH09984-30 Gy) | 9 May 2001 |

TABLE 3-continued

Planting map of mutagenized seed field trial

| | Row | Material | Planting Date |
|---|---|---|---|
| | 8.70 m 6 × 4 | rm-60 Gy (00SNH09984-60 Gy) | 9 May 2001 |
| | 8.70 m 6 × 4 | rm-90 Gy (00SNH09984-90 Gy) | 9 May 2001 |
| | 1.45 m 1 × 4 | 1st planting B line (96DHS-60) | 9 May 2001 |
| | 1.45 m 1 × 4 | 2nd planting B line (96DHS-60) | 18 May 2001 |
| | 1.45 m | Pathway | |
| | 2.90 m 2 × 4 | control (untreated 00SNH09984) | 9 May 2001 |
| 100.00 m | | | |

An estimate of the total number of plants was calculated by sample counting. At flowering, the plants were observed and sterile plants were identified visually. 1415 sterile plants were identified in the treated populations as summarized in Table 4. 104 sterile plants were also observed in the control (which probably resulted from seed impurity), which represents 0.52% of the total control plants, lower than the treated seeds in which up to 0.95% of the plants were sterile. A sterile plant from the mutagenized population could indicate that a mutation occurred on the *Raphanus* fragment such that the restorer gene was deleted or mutated. The sterile plants were labeled and all open flowers were removed. The remaining buds were bagged to ensure no stray pollen could pollinate them. In addition, all fertile plants around the identified sterile mutant plant were destroyed. Young leaves and tissues were collected from all sterile plants. The sterile mutants were pollinated with pollen from the B-line. Seed from the mutant plants was harvested.

TABLE 4

Results of seed mutagenesis screening

| Treatment | 30 Gy | 60 Gy | 90 Gy | Control |
|---|---|---|---|---|
| Total Plant | 64,307 | 61,713 | 45,029 | 19,989 |
| Sterile Plant | 614 | 558 | 243 | 104 |
| Sterile/total (%) | 0.95 | 0.90 | 0.54 | 0.52 |

EXAMPLE 4

Identifying Mutants with Various Deletions in the *Raphanus* Fragment of the First Phase Recombinant *Raphanus* Line The leaf samples from the sterile plants identified as mutants in the field were lyophilized and ground. Genomic DNA was extracted. Methods of DNA extraction are known to those skilled in the art.

The 1415 mutant samples were characterized by performing PCR with a set of representative markers and characterizing which markers were retained and which were lost. The markers consisted of 6 PCR markers. One marker (OPC2) is known to those skilled in the art, while the other 5 markers (RMA07, RMB04, RMB12, RMC32 and RME08) are described here. Each of 6 markers represents a different region of the genomic fragment from the first phase recombinant *Raphanus* lines. All markers are located within the *Raphanus* fragment of the first phase recombinant *Raphanus* lines, except RME08, which is located in the *napus* genome adjacent to the *Raphanus* fragment. Those samples that retained at least one of the Rf markers were kept for further analysis, eliminating false sterile mutants (A-line contamination in hybrid seed). Based on the PCR results, 111 of the 1415 samples were positive for at least one marker. The M1 (second generation mutant) seeds of these 111 sterile plants (crossed with B line) were planted in the greenhouse and the sterility phenotype was confirmed. Leaf tissues were collected and analyzed by PCR using the 6 markers. Using the combination of the PCR results and phenotype data, seven restorer mutants were identified. Three mutant lines, designated Deletion Mutant R1, Deletion Mutant R2 and Deletion Mutant R5 were analyzed further using additional markers and carried forward.

FIG. 2 shows the characterization of the original mutant lines, designated Deletion Mutant R1, Deletion Mutant R2 and Deletion Mutant R5 in comparison to the first phase recombinant restorer line, NW1717. FIG. 2 lists the markers lost on the mutant lines compared to the markers on the NW1717. As can be seen, significant deletions have occurred in the original mutant lines, including deletion of Group II which comprises the restorer gene (Rf). As these plants are heterozygous for the mutated *Raphanus* fragment, they are designated Rf^rf. These mutant lines (which lost the restorer gene) were crossed with first phase recombinant restorer lines to provide various materials for producing new recombinants as described in Example 5. The new recombinants were used to develop second phase recombinant restorer lines with SRF which included the restorer gene.

EXAMPLE 5

Crossing of Mutant R1, Mutant R2 and Mutant R5 Lines with First Phase Recombinant Restorer Lines to Enhance the Probability of Recombination of the Mutated *Raphanus* Fragment The crossing program is detailed below and all pedigree lines are summarized in Table 5 and FIG. 3. In the column entitled generation, "M" refers to mutant, "F" refers to offspring or "filial generation", "F1" refers to first filial generation (heterozygous), "F2" refers to the second filial generation (segregating), "BC" refers to backcross, "DHS" refers to double haploid seed, and "S" refers to self pollinated seed. Each of 5 representative markers has a different purpose. RMA07, RMB12 and OPC2 represent the marker Group I, II and III, respectively. Y5N is a proprietary marker that targets the non-Rf genome. The CMS marker is also proprietary and confirms the presence of *Ogura* CMS cytoplasm.

(i) October 2001: As discussed above, the sterile mutants (Rf^rf) were pollinated with a maintainer line (rfrf), 96DHS60, to produce seeds that were Rf^rf or rfrf in a *Ogura* CMS cytoplasm. On Table 5 these are designated Rf^1rf, Rf^2rf, and Rf^5rf to distinguish each of the three mutants, R1, R2 and R5. This is shown in generation M1F1 of Table 5.

(ii) 2002: M1F1 seeds (Rf^rf/rfrf) from the three identified mutant lines (Mutant R1, Mutant R2 and Mutant R5) were sown in the greenhouse. Rf^rf plants were identified by screening using selected markers (i.e., RMA01-10 for R2 and R5; RMC01-33 for R1 and R2) and pollinated with first phase (wild-type) recombinant restorer line (RfRf) to produce seeds having genotypes of Rf^Rf and rfRf in CMS cytoplasm. This was done for two reasons: (a) to obtain fertile fixed mutant genotypes with normal cytoplasm after further crossing (shown below), and (b) to dilute the mutant dosage (each crossing diluted by 50%). Once the Rf^rf plants were crossed with the wild-type (the first phase recombinant restorer line), all progenies (Rf^Rf and rfRf) were fertile. This is shown in generation M2F1 of Table 5. An rf-specific marker, Y5N, was used to screen the fertile progenies and to eliminate plants with rfRf genotype. Then the B-line 96DHS60 plants (rfrf) were pollinated with Rf^Rf plants. For every crossing two female plants (in case of each of the 3 mutants) and two male plants (first phase recombinant restorer line, NS4304MC) were used and their seeds were bulked with approximately 200 seeds per bulk. All crossings were done under normal growth room conditions for canola: 16 hour light at 22° C. and 8 hour dark at 18° C. This is shown in generation M3F1 of Table 5.

Producing Homozygous Rf^Rf^ Lines in a Normal (Non-Cms) Cytoplasm:

(iii) As stated above, in 2002, plants grown from the Rf^Rf/rfRf seed were identified by using the rf-specific marker to eliminate rfRf plants. The Rf^Rf plants were crossed to the maintainer line rfrf (as a female) to convert the CMS cytoplasm to a *napus* cytoplasm and produce Rf^rf and Rfrf genotypes in a fertile (non CMS) background. The purpose of converting the background from CMS to non-CMS was to enable self-pollination and develop fixed Rf^Rf^ plants. This is shown in generation M3F1 of Table 5.

(iv) In 2003, plants grown from the Rf^rf seed with *napus* cytoplasm were self-pollinated to produce Rf^Rf^, Rf^rf and rfrf seeds. The pollinations were carried out as stated above. This is shown in generation M3F2 of Table 5.

Crossing Rf^Rf^ Lines with RfRf Lines:

The purpose of these crosses was to provide an enhanced probability of abnormal recombination (also referred to as crossover distortion) between the deleted *Raphanus* fragment of the mutant Rf^ lines and the first phase recombinant *Raphanus* fragment of the Rf lines.

(v) In 2003, the plants grown from the Rf^Rf^ seed with *napus* cytoplasm were crossed to the first phase recombinant RfRf restorer line (as female), NS4304MC, to produce 100% fertile Rf^Rf seed with *Ogura* CMS cytoplasm. This 2-way cross would align Rf^ and Rf chromosomes in a cell and provide the possibility that abnormal chromosomal crossover (also called crossover distortion) would occur at the *Raphanus* fragment locus and recombine the *Raphanus* fragment. Progenies with a shortened *Raphanus* fragment that contained the restorer gene could be identified using high density markers within the *Raphanus* fragment. This is shown in generation M4F1 of Table 5 and FIG. 3.

(vi) In 2004, the Rf^Rf lines from step (v) were crossed to a female CMS line (rfrf), NS2173FC, to produce large populations of Rf^rf and Rfrf in a CMS background. This novel three-way cross (F1 crossing to an unrelated A-line) had superior advantages over F1 self-pollination (F2 population) to generate new recombinations while the Rf^Rf plant is undergoing meiosis. Without being limited to any particular theory, this 3-way cross eliminated the Rf and Rf^ *Raphanus* chromosome interference in identifying the progenies having a newly recombined *Raphanus* fragment, leading to a greater probability of identifying a new shortened *Raphanus* fragment comprising the restorer gene. Our results indicated that by using this approach a recombination rate of approximately 0.1% (1 of 1,000) had occurred. As shown in Table 6, if the same recombination rate occurs in F1 self-pollinated population, 1 of 1,000,000 progenies would be homozygous for new *Raphanus* recombination and could be identified by marker profiling, providing that the male and female gametes have the same recombination locus. If the male and female gametes have different recombination loci, it would be nearly impossible to identify any shortened *Raphanus* recombination in F2 population. If the F3 population is used for screening, the population would be excessively large to analyze, in the order of multi-million plants.

Three large populations, approximately 4,000 seeds each, were produced from each of the three mutant lines, Mutant R1, Mutant R2 and Mutant R5. Theoretically, only the Rfrf progenies would be fertile. Rf^rf plants are sterile and would be discarded. All fertile plants, approximately 2,000 each of three populations, were screened with a set of PCR markers. If crossover or recombination occurred then a few fertile plants would lose some markers but still retain the restorer gene. These plants were identified as Rf*rf with shortened *Raphanus* fragment. This is shown in generation M5F1 of Table 5 and FIG. 3.

TABLE 6

| Efficiency comparison between a novel 3-way cross and self-pollination | | | | | | | | | |
|---|---|---|---|---|---|---|---|---|---|
| Novel 3-way cross (rfrf × RfRf/Rf^Rf^) | | | | | Conventional self-pollination (RfRf/Rf^Rf^ –> F2) | | | | |
| | | Male gamete | | | | | Male gamete | | |
| | | Rf (50%) | Rf^ (50%) | Rf* (0.1%) | | | Rf (50%) | Rf^ (50%) | Rf* (0.1%) |
| Female gamete | rf (100%) | 50%<br>Rfrf<br>fertile | 50%<br>Rf^rf<br>sterile | 0.1%<br>Rf*rf<br>fertile | Female gamete | Rf (50%) | 25%<br>RfRf<br>fertile | 25%<br>RfRf^<br>fertile | 0.05%<br>RfRf*<br>fertile |
| | | | | | | Rf^ (50%) | 25%<br>RfRf^<br>fertile | 25%<br>Rf^Rf^<br>sterile | 0.05%<br>Rf^Rf*<br>fertile |
| | | | | | | Rf* (0.1%) | 0.05%<br>RfRf*<br>fertile | 0.05%<br>Rf^Rf*<br>fertile | 0.0001%<br>Rf*Rf*<br>fertile |
| Efficiency | Fertile progenies (50% population) need screening;<br>Frequency to identify Rf*rf is 1 of 1,000. | | | | Fertile progenies (75% population) need screening;<br>Frequency to identify Rf*Rf* is 1 of 1,000,000. | | | | |

(vii) In 2004, approximately 6,000 rfRf plants were screened with multiple PCR markers. Three second phase recombinant restorer lines with a shortened *Raphanus* fragment, designated R1439, R1815 and R1931, were identified with up to 50% loss of the *Raphanus* fragment compared to the first phase recombinant restorer material, NW1717 (see detail marker profile in FIG. 2). R1815 originated from Mutant R2 crossing population, and R1439 and R1931 originated from Mutant R5 crossing population. These plants comprise a new recombination event, designated R1439, R1815 and R1931 respectively.

(viii) In 2005, and 2006 the three lines were fixed by breeding and doubled haploid production, and designated R1439, R1815 and R1931. This is shown in generations M6F2 and M6DHS1 of Table 5.

(ix) 2005 and 2006 the three SRF lines were also backcrossed 5 times to produce BC0, BC1, BC2, BC3, and BC4 lines. Each backcrossing used four plants of NS1822FC as female and 4 plants of each Rf*rf genotype (i.e., R1439, R1815 and R1931) as male. The seeds were bulked and planted immediately to produce Rf*rf and rfrf plants. The sterile rfrf plants were discarded and only fertile Rf*rf were carried forward to the next generation of backcrossing. In addition to backcrossing, BC2 and BC4 plants were self-pollinated to produce BC2S1 (F2) and BC4S1 (F2) seeds. Then BC2S1 and BC4S1 plants were self-pollinated to produce fixed BC2S2 (F3) and BC4S2 (F3) as breeding material. This is shown in generations M7BC0 to BC4S2 of Table 5, inclusive.

EXAMPLE 6

Characterization of Second Phase Recombinant SRF Lines

Table 7 compares the deletions in the *Raphanus* fragment of the second phase recombinant restorer lines with the *Raphanus* fragment in the first phase recombinant restorer line, NW1717. The *Raphanus* fragment in the second phase recombinant restorer lines is estimated to be about 36% to 49% shorter than the *Raphanus* fragment in the first phase recombinant restorer line, NW1717. This estimation is based on number of markers deleted. For example, in SRF line R1815, 21 of the 59 markers have been lost. Based on the number of markers lost (21/59), approximately 36% of the *Raphanus* fragment has been deleted (64% of the *Raphanus* fragment remains). In the case of SRF line R1439, 29 out of 59 markers have been lost. Based on the number of markers lost (29/59), approximately 49% of the *Raphanus* fragment has been deleted (approximately 51% remains). FIG. 2 shows the markers that have been deleted and the markers that remain in the SRF lines/recombination events, R1439, R1815 and R1931. Physical maps (not in scale) of the SRF lines are found in FIG. 2.

TABLE 7

| Remaining *Raphanus* Fragment in SRF Lines | | | | |
|---|---|---|---|---|
| SRF Lines | R1439 | R1815 | R1931 | NW1717 |
| % of NW1717* | ~51% | ~64% | ~53% | 100% |
| Marker Loss/<br>Total Rf Marker | 29/59 | 21/59 | 28/59 | 0/59 |

*estimated by number of markers lost

The SRF lines are more similar to NW1717 than to the deletion mutants R1, R2 and R5 because they include the *Raphanus* restorer gene. The deletion mutants R1, R2 and R5 were lacking the *Ogura* restorer and were quite different than NW1717. The main function of the deletion mutants was to cause crossover distortion and break down the *Raphanus* fragment in NW1717 to generate the SRF lines. The SRF lines retain fewer undesirable radish genes and are expected to have better agronomic performance.

The third row of Table 7 summarizes the number of markers lost for each line. There are 59 markers on the first phase recombinant restorer line, NW1717. The number of markers lost in the second phase recombinant lines ranges from 21 to 29. The SRF lines contain the restorer gene and they have been tested to confirm that they restore male fertility of *Ogura* CMS lines.

FIG. 1 shows the relationship between the original *Brassica napus* line in which the *Ogura* restorer fragment was introgressed (NW3002), the first phase recombinant commercial line (NW1717) and the second phase recombinant restorer line with a shortened *Raphanus* fragment (SRF lines). As can be seen, significant deletions have occurred on the *Raphanus* fragment. The original lines (represented here by NW3002) contained the restorer locus and the high glucosinolate locus. The first phase recombinant restorer lines which were used commercially (represented by NW1717) contain much smaller *Raphanus* fragment than NW3002. The high glucosinolate locus was deleted in the first phase recombinant restorer lines. The second phase recombinant restorer lines contain much shorter *Raphanus* fragment than NW1717, but still retain the restorer gene. The second phase recombinant restorer lines have better agronomic performance, as will be discussed below. The OPC2 and E38M60 markers can clearly distinguish between the first phase recombinant and the second phase recombinant *Raphanus* fragments. The E38M60 marker is found in NW1717 and in the second phase recombinant restorer lines. The OPC2 marker is found in NW1717, but not in the second phase recombinant restorer lines. Additional markers as shown on FIG. 2 can be used to distinguish the three SRF lines from first phase recombinant lines and from each other. For example, the set of the markers, RMC09 to RMC23 inclusive, can distinguish the three SRF lines from each other. R1439 has lost the DNA sequences which contain many of the markers of Group III and all of the markers of Group I. It is flanked by RMB01 and RMC23, but lacks RMC09 to RMC16 inclusive. R1815 has lost the DNA sequences which contain the markers from RMC24 to RMC33 and all the markers of Group I. It is flanked by RMB01 and RMC23. Finally, R1931 has lost the DNA sequences which contain the markers of Group I and markers RMC17 to RMC23 of Group III. It is flanked by RMB01 and RMC16.

A comparison of the second phase recombinant *Brassica Ogura* restorer lines of the present invention with competitors' lines (INRA R2000, INRA R211 and INRA R113) is shown in Table 8. The new recombined restorer lines produced by the novel breeding method disclosed here have a shorter *Raphanus* fragment than the *Raphanus* fragment of the competitors' lines. The novel breeding method disclosed here which produced these lines proved to be very successful.

TABLE 8

Key Rf Marker Profiling among Selected Ogura Restorer Materials

| Marker Group | Rf Marker | SRF - R1439 | SRF - R1815 | SRF - R1931 | NW1717 | R2000 - INRA | R211 - INRA | R113 - INRA | NW3002 (R40) |
|---|---|---|---|---|---|---|---|---|---|
| I | RMA01 | − | − | − | + | + | + | + | + |
| | RMA02 | − | − | − | + | + | + | + | + |
| | RMA08 | − | − | − | + | + | + | + | + |
| | RMA10 | − | − | − | + | + | + | + | + |
| II | RMB01 | + | + | + | + | + | + | + | + |
| | E35M62 | + | + | + | + | + | + | + | + |
| | RMB02 | + | + | + | + | + | + | + | + |
| | RMB04 | + | + | + | + | + | + | + | + |
| | RMB08 | + | + | + | + | + | + | + | + |
| | RMB10 | + | + | + | + | + | + | + | + |
| | OPF10 | + | + | + | + | + | + | + | + |
| | RMB12 | + | + | + | + | + | + | + | + |
| III | RMC01 | + | + | + | + | + | + | + | + |
| | RMC02 | + | + | + | + | + | + | + | + |
| | E38M60 | + | + | + | + | + | + | + | + |
| | RMC08 | + | + | + | + | + | + | + | + |
| | RMC09 | − | + | + | + | + | + | + | + |
| | RMC11 | − | + | + | + | + | + | + | + |
| | RMC15 | − | + | + | + | + | + | + | + |
| | RMC16 | − | + | + | + | + | + | + | + |
| | RMC17 | + | + | − | + | + | + | + | + |
| | RMC19 | + | + | − | + | + | + | + | + |
| | RMC21 | + | + | − | + | + | + | + | + |
| | RMC23 | + | + | − | + | + | + | + | + |
| | RMC24 | − | − | − | + | + | + | + | + |
| | OPC2 | − | − | − | + | + | + | + | + |
| | RMC25 | − | − | − | + | + | + | + | + |
| | RMC27 | − | − | − | + | + | + | + | + |
| | RMC29 | − | − | − | + | + | + | + | + |
| | RMC31 | − | − | − | + | + | + | + | + |
| | RMC32 | − | − | − | + | + | + | + | + |
| IV | E33M47 | − | − | − | − | + | + | + | + |
| | E32M50 | − | − | − | − | + | + | + | + |
| | OPN20 | − | − | − | − | + | + | + | + |
| | OPH15 | − | − | − | − | + | + | + | + |
| | IN6RS4 | − | − | − | − | + | + | + | + |
| | E33M58 | − | − | − | − | + | + | + | + |
| | E32M59A | − | − | − | − | − | − | + | + |
| | E32M59B | − | − | − | − | − | − | + | + |
| | OPH03 | − | − | − | − | − | − | − | + |

The novel breeding method taught here can be used for purposes other than reducing the size of the *Raphanus* fragment. It can be used whenever an exotic insertion comprising a gene or genes of interest has been introduced into a germplasm and one wishes to reduce the size of the exotic insertion, but preserve the gene or genes of interest. Moreover, the new breeding method is not limited to *Brassica* species, but can be used for any species, including wheat, corn, soybean, alfalfa, and other plants. In many circumstances a breeder may find it useful to introduce exotic insertions into elite germplasm using techniques as is known to those skilled in the art. For example, the exotic insertion can be introduced by crossing, transformation of artificial chromosomes, nucleus injection, protoplast fusion, and other methods as is known to those skilled in the art. For example, insect and disease resistance genes are often transferred via wide crosses to elite plant germplasm. In addition, agronomic traits such as drought resistance, heat tolerance, shattering and grain quality (seed composition) have also been transferred by interspecific crosses.

However, in most cases the breeder will discover that together with the gene or genes of interest, "superfluous" genetic material is introduced that affects other traits. Essentially, there are two problems with the superfluous genetic material. First, the superfluous genetic material may carry undesirable genes. For example, the original *Raphanus* insertion included genes that conferred a high glucosinolate trait. Second, the superfluous genetic material may result in problems with meiosis because the chromosomes cannot align properly due to the exotic insertion. This may lead to fertility problems and less agronomic vigor, as was seen in the original *Raphanus* material. Accordingly, once breeders have introduced exotic insertions into elite germplasm, they then tend to spend years "chipping away" at it to reduce its size, while screening for the gene or genes of interest. Traditionally, this has been done by continuous crossing to elite lines in the hopes that the exotic insertion will be reduced. The problem is, however, that there is no homologous sequence in the elite germplasm to recombine with the exotic insertion, and so this can be time consuming and not efficient.

The novel breeding method described here overcomes this problem by producing a line (i.e. a deletion mutant) which comprises the elite germplasm and the exotic insertion in which the gene or genes of interest have been deleted. This deletion mutant is crossed with the original germplasm containing the exotic insertion. Since the deletion mutant still contains part of the exotic insertion, it can align with the original insertion and induce genetic recombination. Essentially, the new breeding method provides a line which can easily recombine with the original exotic insertion. This new breeding method was described in detail in the examples with regard to reducing the *Raphanus* fragment, but as discussed above, it can be used for any situation in which an exotic insertion into an elite germplasm requires reduction in size. The novel breeding method is summarized by the following steps and shown as a cartoon in FIG. 4. For clarity, the exotic insertion is denoted "E", the exotic deletion is denoted "Eˆ", the recombined shortened exotic insertion is denoted "E*", and the null chromosome (i.e. without the exotic insertion) is denoted "e":

(i) It is very useful to have an understanding of the exotic insertion and the region surrounding the exotic insertion. This can be done by a genetic map, sequence information, a molecular marker map, and/or other methods as is known to those skilled in the art, of the genomic region surrounding and including the exotic insertion. A high density marker map will facilitate the identification of a shorter recombined exotic insertion.

(ii) The next step is to produce deletion mutants preferably in heterozygous lines, wherein the lines are heterozygous for the exotic insertion (Ee)→(Eˆe). Deletion mutants are mutants in which the gene or genes of interest are deleted from the genome, but some of the exotic insertion is still present. By using heterozygous lines, one can identify the deletion mutants more readily than using homozygous lines because the phenotype of the deletion mutants will not be masked by the homologous locus. The deletion mutants can be maintained, stabilized and reconfirmed by crossing with null lines (ee) one or more times.

(iii) The next step is to cross the deletion mutants (Eˆe) with lines that are homozygous for the exotic insertion (EE) to produce (EˆE) and (eE) seed, and subsequently identifying those lines that contain the deletion (EˆE). The identification of (EˆE) can be done by screening the genome using markers identified in step (i). For example, the markers can be specific to the null lines (ee). Alternatively, one can self EˆE and eE and use the progeny segregation to identify EˆE plants in which no ee genotype can be present in their progenies. Optionally, the Eˆe deletion mutants are first self-pollinated (assuming a trait other than fertility) and EˆEˆ plants are selected and crossed with EE, so that all offspring are EˆE.

(iv) Optionally, the (EˆE) plants are increased to obtain sufficient numbers for pollination purposes. This can be done by (a) self pollination of (EˆE) to produce (EˆEˆ), (EˆE) and (EE) seed, followed by (b) cross pollination of (EˆEˆ) with (EE) to produce many (EˆE) plants. In the present invention, this step was done to change the cytoplasm from CMS to normal cytoplasm. If this step is not required, one can move on to Step (v) directly since theoretically only one (EˆE) plant is required.

(v) The next step is to cross (EˆE) with a null line (ee) to create a large F1 population, up to thousands of seeds. During meiosis the exotic insertion in the (EˆE) line undergoes recombination, such that at least some gametes comprise a recombined exotic insertion which includes the gene or genes of interest, but is significantly shorter than E. The shorter recombined exotic insertion is denoted E*. The recombination rate will depend on the plant species, the size of the exotic insertion, the size and character of the deletion mutant, and other factors. The recombination rate for the *Raphanus* fragment was found to be approximately 0.1%. The progenies (Eˆe), (Ee) and (E*e) are screened with molecular markers to identify exotic insertions that have recombined (E*e). By serial backcrossing with a null line (ee), the phenotype of E* is expressed. The phenotype can be verified with measurements depending on the genes or traits of interest. Although not being limited to any theory, a high degree of homology between the exotic insertion and the deletion mutant may lead to a greater probability of crossing over.

By following this new breeding method, a skilled worker can reduce the size of an exotic insertion while maintaining the gene of interest. This can be done with any species and with any exotic insertion as discussed above.

Further, this method can be repeated until the exotic insertion is deleted to an acceptable length. For example, lines containing the shortened fragment (E*E*) can be crossed with the deletion mutants (EˆEˆ) to produce PEA lines. These lines can then be crossed with null lines (ee) lines to allow recombination of the exotic insertion. The progeny (E*e, Eˆe and Ee) can be screened for further reduction of the exotic fragment. E denotes a further reduction in the exotic fragment which retains the gene or genes of interest.

EXAMPLE 7

Continued Backcrossing with Maintainer Line to Produce BC2, BC3, BC4, BC2S2 and BC4S2 Generations, and Convert SRF Lines to Breeding Materials with Normal Maintainer and Restorer Background All backcrossing and self-pollination were done in the greenhouse under the same conditions mentioned above. BC1 seeds were planted and showed normal genetic segregation. Because of mixed genotype (Rf*rf/rfrf), 50% of the BC1 plants were fertile and other 50% plants were sterile. Four fertile BC1 plants (Rf*rf) were selected as male and crossed to a female line (male sterile A-line) NS1822FC, that has the same nucleus as the maintainer line but with a male sterile cytoplasm to produce BC2 seeds. The bulked BC2 seeds were advanced the same way to produce BC3 and BC4 seeds. Each generation of backcrossing showed normal fertility segregation, 50% fertile and 50% sterile (Table 10). The selected fertile BC2 and BC4 plants, Rfrf, were self-pollinated to generate BC2S1 and BC4S1 (F2) seeds, respectively. BC2S1 and BC4S1 seeds were planted and segregation was observed (Table 11). The homozygous BC2S1 and BC4S1 plants were identified and self-pollinated to produce fixed BC2S2 and BC4S2 seeds. Table 5 lists a summary of the pedigree lines leading to the SRF lines. This is shown in generations M6F2 to BC4S2 of Table 5, inclusive. The result of the breeding was the development of three new lines with a homozygous locus comprising a shortened *Raphanus* fragment ($Rf^{1439}Rf^{1439}$, $Rf^{1815}Rf^{1815}$ and $Rf^{1931}Rf^{1931}$).) Table 9 is a summary of the chronological events leading to the development of the SRF restorer lines.

TABLE 9

Chronological Events Leading to Rf Lines with Shortened *Raphanus* Fragment (SRF)

| Year | Activity | Result |
|---|---|---|
| 2000 | Irradiated hybrid seeds in KFKI Atomic Energy Research Institute (AERI), Hungary. | 1.5 kg treated canola seeds |
| 2001 | planted treated seeds and untreated seeds in 1 acre permitted field | 1215 sterile plants from treated population |
| 2001 | DMA isolation and PCR screening with many Rf markers | 3 Rf mutants (R1, R2 & R5) identified |
| 2001 | crossed with maintainer line | 3 Rf mutant seeds (rfRf$^{\wedge}$) with different marker loss |
| 2002 | crossed with wildtype restorer line | Rf$^{\wedge}$Rf seed |
| 2002 | crossed Rf$^{\wedge}$Rf to maintainer line to convert CMS to normal cytoplasm | fertile mutant plants (rfRf$^{\wedge}$) |
| 2003 | selfing rfRf$^{\wedge}$ plant | fixed mutant progeny (Rf$^{\wedge}$Rf$^{\wedge}$) |

TABLE 9-continued

Chronological Events Leading to Rf Lines with Shortened *Raphanus* Fragment (SRF)

| Year | Activity | Result |
|---|---|---|
| 2003 | crossed Rf$^{\wedge}$Rf$^{\wedge}$ to wildtype restorer line | fertile F1 seed (RfRf$^{\wedge}$) |
| 2004 | crossed Rf$^{\wedge}$Rf to female line | large population of F1 seeds (~4,000 each mutant) |
| 2004 | screened ~6,000 rfRf$^{\wedge}$/rfRf plants with multiple Rf markers | 3 SRF lines with various loss of *Raphanus* genome in NW1717 |
| 2005 | fixed 3 rfRf$^{\wedge}$ lines through breeding or DH | Rf$^{\wedge}$Rf$^{\wedge}$ seeds |
| 2005 | Series backcrossing with maintainer line | BC0 and BC1 |
| 2006 | continued backcrossing with maintainer line | BC2, BC3 and BC2S1 |
| 2006 | continue characterization, expand evaluation and incorporate into breeding materials | BC2S2, BC4 and BC4S1 |
| 2007 | continue characterization, expand evaluation and incorporate into breeding materials | BC4S2 and integreting SRF lines into breeding program with elite genetic background |
| 2007 | Field test | agronomic data and quality data |

EXAMPLE 8

Preliminary Data for Improved Fertility Rates in SRF Lines Compared With First Phase Recombinant Lines Preliminary results from greenhouse grown plants indicate that the SRF lines undergo normal Mendelian segregation of the restorer trait and are better able to restore fertility to *Ogura* CMS plants than the first phase restorer lines. Table 10 summarizes the backcrossing data from all backcross generations except BC2 in which the data was not collected. The SRF lines were backcrossed to CMS lines. Details of the experiments can be found above, specifically in Example 7. Backcrossed populations of SRF lines R1439, R1815 and R1931 resulted in fertile progenies of 47%, 45% and 52%, respectively. The data is very close to the theoretical number of 50%. Table 11 summarizes the BC4S1 (F2) segregation of three SRF lines with parallel comparison of the NW1717 source. R1439 and R1815 showed normal F2 segregation. That is, one quarter of the F2 progenies, rfrf, were sterile. Two quarters were heterozygous fertile, rfRf* and one quarter were homozygous fertile, Rf*Rf*. The exception was R1931 which showed higher heterozygous and lower homozygous fertile progenies than the theoretical rate.

TABLE 10

Summary of Backcrossing Data for SRF Lines

| SRF | | | | | Total | Fertile Progeny | | | Sterile Progeny | | |
|---|---|---|---|---|---|---|---|---|---|---|---|
| Line | Gen | Population | Recurrent | Donor | Plant | Plant | % | Genotype | Plant | % | Genotype |
| R1439 | BC0 | 05SM205 | NS1822FC | $rfRf^{1439}$ | 32 | 15 | 47 | $rfRf^{1439}$ | 17 | 53 | rfrf |
| | BC1 | 05SM235 | NS1822FC | $rfRf^{1439}$ | 32 | 17 | 53 | $rfRf^{1439}$ | 15 | 47 | rfrf |
| | BC3 | 06SM399 | NS1822FC | $rfRf^{1439}$ | 20 | 7 | 35 | $rfRf^{1439}$ | 13 | 65 | rfrf |
| | BC4 | 06SM414 | NS1822FC | $rfRf^{1439}$ | 20 | 10 | 50 | $rfRf^{1439}$ | 10 | 50 | rfrf |
| | | | Total | | 104 | 49 | 47 | | 55 | 53 | |
| R1815 | BC0 | 05SM208 | NS1822FC | $rfRf^{1815}$ | 32 | 14 | 44 | $rfRf^{1815}$ | 18 | 56 | rfrf |
| | BC1 | 05SM236 | NS1822FC | $rfRf^{1815}$ | 32 | 19 | 59 | $rfRf^{1815}$ | 13 | 41 | rfrf |

TABLE 10-continued

| Summary of Backcrossing Data for SRF Lines | | | | | | | | | | | | |
|---|---|---|---|---|---|---|---|---|---|---|---|---|
| SRF | | | | | Total | Fertile Progeny | | | Sterile Progeny | | |
| Line | Gen | Population | Recurrent | Donor | Plant | Plant | % | Genotype | Plant | % | Genotype |
| | BC3 | 06SM400 | NS1822FC | $rfRf^{1815}$ | 20 | 8 | 40 | $rfRf^{1815}$ | 12 | 60 | rfrf |
| | BC4 | 06SM415 | NS1822FC | $rfRf^{1815}$ | 20 | 6 | 30 | $rfRf^{1815}$ | 14 | 70 | rfrf |
| | | | Total | | 104 | 47 | 45 | | 57 | 55 | |
| R1931 | BC0 | 05SM209 | NS1822FC | $rfRf^{1931}$ | 32 | 14 | 44 | $rfRf^{1931}$ | 18 | 56 | rfrf |
| | BC1 | 05SM237 | NS1822FC | $rfRf^{1931}$ | 32 | 20 | 63 | $rfRf^{1931}$ | 12 | 38 | rfrf |
| | BC3 | 06SM401 | NS1822FC | $rfRf^{1931}$ | 20 | 9 | 45 | $rfRf^{1931}$ | 11 | 55 | rfrf |
| | BC4 | 06SM416 | NS1822FC | $rfRf^{1931}$ | 20 | 11 | 55 | $rfRf^{1931}$ | 9 | 45 | rfrf |
| | | | Total | | 104 | 54 | 52 | | 50 | 48 | |

TABLE 11

| Summary of BC4S1 (F2) Population Segregation for SRF Lines | | | | | | | | | | |
|---|---|---|---|---|---|---|---|---|---|---|
| | Total | rfrf (Sterile) | | | rfRf* (Fertile) | | | Rf*Rf* (Fertile) | | |
| Rf Source | Plant | Expected | Observed | % | Expected | Observed | % | Expected | Observed | % |
| R1439 | 128 | 32 | 32 | 25% | 64 | 69 | 54% | 32 | 27 | 21% |
| R1815 | 127 | 32 | 34 | 25% | 64 | 67 | 54% | 32 | 26 | 20% |
| R1931 | 127 | 32 | 30 | 24% | 64 | 90 | 71% | 32 | 7 | 6% |
| NW1717 | 127 | 32 | 31 | 24% | 64 | 72 | 57% | 32 | 24 | 19% |

EXAMPLE 9

Preliminary Data for Embryogenesis Using the SRF Lines

F2 populations of three SRF lines were used as donor plants to fix SRF lines through double haploid (DH) production. The spring canola DH protocol used through microspore embryogenesis was detailed in Swanson, Eric B., Chapter 17, p. 159 in Methods in Molecular Biology, vol. 6, Plant Cell and Tissue Culture, Ed. Jeffrey W. Three F2 populations, 05SM194, 05SM197 and 05SM198, were grown in the greenhouse under normal canola growth conditions, 32 plants for each population. Upon flowering, 10 fertile plants were randomly selected as DH donor plants. Fertile plants had two genotypes: rfRf* and Rf*Rf*. The 10 donor plants were not genotyped with molecular markers but should, on average, consist of 3 Rf*Rf* plants (⅓) and 7 rfRf* plants (⅔). The buds from the 10 donor plants were bulked and used as initial microspore source for DH production. The DH progenies were grown in the same green house conditions until flowering. Their phenotype (fertility) was recorded and summarized in Table 12. The fertile progeny have the Rf*Rf* genotype and the sterile progeny have rfrf. A large difference was observed among three SRF lines. R1439 and R1931 had good embryogenesis in DH production, 47% and 38% fertile progenies, respectively, while R1815 had poor embryogenesis, about 1% fertile progenies.

TABLE 12

| Summary of DH Fixing for SRF Lines | | | | | | | | | | |
|---|---|---|---|---|---|---|---|---|---|---|
| SRF | Donor Plant | | | Total | Fertile DH Progeny | | | Sterile DH Progeny | | |
| Line | Generation | Population | Genotype | DH | Plant | % | Genotype | Plant | % | Genotype |
| R1439 | M6F2 | 05SM194 | ⅓ $Rf^{1439}Rf^{1439}$<br>⅔ $rfRf^{1439}$ | 89 | 42 | 47 | $Rf^{1439}Rf^{1439}$ | 47 | 53 | rfrf |
| R1815 | M6F2 | 05SM197 | ⅓ $Rf^{1815}Rf^{1815}$<br>⅔ $rfRf^{1815}$ | 114 | 1 | 1 | $Rf^{1815}Rf^{1815}$ | 113 | 99 | rfrf |
| R1931 | M6F2 | 05SM198 | ⅓ $Rf^{1931}Rf^{1931}$<br>⅔ $rfRf^{1931}$ | 116 | 44 | 38 | $Rf^{1931}Rf^{1931}$ | 72 | 62 | rfrf |

EXAMPLE 10

First Year Data for Agronomic and Quality Traits of the SRF Line

In 2007, F3 progeny from three sets of seven crosses, each cross having respectively R1439, R1815 or R1931 as one of the SRF parents and a different breeding line or commercial variety as a second parent, were planted in a restorer breeding nursery at Belfountain, Ontario. The row numbers 1, 20, 40, 60, etc. were planted with 46A65—a commercial canola variety selected for quality purposes. Approximately 100 seeds of each F3 and 46A65 check were planted in rows 3 meters long and spaced 50 cm apart. At physiological maturity, the F3 lines in each cross were visually selected for superior vigor, uniformity, early maturity, and the selected lines were later harvested with 15 grams of open pollinated seed samples for quality analysis. Each quality check row was also harvested with the same amount of seed for quality comparison. Selection for oil, protein and total glucosinolates was performed by comparing each SRF line to the two nearest check rows on each side. The F3 lines having higher oil, higher protein and lower total glucosinolates than the two nearest checks were advanced in the breeding program. The results of quality analysis are summarized in Table 13. Based on the total average of all the harvested lines from seven crosses, the SRF lines had lower total glucosinolates than 46A65, the commercial check.

TABLE 13

Results of quality analysis on seed samples collected from 2007 breeding nursery involving F3 lines from three sets of crosses each involving an SRF source.

| SRF Line | No. of Line or Row | Oil Content (%) Range Low | Oil Content (%) Range High | Oil Content (%) Average | Protein Content (%)** Range Low | Protein Content (%)** Range High | Protein Content (%)** Average | Glucosinolate (umol/g) Range Low | Glucosinolate (umol/g) Range High | Glucosinolate (umol/g) Average |
|---|---|---|---|---|---|---|---|---|---|---|
| R1439 Inbred | 47 | 40.8 | 47.6 | 44.3 | 24.3 | 29.4 | 27.0 | 7.8 | 15.2 | 11.1 |
| R1815 Inbred | 47 | 41.8 | 46.7 | 44.4 | 25.1 | 29.8 | 27.2 | 7.2 | 14.3 | 10.2 |
| R1931 Inbred | 43 | 41.9 | 47.2 | 44.2 | 24.8 | 29.6 | 27.5 | 6.5 | 14.5 | 10.8 |
| Check-46A65* | 38 | 42.6 | 46.4 | 44.5 | 25.5 | 29.8 | 27.7 | 13.0 | 16.3 | 14.5 |

*OP (open-pollination) canola commercial variety developed by Pioneer.
**Protein content in whole seed.

Each of the three SRF sources was selected as a donor parent and a Pioneer proprietary non commercial breeding line NS1822BC was selected as recurrent parent to initiate three different backcross series. The BC2 plants were self-pollinated successively twice to produce BC2S2. Several BC2S2 homozygous plants for the restorer gene were identified by marker analysis and harvested in bulk within each series. The three BC2S2 bulks became the male parent in three hybrids involving a common OGU CMS inbred line from Pioneer. The three male lines used in producing these hybrids are expected to have 87.5% genetic similarity since they all are BC2 descendents The hybrids were evaluated in an un-replicated incomplete block design experiment planted at seven locations in Western Canada. Two of these locations were lost due to poor weather. Data was collected from the remaining five locations. Each plot was planted with six meter long row spaced apart by 17 cm. Yield (q/ha), agronomic traits such as days to flower (50% of the plants in a row have at least one flower), days to mature (number of days from planting to the day when seed color changes from green to brown or black within the pods on bottom part (⅓) of raceme), early vigor (1=poor, 9=excellent), plant height (cm), resistance to lodging (1=poor; 9=excellent) and quality traits such as oil %, protein %, total glucosionolates and total saturated fatty acid were recorded (Table 14). The SRF based restorer produced competitive hybrids for all traits when compared to the commercial hybrid 45H26 which is based on NW1717 source.

TABLE 14

Agronomic and Quality Trait Data of the SRF-based Hybrids from 2007 Field Trial

| SRF Line | Yield q/ha | Days to Mature | Days to Flower | Early Vigor 1-9 | Lodging 1-9 | Plant Height cm | Oil % | Protein %** | Gluc umol/g | Total Saturate % |
|---|---|---|---|---|---|---|---|---|---|---|
| R1439 Hybrid | 19.09 | 89.9 | 46.2 | 7.7 | 6.1 | 126.8 | 51.8 | 45.5 | 10.2 | 6.93 |
| R1815 Hybrid | 20.49 | 89.7 | 46.0 | 7.5 | 6.5 | 126.4 | 51.2 | 46.7 | 13.1 | 6.77 |
| R1931 Hybrid | 20.56 | 89.5 | 46.1 | 7.3 | 6.6 | 114.8 | 51.8 | 45.1 | 12.5 | 7.02 |
| Check-45H26* | 20.14 | 89.7 | 45.8 | 7.1 | 6.8 | 129.1 | 50.8 | 45.7 | 11.1 | 7.05 |
| # Environment | 5 | 5 | 2 | 2 | 2 | 3 | 5 | 5 | 5 | 5 |

*NW1717 based hybrid canola commercial variety developed by Pioneer.
**Protein content in meal.

Percent oil is calculated as the weight of the oil divided by the weight of the seed at 0% moisture. The typical percentage by weight oil present in the mature whole dried seeds is determined by methods based on "AOCS Official Method Am 2-92 Oil content in Oilseeds". Analysis by pulsed NMR "ISO 10565:1993 Oilseeds Simultaneous determination of oil and water—Pulsed NMR method" or by NIR (Near Infra Red spectroscopy) (Williams, (1975) "Application of Near Infrared Reflectance Spectroscopy to Analysis of Cereal Grains and Oilseeds", *Cereal Chem.,* 52:561-576, herein incorporated by reference) are acceptable methods and data may be used for Canadian registration as long as the instruments are calibrated and certified by Grain Research Laboratory of Canada. Other methods as known to those skilled in the art may also be used.

The typical percentage by weight of protein in the oil free meal of the mature whole dried seeds is determined by methods based on "AOCS Official Method Ba 4e-93 Combustion Method for the Determination of Crude Protein". Protein can be analyzed using NIR (Near Infra Red spectroscopy), (Williams, (1975) "Application of Near Infrared Reflectance Spectroscopy to Analysis of Cereal Grains and Oilseeds', *Cereal Chem.,* 52:561-576, herein incorporated by reference). Data can be used for Canadian registration as long as the instruments are calibrated and certified by Grain Research Laboratory of Canada. Other methods known to those skilled in the art may also be used.

Glucosinolate content is expressed as micromoles per gram at 8.5% moisture. The total glucosinolates of seed at 8.5% moisture is measured by using methods based on "AOCS Official Method AK-1-92 (93) (Determination of glucosinolates content in rapeseed-colza by HPLC)"; herein incorporated by reference. NIR data can be used for Canadian registration as long as the instruments are calibrated and certified by Grain Research Laboratory of Canada.

Percent total saturates is the sum of each individual percentage saturate fatty acid to total oil (e.g. % C12:0+% C14:0+% C16:0+% C18:0+% C20:0+% C22:0+% C24:0). The typical percentages by weight of fatty acids present in the endogenously formed oil of the mature whole dried seeds are determined. During such determination the seeds are crushed and are extracted as fatty acid methyl esters following reaction with methanol and sodium methoxide. Next the resulting ester is analyzed for fatty acid content by gas liquid chromatography using a capillary column which allows separation on the basis of the degree of unsaturation and fatty acid chain length. This procedure is described in the work of Daun, et al., (1983) *J. Amer. Oil Chem. Soc.,* 60:1751-1754 which is herein incorporated by reference.

R1439, R1815 and R1931 are examples of plants/recombination events that contain the second generation shortened *Raphanus* fragment. These plants can be used to generate new restorer lines generate inbred lines and or generate hybrid lines. Further, any plant part from the new lines or descendants or progeny of the new lines, including but not limited to seeds, cells, pollen, ovules, nucleic acid sequences, tissues, roots, leaves, microspores, vegetative parts, whether mature or embryonic, are included in the scope of the invention. Plant cells, protoplasts and microspores, as well as other plant parts, can be isolated by cell and tissue culture methods as is known to those skilled in the art. Any plant cell comprising the new recombination event designated R1439, R1815 or R1931 is included within the scope of this invention.

Shortening the *Raphanus* Fragment Further—

R1439, R1815 and R1931 are examples of plants that contain the second generation shortened *Raphanus* fragment. These plants can be used to further shorten the *Raphanus* fragment by crossing them with the deletion mutant lines, R1, R2 and R5, (or other deletion mutant lines) and repeating the process over again. This process can be carried out repeatedly, until the *Raphanus* fragment is reduced to a length that is not associated with any undesirable genes or traits.

Generating New Restorer Lines—

The second phase recombinant *Brassica Ogura* restorer lines of this invention may be used to generate new restorer lines by crossing the commercial restorer lines and selecting for the shortened *Raphanus* fragment. In addition, new restorer lines can be generated de novo by following the methods of the present invention. Further, double haploid production can also be used to produce fixed SRF restorer lines. Methods of double haploid production in *Brassica* are known to those skilled in the art. See, for example, Beversdorf, et al., (1987) "The utilization of microspore culture and microspore-derived doubled-haploids in a rapeseed (*Brassica napus*) breeding program"—In Proc. 7th Int. Rapeseed Conf, (Organizing Committee, ed), pp. 13. Poznan, Poland; Swanson, "Microspore Culture in *Brassica*". Chapter 17, Methods in Molecular Biology, Vol. 6, P 159-169, Plant Cell and Tissue Culture, Edited by Pollard and Walker by The Humana Press (1990) which are incorporated herein by reference.

Generating Inbred Plants Using Restorer—

The second phase recombinant *Brassica Ogura* restorer lines of this invention may be used for inbreeding using known techniques. The homozygous restorer gene of the *Brassica* plants can be introduced into *Brassica* inbred lines by repeated backcrosses of the *Brassica* plants. For example, the resulting oilseeds may be planted in accordance with conventional *Brassica* growing procedures and following self-pollination *Brassica* oilseeds are formed thereon. Again, the resulting oilseeds may be planted and following self pollination, next generation *Brassica* oilseeds are formed thereon. The initial development of the line (the first couple of generations of the *Brassica* oilseed) preferably is carried out in a greenhouse in which the pollination is carefully controlled and monitored. This way, the glucosinolate content of the *Brassica* oilseed for subsequent use in field trials can be verified. In subsequent generations, planting of the *Brassica* oilseed preferably is carried out in field trials. Additional *Brassica* oilseeds which are formed as a result of such self pollination in the present or a subsequent generation are harvested and are subjected to analysis for the desired trait, using techniques known to those skilled in the art.

Generating Hybrid Plants Using New Second Phase Recombinant Restorer Lines as Male Parent—

This invention enables a plant breeder to incorporate the desirable qualities of an *Ogura* restorer of cytoplasmic male sterility into a commercially desirable *Brassica* hybrid variety. *Brassica* plants may be regenerated from the *Ogura* restorer of this invention using known techniques. For instance, the resulting oilseeds may be planted in accordance with conventional *Brassica*-growing procedures and following cross pollination *Brassica* oilseeds are formed on the female parent. The planting of the *Brassica* oilseed may be carried out in a greenhouse or in field trials. Additional *Brassica* oilseeds which are formed as a result of such cross pollination in the present generation are harvested and are subjected to analysis for the desired trait. *Brassica napus, Brassica campestris*, and *Brassica juncea* are *Brassica* species which could be used in this invention using known techniques.

The hybrid may be a single-cross hybrid, a double-cross hybrid, a three-way cross hybrid, a composite hybrid, a blended hybrid, a fully restored hybrid and any other hybrid or synthetic variety that is known to those skilled in the art, using the restorer of this invention.

In generating hybrid plants, it is critical that the female parent (P1) that is cross-bred with the *Ogura* restorer (P2) have a glucosinolate level that is sufficiently low to ensure that the seed of the F1 hybrid has glucosinolate levels within regulatory levels. The glucosinolate level of the seed harvested from the F1 hybrid is roughly the average of the glucosinolate levels of the female parent (P1) and of the male parent (P2). The glucosinolate level of the hybrid grain (F2) is reflective of the genotype of the F1 hybrid. For example, if the objective is to obtain hybrid grain (F2) having a glucosinolate level of less than 20 μmol/gram and the male parent (*Ogura* restorer) has a glucosinolate level of 15 μmol/gram, the female parent must have a glucosinolate level of less than 25 μmol/gram.

Generating Plants from Plant Parts—

*Brassica* plants may be regenerated from the plant parts of the restorer *Brassica* plant of this invention using known techniques. For instance, the resulting oilseeds may be planted in accordance with conventional *Brassica*-growing procedures and following self-pollination *Brassica* oilseeds are formed thereon. Alternatively, doubled haploid plantlets may be extracted to immediately form homozygous plants, as is known to those skilled in the art.

Vegetable Meal—

In accordance with the present invention it is essential that the edible endogenous vegetable meal of the *Brassica* oilseed contain glucosinolate levels of not more than 30 μmol/gram of seeds. The female parent which can be used in breeding *Brassica* plants to yield oilseed *Brassica* germplasm containing the requisite genetic determinant for this glucosinolate trait is known and is publicly available. For instance, *Brassica* germplasm for this trait has been available in North America since the mid-1970's.

Representative winter rape varieties that include the genetic means for the expression of low glucosinolate content and that are commercially available in Europe, for example, include, EUROL®, (available from Semences Cargill), TAPIDOR®, SAMOURAI® (available from Ringot). More recent winter rape varieties include 46W10, 46W14, 46WO9, 46W31, 45D01 and 45D03 (available from Pioneer®). Representative spring rape varieties that include the genetic means for the expression of low glucosinolate content and that are commercially available in Canada, for example, include KRISTINA® (available from Svalof Weibull). More recently, 46A76 (available from Proven®) and 46A65 (available from Pioneer®) are available.

The second phase recombinant *Ogura* restorer lines were deposited at National Collections of Industrial, Marine and Food Bacteria NCIMB Ltd, Ferguson Building, Craibstone Estate, Bucksburn, Aberdeen, AB21 9YA. Scotland, UK. The seeds that were deposited include restorer line R1439 (Accession No. NCIMB 41510), R1815 (Accession No. NCIMB 41511), and R1931 (Accession No. NCIMB 41512) discussed hereafter.

The edible endogenous vegetable oil of the *Brassica* oilseeds contains fatty acids and other traits that are controlled by genetic means (see, US Patent Application entitled, "Improved Oilseed *Brassica* Bearing An Endogenous Oil Wherein the Levels of Oleic, Alpha-Linolenic and Saturated Fatty Acids Are Simultaneously Provided In An Atypical Highly Beneficial Distribution Via Genetic Control", of Pioneer Hi-Bred International, Inc., WO91/15578; and U.S. Pat. No. 5,387,758, incorporated herein by reference). Preferably erucic acid of the *Brassica* oilseed is included in a low concentration of no more than 2 percent by weight based upon the total fatty acid content that is controlled by genetic means in combination with the other recited components as specified. The genetic means for the expression of such erucic acid trait can be derived from commercially available canola varieties having good agronomic characteristics, such as 46A05, 46A65, BOUNTY®, CYCLONE®, DELTA®, EBONY®, GARRISON®, IMPACT®, LEGACY®, LEGEND®, PROFIT®, and QUANTUM®. Each of these varieties is registered in Canada and is commercially available in that country.

Herbicide Resistance—

As is known to those skilled in the art, it is possible to use this invention to develop a *Brassica* plant which is a restorer of fertility for *Ogura* cytoplasmic male sterility, and produces oilseeds having low glucosinolate content and has other desirable traits. Additional traits which are commercially desirable are those which would reduce the cost of production of the *Brassica* crop or which would increase the quality of the *Brassica* crop. Herbicide resistance, for example, is a desirable trait.

A person skilled in the art could use the *Brassica* plant of this invention to develop a *Brassica* plant which is a restorer of fertility for *Ogura* cytoplasmic male sterility, produces oilseeds having low glucosinolate content and which is resistant to one or more herbicides. Herbicide resistance could include, for example, resistance to the herbicide glyphosate, sold by Monsanto™ under the trade mark ROUNDUP™. Glyphosate is an extremely popular herbicide as it accumulates only in growing parts of plants and has little or no soil residue.

There are two genes involved in glyphosate resistance in canola. One is for an enzyme which detoxifies the herbicide: it is called GOX, glyphosate oxidoreductase. The other is a mutant target gene, for a mutant form of EPSP synthase. One skilled in the art could use GOX or CP4 (5-Enol-pyruvylshikimate-3-phosphate synthase from *Agrobacterium* sp. CP4 (CP4 EPSPS)) with promoters in canola. Basically, the genes are introduced into a plant cell, such as a plant cell of this invention carrying the restorer gene for *Ogura* cytoplasmic male sterility, and then the plant cell grown into a *Brassica* plant.

As another example, a person skilled in the art could use the *Brassica* plant of this invention to develop a *Brassica* plant which is a restorer of fertility for *Ogura* cytoplasmic male sterility, produces oilseeds having low glucosinolate content and which is resistant to the family of imidazolinone herbicides, sold by BASF under trade-marks such as CLEARFIELD. Resistance to the imidazolinones is conferred by the acetohydroxyacid synthase (AHAS) gene, also known as acetolactate synthase (ALS). One skilled in the art could introduce the mutant form of AHAS present in varieties such as the Pioneer™ spring canola variety, 45A71, into a *Brassica* plant which also carries the shortened *Raphanus* fragment containing the restorer gene for the *Ogura* cytoplasm. Alternatively, one could introduce a modified form of the AHAS gene with a suitable promoter into a canola plant cell through any of several methods. Basically, the genes are introduced into a plant cell, such as a plant cell of this invention carrying the restorer gene for *Ogura* cytoplasmic male sterility, and then the plant cell grown into a *Brassica* plant.

If desired, a genetic means for tolerance to a herbicide when applied at a rate which is capable of destroying rape plants which lack said genetic means optionally may also be incorporated in the rape plants of the present invention as described in commonly assigned U.S. Pat. No. 5,387,758, that is herein incorporated by reference. Glyphosate resistance may be conferred by glyphosate N-acetyl transferase (GAT) genes: see for example, WO2002/36782 or WO2005/012515; US Patent Application Publication Numbers 2004/0082770, 2005/0246798, 2006/0200874, 2006/0191033, 2006/0218663 and 2007/0004912; and Canadian Patent Application Numbers 2,521,284 and 2,425,956 all of which are herein incorporated by reference.

Breeding Techniques—

It has been found that the combination of desired traits described herein, once established, can be transferred into other plants within the same *Brassica napus, Brassica campestris*, or *Brassica juncea* species by conventional plant breeding techniques involving cross-pollination and selection of the progeny.

Also, once established the desired traits can be transferred between the *napus, campestris*, and *juncea* species using the same conventional plant breeding techniques involving pollen transfer and selection. The transfer of traits between *Brassica* species, such as *napus* and *campestris*, by standard plant breeding techniques is documented in the technical literature.

(See, for instance, Tsunada, et al., "*Brassica* Crops and Wild Alleles Biology and Breeding." Japan Scientifc Press, Tokyo (1980)).

As an example of the transfer of the desired traits described herein from *napus* to *campestris*, one may select a commercially available *campestris* variety such as REWARD®, GOLDRUSH®, and KLONDIKE®, and carry out an interspecific cross with an appropriate plant derived from a *napus* breeding line, such as that discussed hereafter (i.e., R1439, R1815 and R1931). Alternatively, other *napus* breeding lines may be reliably and independently developed using known techniques. After the interspecific cross, members of the F1 generation are self pollinated to produce F2 oilseed. Selection for the desired traits is then conducted on single F2 plants which are then backcrossed with the campestris parent through the number of generations required to obtain a euploid (n=10) campestris line exhibiting the desired combination of traits.

In order to avoid inbreeding depression (e.g., loss of vigor and fertility) that may accompany the inbreeding of *Brassica campestris*, selected, i.e., BC1 plants that exhibit similar desired traits while under genetic control advantageously can be sib-mated. The resulting oilseed from these crosses can be designated BC1SIB1 oilseed. Accordingly, the fixation of the desired alleles can be achieved in a manner analogous to self-pollination while simultaneously minimizing the fixation of other alleles that potentially exhibit a negative influence on vigor and fertility.

A representative *Brassica juncea* variety of low glucosinolate content and low erucic acid content into which the desired traits can be similarly transferred is the commercial variety 45J10.

Stand of Plants—

The oilseed *Brassica* plants of the present invention preferably are provided as a substantially uniform stand of plants. The *Brassica* oilseeds of the present invention preferably are provided as a substantially homogeneous assemblage of oilseeds.

The improved oilseed *Brassica* plant of the present invention is capable of production in the field under conventional oilseed *Brassica* growing conditions that are commonly utilized during oilseed production on a commercial scale. Accordingly, the invention includes a method of growing a *Brassica* plant, comprising: sowing seed designated R1439, R1815 or R1931 and having NCIMB Accession Numbers 41510, 41511, and 41512 respectively, or a descendent (for example, a sexual progeny or offspring), a vegetative cutting or asexual propagule or from a plant produced by crossing R1439, R1815 or R1931 with a second plant; and growing the resultant plant under *Brassica* growing conditions. Such oilseed *Brassica* exhibits satisfactory agronomic characteristics and is capable upon self-pollination of forming oilseeds that possess the commercially acceptable glucosinolate levels within the meal present therein. Further, the applicant's teaching includes an assemblage of crushed *Brassica* seed of the lines with SRF, their descendants and progeny thereof, and the oil and meal from such lines. The oil can be produced by crushing seeds produced by the plant line designated R1439, R1815 or R1931, or their descendents, sub-lines, or from a plant produced by crossing R1439, R1815 or R1931 with a second plant; and extracting oil from said seeds. The method can further comprise the step of: refining, bleaching and deodorizing the oil.

DEPOSITS

The seeds of the subject invention were deposited in the National Collections of Industrial, Marine and Food Bacteria Ltd (NCIMB), Ferguson Building, Craibstone Estate, Bucksburn, Aberdeen, AB21 9YA Scotland, UK

| Seed | Accession No. | Deposit Date |
|---|---|---|
| *Brassica napus oleifera* R1439 | NCIMB 41510 | Oct. 22, 2007 |
| *Brassica napus oleifera* R1815 | NCIMB 41511 | Oct. 22, 2007 |
| *Brassica napus oleifera* R1931 | NCIMB 41512 | Oct. 22, 2007 |

All publications, patents and patent applications are herein incorporated by reference in their entirety to the same extent as if each individual publication, patent or patent application was specifically and individually indicated to be incorporated by reference in its entirety.

The present invention has been described in detail and with particular reference to the preferred embodiments; however, it will be understood by one having ordinary skill in the art that changes can be made thereto without departing from the spirit and scope thereof.

TABLE 1a

Rf Markers for SRF Restorer Lines

| 01 | 02 Phenotype Cytoplasm | 03 | 04 Fertile CMS | 05 Sterile CMS | 06 Sterile CMS | 07 Sterile CMS | 08 Fertile CMS | 09 Fertile CMS | 10 Fertile CMS |
|---|---|---|---|---|---|---|---|---|---|
| Marker Group | Marker | Size (bp) | NW1717 (wildtype) | Deletion Mutant R1 | Deletion Mutant R2 | Deletion Mutant R5 | SRF-R1439 | SRF-R1815 | SRF-R1931 |
| I | RMA01 | 247 | + | − | + | + | − | − | − |
| | RMA02 | 198 | + | − | + | + | − | − | − |
| | RMA03 | 233 | + | − | + | + | − | − | − |
| | RMA04 | 348 | + | − | + | + | − | − | − |
| | RMA05 | 581 | + | − | + | + | − | − | − |
| | RMA06 | 249 | + | − | + | + | − | − | − |
| | RMA07 | 350 | + | − | + | + | − | − | − |
| | RMA08 | 354 | + | − | + | + | − | − | − |
| | RMA09 | 357 | + | − | + | + | − | − | − |
| | RMA10 | 208 | + | − | + | + | − | − | − |
| II | RMB01 | 572 | + | − | − | − | + | + | + |
| | E35M62 | 215 | + | − | − | − | + | + | + |
| | RMB02 | 301 | + | − | − | − | + | + | + |
| | RMB03 | 459 | + | − | − | − | + | + | + |
| | RMB04 | 168 | + | − | − | − | + | + | + |
| | RMB05 | 325 | + | − | − | − | + | + | + |
| | RMB06 | 504 | + | − | − | − | + | + | + |
| | RMB07 | 537 | + | − | − | − | + | + | + |
| | RMB08 | 524 | + | − | − | − | + | + | + |

TABLE 1a-continued

| Rf Markers for SRF Restorer Lines | | | | | | | | | |
|---|---|---|---|---|---|---|---|---|---|
| | RMB09 | 316 | + | − | − | − | + | + | + |
| | RMB10 | 358 | + | − | − | − | + | + | + |
| | OPF10 | 496 | + | − | − | − | + | + | + |
| | RMB11 | 317 | + | − | − | − | + | + | + |
| | RMB12 | 750 | + | − | − | − | + | + | + |
| III | RMC01 | 356 | + | + | + | − | + | + | + |
| | RMC02 | 479 | + | + | + | − | + | + | + |
| | RMC03 | 266 | + | + | + | − | + | + | + |
| | E38M60 | 116 | + | + | + | − | + | + | + |
| | RMC04 | 213 | + | + | + | − | + | + | + |
| | RMC05 | 500 | + | + | + | − | + | + | + |
| | RMC06 | 482 | + | + | + | − | + | + | + |
| | RMC07 | 466 | + | + | + | − | + | + | + |
| | RMC08 | 547 | + | + | + | − | + | + | + |
| | RMC09 | 327 | + | + | + | − | − | + | + |
| | RMC10 | 465 | + | + | + | − | − | + | + |
| | RMC11 | 273 | + | + | + | − | − | + | + |
| | RMC12 | 347 | + | + | + | − | − | + | + |
| | RMC13 | 382 | + | + | + | − | − | + | + |
| | RMC14 | 533 | + | + | + | − | − | + | + |
| | RMC15 | 711 | + | + | + | − | − | + | + |
| | RMC16 | 400 | + | + | + | − | − | + | + |
| | RMC17 | 554 | + | + | + | − | + | + | − |
| | RMC18 | 525 | + | + | + | − | + | + | − |
| | RMC19 | 543 | + | + | + | − | + | + | − |
| | RMC20 | 463 | + | + | + | − | + | + | − |
| | RMC21 | 269 | + | + | + | − | + | + | − |
| | RMC22 | 747 | + | + | + | − | + | + | − |
| | RMC23 | 219 | + | + | + | − | + | + | − |
| | RMC24 | 363 | + | + | + | − | − | − | − |
| | OPC2 | 678 | + | + | + | − | − | − | − |
| | RMC25 | 364 | + | + | + | − | − | − | − |
| | RMC26 | 201 | + | + | + | − | − | − | − |
| | RMC27 | 238 | + | + | + | − | − | − | − |
| | RMC28 | 623 | + | + | + | − | − | − | − |
| | RMC29 | 198 | + | + | + | − | − | − | − |
| | RMC30 | 525 | + | + | + | − | − | − | − |
| | RMC31 | 379 | + | + | + | − | − | − | − |
| | RMC32 | 450 | + | + | + | − | − | − | − |
| | RMC33 | 275 | + | + | + | − | − | − | − |
| IV | E33M47 | 122 | − | − | − | − | − | − | − |
| | E32M50 | 252 | − | − | − | − | − | − | − |
| | OPN20 | 587 | − | − | − | − | − | − | − |
| | OPH15 | 637 | − | − | − | − | − | − | − |
| | IN6RS4 | 236 | − | − | − | − | − | − | − |
| | E33M58 | 281 | − | − | − | − | − | − | − |
| | E32M59A | 406 | − | − | − | − | − | − | − |
| | E32M59B | 350 | − | − | − | − | − | − | − |
| | OPH03 | 591 | − | − | − | − | − | − | − |
| V | IN10RS4 | 287 | + | + | − | − | + | + | + |
| | RME01 | 454 | + | + | − | - | + | + | + |
| | RME02 | 233 | + | + | − | − | + | + | + |
| | RME03 | 533 | + | + | − | − | + | + | + |
| | RME04 | 699 | + | + | − | − | + | + | + |
| | RME05 | 477 | + | + | − | − | + | + | + |
| | RME06 | 480 | + | + | − | − | + | + | + |
| | RME07 | 579 | + | + | − | − | + | + | + |
| | RME08 | 496 | + | + | − | − | + | + | + |

TABLE 1a-continued

Rf Markers for SRF Restorer Lines

| | | | | | | | | |
|---|---|---|---|---|---|---|---|---|
| RME09 | 574 | + | + | − | − | + | + | + |
| RME10 | 570 | + | + | − | − | + | + | + |
| Rf Marker Loss (I, II & II) | | 0/59 | 24/59 | 14/59 | 49/59 | 29/59 | 21/59 | 28/59 |

| 01 | 02 Phenotype Cytoplasm | 03 | 11 | 12 | 13 | 14 |
|---|---|---|---|---|---|---|
| Marker Group | Marker | Size (bp) | Forward Primer (5'->3') | SEQ ID | Reverse Primer (5'->3') | SEQ ID |
| I | RMA01 | 247 | GCTTCTACTTCCATACCAATGG | NO. 1 | CAAGCTCTTCGGTATGAAACG | NO. 2 |
| | RMA02 | 198 | AAGCTTCAGCTTATCCTTGG | NO. 3 | GTTCGTTGTAGATCGGATCC | NO. 4 |
| | RMA03 | 233 | CTTGCTGCAAAGCACTTCTC | NO. 5 | AGCTTCAGACCAAGTCCCAG | NO. 6 |
| | RMA04 | 348 | GGATCACGAAACTCCCAAGG | NO. 7 | TCATATCTCCCTCCTTGTCCA | NO. 8 |
| | RMA05 | 581 | AAGCTCAGGCTCCTTCACCG | NO. 9 | GGGAAGGAGATCCGGACTCA | NO. 10 |
| | RMA06 | 249 | AAGCTTATAGAGTAGCCATTGAG | NO. 11 | TCTAAGATCAGTATATGGACAGC | NO. 12 |
| | RMA07 | 350 | CGGACTCTTTAGCTCCGCCA | NO. 13 | CACCTCCTGTCGGCATCTCA | NO. 14 |
| | RMA08 | 354 | TATTCTGCTTCATGTGGTGATC | NO. 15 | ACGATTGTTAAGTTGACGAAAG | NO. 16 |
| | RMA09 | 357 | TTTTTCAATGCTTCTGTGCAG | NO. 17 | GCACAAAATTACAATCAGCGC | NO. 18 |
| | RMA10 | 208 | AAGCTTTGTGTTGCTAATGTAT | NO. 19 | AGTTGAAACGATATAACTTGTGA | NO. 20 |
| II | RMB01 | 572 | ATTGTCGTTGTCGATGCATC | NO. 21 | AGAAGAAGAAAGTGCCAAGCA | NO. 22 |
| | E35M62 | 215 | AAAATTGCGAGGTTCAGGAAT | NO. 23 | CTCCAGCTCCTGTTAGTGACTCTT | NO. 24 |
| | RMB02 | 301 | AATTTATGGGGTGTCAATTGA | NO. 25 | TGGCTGATTTGCAACATAAA | NO. 26 |
| | RMB03 | 459 | GTTCTGGCTATGTCGAGACCAC | NO. 27 | CCAGAGTTTGGAGGCAGACT | NO. 28 |
| | RMB04 | 168 | GAGTTGTGGGTTTGGCCGTC | NO. 29 | ACGCACCAGAACGATCAATC | NO. 30 |
| | RMB05 | 325 | ATCAGAGCAAAAGAGTGCGTAG | NO. 31 | CGAAATACCGAAGAACCAAATC | NO. 32 |
| | RMB06 | 504 | ACATCGGTCGAAGAAGTTCC | NO. 33 | AATCTTGAGGCAAGCCTGAC | NO. 34 |
| | RMB07 | 537 | AGCTTCTATTCAGCCAAAAGG | NO. 35 | GCATTACCGTTGGAAAATTTC | NO. 36 |
| | RMB08 | 524 | ACCAAAGACACCATAACGAGG | NO. 37 | CGCACTTTTAGCAGCAGTTC | NO. 38 |
| | RMB09 | 316 | CCCACTCTTGTTACCTTCAGC | NO. 39 | GTTCCCACAGCCTACCAGTAC | NO. 40 |
| | RMB10 | 358 | ATTGGATTTGAATGAGATGG | NO. 41 | TCCATTGATCTCTGCACATC | NO. 42 |
| | OPF10 | 496 | AACTTTTTGTGTTTGATTTCTTGC | NO. 43 | ACTCCTTCTAAACAAAACCAAACA | NO. 44 |
| | RMB11 | 317 | AAGCTTGTCTCCTACGTACTTC | NO. 45 | TCAGAAAGATATTTCACGTCAC | NO. 46 |
| | RMB12 | 750 | TGGACTAAGAAAGGGTCAGGTA | NO. 47 | CGAAGAATCTCTACTCTGTTGT | NO. 48 |
| III | RMC01 | 356 | AGGAAGTGAGAGGCAGTTGG | NO. 49 | TCCATGGGTGTCCTAGGATC | NO. 50 |
| | RMC02 | 479 | TGCGTAACACTTCTTTGCTTC | NO. 51 | TGCAGAACTCAAAGCCATTC | NO. 52 |
| | RMC03 | 266 | AAGCTTATTTTCATCCTGCAA | NO. 53 | CATCACCATCATCACAGTAATT | NO. 54 |
| | E38M60 | 116 | TCCATAGAAGAAACTCTTTGCAAC | NO. 55 | TCGACACACTTACTAATCTGAGAG TG | NO. 56 |
| | RMC04 | 213 | TATTTTGTCCTCGGTTAGATC | NO. 57 | TTCCTTTGTGTTTGGTTAGGG | NO. 58 |
| | RMC05 | 500 | TGCGAGTTTAATCCGGACGC | NO. 59 | CCGCGTTATTCTGGTTCAGAGA | NO. 60 |
| | RMC06 | 482 | TTCCTCGGCAAGAACAACGC | NO. 61 | GCCGTCTAACAGCAGGTGCA | NO. 62 |
| | RMC07 | 466 | CCGTATTTGAAAACGTGGCG | NO. 63 | TCAACCGTGAATTTGGGTCG | NO. 64 |
| | RMC08 | 547 | GAGGCGAAAACATAAACAAGG | NO. 65 | ATCGCCAAAACTGTTTCAGG | NO. 66 |
| | RMC09 | 327 | TCGGTTTTTCGAGGGTATCA | NO. 67 | TCCGATTTAGAATCGAACCTG | NO. 68 |
| | RMC10 | 465 | TCCTGCAGTTTGAAATCCTTG | NO. 69 | AAGTTTCCCCAAACCAACTTC | NO. 70 |
| | RMC11 | 273 | AAGCTTAATAGCGACTTCTTC | NO. 71 | TGAAAACCCTAGTCTCTCTCTC | NO. 72 |
| | RMC12 | 347 | AATGGATGAACTCGAGACGG | NO. 73 | TGATAACCCCTCGTTTCCTG | NO. 74 |
| | RMC13 | 382 | TGTCAGCATTCAGCAGAAGC | NO. 75 | AGGGATTGAAAGCTGGGAAC | NO. 76 |
| | RMC14 | 533 | TTGACGGTTACCCAAAATACCG | NO. 77 | TTGATTGCTTCACCCTCACCC | NO. 78 |
| | RMC15 | 711 | AAAGCATCCTTTGCAAGGGG | NO. 79 | GAACCAAAAATGAGTGGATGG | NO. 80 |
| | RMC16 | 400 | AAATTGTTACAAAGTATGGAGAAA T | NO. 81 | TTCAGTAAACATTTTACTCATTCTC | NO. 82 |
| | RMC17 | 554 | TTTCCACACAAATCGGATTTAA | NO. 83 | TGGCCAATGAAAGTTTACTGAT | NO. 84 |
| | RMC18 | 525 | ACCAAACCGAGAACAAAATAGGTG | NO. 85 | GGTTCGAATACTTTGGTTTTTTGG | NO. 86 |
| | RMC19 | 543 | TGGAGGTGTCAAAGTGTGGC | NO. 87 | CGCAAGTCACTTTATTTGGC | NO. 88 |
| | RMC20 | 463 | GAACCACGACTTTGGGTCTG | NO. 89 | GCTTTGGTTAGAATGTCGGC | NO. 90 |
| | RMC21 | 269 | GAGAATATTGGAAGAAAGCGG | NO. 91 | AAGTCGTGGTTCCTTTGAGG | NO. 92 |
| | RMC22 | 747 | GCTCTACGAGTGAGGATCAAAG | NO. 93 | CACTTTCGGAATCCAAGCTC | NO. 94 |
| | RMC23 | 219 | AGCTTATAGGCTTCTAGACCC | NO. 95 | GTTTCTGTTTCTGCAGGCTC | NO. 96 |
| | RMC24 | 363 | AGCTTTAATTCATGTATTTTTACA | NO. 97 | AATTTTTTTGTGATACATTTCAA | NO. 98 |
| | OPC2 | 678 | CTGTAACTTTCAACCCAACTCGTA GAA | NO. 99 | TTTTGGGGATTACTCTTCTTAGCTT TC | NO. 100 |
| | RMC25 | 364 | AAGCTTGATCAAAGATCACAG | NO. 101 | AACAAACTAATGAGCAACAGG | NO. 102 |
| | RMC26 | 201 | CAGACCGTTCAAGTTCATGG | NO. 103 | CAAGTTGCTCGGCATATGAT | NO. 104 |
| | RMC27 | 238 | CCTTCTCCAAACCGGTAAAC | NO. 105 | TTTTGAGAAATGACGGATCG | NO. 106 |
| | RMC28 | 623 | AGACCAAGAGGAAGCGTAGC | NO. 107 | AAGAAACAACCCAGACTCCG | NO. 108 |
| | RMC29 | 198 | CAATGATTTATACTTCGTTTTTGC | NO. 109 | GCAGCGTACGGTATGTCTATCT | NO. 110 |
| | RMC30 | 525 | CATTTGGTTTGTCCGTGTGT | NO. 111 | AGGCGACAACCTCTTTCAAC | NO. 112 |
| | RMC31 | 379 | CATTTTCTTTAACAACGCGC | NO. 113 | ACGACGGCGACATGTAGTAC | NO. 114 |
| | RMC32 | 450 | TCTCTCACACTTTCTCTCAC | NO. 115 | CGCCGAGAATTTCCGCGCC | NO. 116 |
| | RMC33 | 275 | CAAATCAATACCATTAAAAGTGG | NO. 117 | TTTTTGATTAATTTCCTTTCACA | NO. 118 |

TABLE 1a-continued

| Rf Markers for SRF Restorer Lines | | | | | | |
|---|---|---|---|---|---|---|
| IV | E33M47 | 122 | AATAGAGGGAGAGGATGAAAGAAC | NO. 119 | AGCTACCTAACAGGTTTTGTTATAAAG | NO. 120 |
| | E32M50 | 252 | TCACATTAGTAAAACGATTGTCCAC | NO. 121 | GATTGATTTTTGGACTCCGTT | NO. 122 |
| | OPN20 | 587 | CCTTAGTTTAGTTGTAGGTGGTGG | NO. 123 | AGAAACCGCTCAATTTTAACATAA | NO. 124 |
| | OPH15 | 637 | CCTTGGCTATGTGCTTATGTATTT | NO. 125 | TAAAACACAGAGACAATCGTGAGG | NO. 126 |
| | IN6RS4 | 236 | CATTGATACATGAATGCAAAGAAG | NO. 127 | GATGAAAACATTTACAGACAATGC | NO. 128 |
| | E33M58 | 281 | CTGCATAAAATTATCGAAGACAGATA | NO. 129 | TTCTGTTTCAGCGCTAACAAATC | NO. 130 |
| | E32M59A | 406 | CTTTGTCATTGTGTGTGTGTGTGT | NO. 131 | AATATGATTTCCAATTTGCCAAGT | NO. 132 |
| | E32M59B | 350 | AATTCTTGCTCCATTATGATTTCA | NO. 133 | CACAAGACGATCAGGAAAAAGAA | NO. 134 |
| | OPH03 | 591 | TCCACTCCTAGTTCACAATCTATTTT | NO. 135 | TATACAAAATGTTGGAATACACAAGG | NO. 136 |
| V | IN10RS4 | 287 | CAGAACACAGTTCTATGACACTG | NO. 137 | TATAGGAGCTTTGTTCTGTAGTGG | NO. 138 |
| | RME01 | 454 | TCCATTGCAGAATTCACCTG | NO. 139 | TGTTTTCTTCGTCATGTCGG | NO. 140 |
| | RME02 | 233 | CTTGAGGGAAGGAGACGAGA | NO. 141 | ATTTTGGGTCATGGGTTTTT | NO. 142 |
| | RME03 | 533 | ATATCCTTAAACCCTTGCGC | NO. 143 | TTGAATACCTCCAAGGACCC | NO. 144 |
| | RME04 | 699 | GGTCTCAGGTTTTGTGGGAG | NO. 145 | GGTTCTCAAAGATTCCGAGG | NO. 146 |
| | RME05 | 477 | CTTGGTCACACCCATCTTCTC | NO. 147 | TGTCCGATAAACTCTCTGCG | NO. 148 |
| | RME06 | 480 | ATCAACCACGTTCATCCATG | NO. 149 | AACTCAAATACTCTCGGCCAG | NO. 150 |
| | RME07 | 579 | ATTTACCAAATGGATCACTCTGG | NO. 151 | CCGAGAATTGAACATTGTAAAGA | NO. 152 |
| | RME08 | 496 | CAATTCCACAACGTAGCAGAG | NO. 153 | CTTTTCGACTAAGAACCGGC | NO. 154 |
| | RME09 | 574 | AGCTTGGACTATGCCGTTTG | NO. 155 | ATTTCAGGACCGGCTATGTG | NO. 156 |
| | RME10 | 570 | TCGAGAATCCTCTACAAACGC | NO. 157 | AAGCACCACTTATTCGACAGC | NO. 158 |
| Rf Marker Loss (I, II & II) | | | | | | |

TABLE 1b

Rf Marker Sequences

| Marker | Size | SEQ ID | Sequence (5' -> 3') |
|---|---|---|---|
| RMA01 | 247 | NO. 159 | GCTTCTACTTCCATACCAATGGACATTATCGCATAGCTGGCTATATTCTTGGAGTCAGCTGGGAGAAGGTTAGTTCCTTGGTCTTCGTATCGGTGAGCTATGTACTGAGTAATGGCTCTTGATTCTACACAAAAAAAAAACAAATCATGTTAGTGAAATTTTCTTCTTATGCGTATTTGTTCAATTCAGGTTTGAGATTGAAGATGAGATAATGATTGCTTATAAACGTTTCATACCGAAGAGCTTG |
| RMA02 | 198 | NO. 160 | AAGCTTCAGCTTATCCTTGGCCTAGAAGCAACGTCAATAACTTTCCAACCGTGCCTTGGTTTTACGATCGGGAAGATGATCTGGAAAGCTGACAACGAGATCTTTCTATTGACATCTCGCTCGTTTTCTGGTTCCTTCTAGATCAACGGGAAAACACTGATGAAGTTGACTTATCGGCGGATCCGATCTACAACGAAC |
| RMA03 | 233 | NO. 161 | CTTGCTGCAAAGCACTTCTCTCATCCACTCTTAGTTCAACTTCTGCTTCAAGCTTTAGTATTGTTTGCTTTAAACTTGAGACATCCTCTTGCAAACTCTTCACTGATGCTACCGAGGAGAGACTGAGCTCACTGAGACCTTTGTTCTCAACCTTGGCTTGCTGAATCTCCTCATGCAGCTCGTTGTTTCGGAACTCTCCATGTCATTCATGATCTGGGACTTGGTCTGAAGCT |
| RMA04 | 348 | NO. 162 | GGATCACGAAACTCCCAAGGAAACTTATAAGTATTTTAGGTAAGACCGGTGTCAAGAAGAACCTGAGGACTATCTTTTCTTGAGAAGAAGTATCAGCTTTCATCAGGATGAATCTTTCACCGGTAGAGATAGTCTAAGAGAGACACAAGAAAGAACTTCCTATTCCCTTCTTCCTTTCAAAAAAAAAACTCAGGAAAAGAGCTGAAGAGGAAGACCACTAAAACACAAGTAGTAAGGCTGACATATTTAAGGCTAGACAGAAACGTAACAGAAAGGAAAATAAGACTCAAGAACATGAAAGTAGACAAAGGGTTGAAAGAAAAGATATGGACAAGGAGGGAGATATGA |
| RMA05 | 581 | NO. 163 | AAGCTCAGGCTCCTTCACCGCTTCTTCTACATCAATGTTCTTCCCCTTTGATTTGCTACGTTCTTCCCCAGAAGAAGCACTAATCTCAGATTCTTCATCACTGCTCTCATCAGAATCACTGTACCTCCTCTTCCTCCTATGACCTCTCCTCTTCCTACTACTTCCGCTTTTCTTCTTCTTATTCCTTCTTCTACGCCTCCTATCTTCCTCATCCGAATCATCACTCTCGCTCTCCTCTTCCGATTCGCTATCACTCCTTCTCCTACGCTTACTCCTAGACCTCTTACTCTTCCTCTTCTTCCTAGATCTATCAGATTCAGATCCCGACTTACCCGAATCAGATTCGCCTTTCCGTTGTTTCGGATCGTCAACATCCTTCTCCGGAACCACCTCCTCGTCAGCGGCGTTCTCATCGGACTCTTCCTCGTCGGGATCTCTGGGCGGACTCGGCCGTGTTCTCCCATATGCAGTACTTTCCAGATTTCCTCATCCTTGAGGCGTTTAAGCCCTCCTGTACTCCTCGTGACCTCAATTCCTTTCAACCTCTTTCGTTCCGGAGTCTGAGTCCGGATCTCCTTCCC |
| RMA06 | 249 | NO. 164 | AAGCTTATAGAGTAGCCATTGAGTCGCCTCTGATTAACTTTTTGAAAAGCCAAGTGTGAACTTTTTCCTCCTTCGTTTCCCAAAAAAAAACCACTTTTCTTTGATAACATTCTCTTGGATCCAAGCAACCCAAACTGAATCAGTTTTGGAAGAATAACATCCACATGAGCTTGAGCATTCAAGATTTGTTTCATACATGGATGTTCCGGCTAGTGATAAATATTTTGCTGTCCATATACTGATCTTAGA |

TABLE 1b-continued

Rf Marker Sequences

| Marker | Size | SEQ ID | Sequence (5' -> 3') |
|---|---|---|---|
| RMA07 | 329 | NO. 165 | CGGACTCTTTAGCTCCGCCATAACAACCACAGCAGCCTCCGGTGTGAAAAAACTCCACTTTTTCACAACAACCCACCGT CCAAGATCCCTCTCCTTCACCAGAACCGCAATCCGCGCCGAGAAAACAGATTCCGCCGCCGCCGCCCCAGCCCCCGCCG TGAAAGAAGCTCCGGTGGGATTCACGCCGCCTCAGCTAGACCCAAACACACCGTCACCGATCTTCGCGGGGAGCACCGG TGGGCTTCTCCGCAAAGCCCAGGTGGAAGAGATCTACGTTATTACATGGAACTCGCCGAAAGAACAGATCTTTGAGATG CCGACAGGAGGTG |
| RMA08 | 354 | NO. 166 | TATTCTGCTTCATGTGGTGATCATCTCCAAACTCACATAGCCAAAATATTGTTTCAAAAAGTTCGATAACCTTATCAAT ATCGATCCACTCCAGTGGTCTTTTAATAATGTAATCAATGGATAGTCAATTCGTGAATCTATTGATTCTTGTATATATG GATATGTGAAAGGAGAACAAATTAAATCATGTACAAGTCAAACATTGGAGTAGTATTAGCCTCCATTTTCTATAGATAT GAATGCTCCGGAAAACAACTTCTTGTTCAAGATGAAATCAGTACATGAACATCGTACATATATCGAGTAGATTCTCTAT GATGTAAGTTCATTTTCTTTCGTCAACTTAACAATCGT |
| RMA09 | 357 | NO. 167 | TTTTTCAATGCTTCTGTGCAGAATACCCTAATTCTCAGGAAATTCAACATGGTCTACCTCTAATACATTGGCAACAGGT TCAAGGAGATGATGCTCCTCAGGTGATTTTTAAATTATATTTCTCTTTTTAAAGGCAGTTATTTATTATAATTATTTTC TTGTCAATAATATTCACCAAAGATATCCTCACTAATACATTCACTCTTCCTTTTACCTTGATTTATACGTTTTCCCCTG GAATCTATACTTAATATTCCATCAAAAATAGTTATTGTATGTTTACTTTGAAAGGTACCAAAACCACATATTTAATTTC AATCGTTATTATGATTATATGCGCTGATTGTAATTTTGTGC |
| RMA10 | 208 | NO. 168 | AAGCTTTGTGTTGCTAATGTATATATTAACATCTTGTCAAACTACTCATCATAATTATATATGCTACAACCCGGGCTAC AACTAATGAAATTTGATCAACTGATCATCATTTTTGGTAAAGTTATACAAAATATTATTTCGCTGATAAATTTTTCAGT CTTTCAAAAATGTGGTTTTTATTTTTATCACAAGTTATATCGTTTCAACT |
| RMB01 | 572 | NO. 169 | ATTGTCGTTGTCGATGCATCCTCCAGCTGCTCTTCAGGCCATGTTGTTGATGATCCTTTCATCGGGGAGAAACAGCTGT CCATTTTCCCTATCTTCTTGTCCAAATCTGTGATGCAGTCGCTCAGGCTGTTCCTGTTTGCCTGCCTCAGCCAAGGTAT AGCTACAGACGCATTCTGCGAGATAAAACTCTCGCACGACTTGATTCTTTTCGGCTTTCCGGAAGACGGCTTCTTGCTA GGTAACTGAGAGTTATTATTCCACACATGAATCCCCGAGTCTTCTGTTGTTGACACGATGTGTTTACCGTCCAAAGTAA ACGAGGCACGTGTTGTGCAGACGCCAGAAGCTGCAAAAAAGGAAGTTAGCCAAAAGGTTATACATCTTAATTCTTAAGT AGAACAAAAAAAAATAAGGCACTAATTGTCTCTAATACTAACCTTTAAGCTTGCAGATGACATCATCACCAGATATGAT ACGAATCTGTGAATCAGCACAGGTAACCATTACTTTGTCGGAGTCATTGGGAAAATACTCAAGACCAGTGATCCTTTTG CTTGGCACTTTCTTCTTCT |
| E35M62 | 215 | NO. 170 | AAAATTGCGAGGTTCAGGAATGCTGTTTACAGCGTTGATGAAGACTTGATAGGGGTCCGAAAGGGCATCATAGGACAAG TAGTTAGACATAGGATGTTCAGTACAAGAGTTCACTGAGTCACAGTGATAATCTCGCAGGTAGCTTGGAGCCTTATGAA CTCTGCGTGTAGAAGTGTCTGGAGGTCTGCTTGAAGAGTCACTAACAGGAGCTGGAG |
| RMB02 | 301 | NO. 171 | AATTTATGGGGTGTCAATTGAACCCCCCTAAACTGCATGTAGGTCCGCCACGGGATGGAAATGAAACTAGTAAAATAATA ACAATTTTAAAGATGCTGATAATAGTAAATAACCAATTAATTTGCATAATAAAAATAATTACCATCAGGACGAGCATAT AGTAAATCATGACAGGGTCCATGACATAGTTACATATGCATCTTTAAAAACTACTAGAACAATAGTCGATGAAATTGGA AATATTGAAAAACCTAACTTGAATGCAAAATGATTTTATAAAGTTTTATGTTGCAAATCAGCCA |
| RMB03 | 459 | NO. 172 | GTTCTGGCTATGTCGAGACCACTGAACCACCATGCCTCATGTCTGAATCGTGAGCTCGACTTCTTCTTCTTCTTCGTGG GTTTCGTCATCATCAACTCGCAACCGCCGTGAACATGCTCATTCTTAATCTACGATTCTCAGCCGTGTGTGCTATGAAA CTCACATTGAGCTCCTAATCTCCACCGTAATCCTCCTTTCTGTTACCATGATCTTAGACGTAATCAAAACGATGTAGAA CCGGTGGCGTCATTCTCTGACACAGATCCAATTCAACAAGATCTCACCGGAATCCATGGTCATGACAAGCTCAACATCG TCGTCCAGAATCAAGCCTTGTCGTCTCAGCTCACCTTTGGTCGGATTGAAATCTCGATCGAACACTAACAATGGTCATC TTTAGCTTATTTGCATCTGGGTCCCTCAAATTTCAGTTATTTTCAGTCTGCCTCCAAACTCTGG |
| RMB04 | 168 | NO. 173 | GAGTTGTGGGTTTGGCCGTCTCTGCTGGGATTAGCACCCCTGGAATGTGTGCGAGTCTTGCGTATTTTGATACGTATAG GCGTGCGAGATTGCCGGCGAATCTGGTTCAGGCGCAGAGAGATCTCTTTGGAGCTCATACTTACGAGAGGATTGATCGT |
| RMB05 | 325 | NO. 174 | TCTGGTGCGTATCAGAGCAAAAGAGTGCGTAGATGGGTTTTGAGTTTTGAAGGAGGAAACATTGGTTTCTCCATGCATT TTGAAGTTTGAGTGAGGATAATGTTTTCTGTTTTAGTTCGGCTCGGATAAAAATTGTGACCGCTTTTTTTTGTTGTTGT TTTGATTTGGAATCTATTTTTTTGATGTTTTGGTCTGCCCATCCATATCTAGATTATATAGTTAGATTATATAGTTGGA TAGGAAAAGTTTTTTTTTTTGGGTCAACAGGATAGGAAAAGTCTATCCAGTGAAAGTGGTGTTCAATCTAAATATTGAT TTGGTTCTTCGGTATTTCG |
| RMB06 | 504 | NO. 175 | ACATCGGTCGAAGAAGTTCCTGCATCAATTAGTACGTGGAGTTATCTTTTGTCTCTTTCTATAAGAGGCACTGGAAATC TCAAGACCATAACACAGCTCCACCAAAGCCTATATATGCTGGACTTAAGCTACACAGATATTGAGAAGATTCCAGAGTG CAACAATGGCCTTGACGGGGTGGAATACCTTTATCTAGCTGGCTGTAGAAGACTCACATCATTGCCAGAGCTCCCTGGT TCGCTCATATCCCTATTGGCAGAAAATTGTGAATCACTGGAGACCGTTTCTTCCCCGTTGAACACTCCAAAGGCACACC TCAATTTCACCAACTGCTTCAAACTGGACCAACAAACAAGAAGAGCCATTATGCAACCACGACCGTCTCTCTACAGGCT GGCAATCTTACCAGGAAGGGAAATACCTGCAGAGTTTGATCACCGAGGTCATGAGACCACCATTGGTCCTTTTTCTGCA TCCTCCAGGTGTCAGGCTTGCCTCAAGATT |
| RMB07 | 537 | NO. 176 | AGCTTCTATTCAGCCAAAAGGTTTTGATTTTGACCAATTTAGAGATTTTGTATTGGATTCAGTTGTACTTGTGCACAAA AAGAAGTATTGGAATCAGTTAGGGTTCTAGCTTTTGCAAAGAACTTTATTTTTCTTGTATCAGCTTCGATAATGTAGAT CAAACTGAATAAATGTTAAACAAAATAATTATTCAAAGCAAATACAATTATGCAGAACAAATGCACATTATATGTTTAT CAAACAATTTACTAAATATCATATATATTAAATGTTAAACTCATTATTTAAGGCTAGCACAAAATTTGTACGTGGAAAT TTATGCATGATATTCTTAAAATTCATGTCCCTGGCAATGAGCAAAACATTTTCTATTCCCATGAGGATTTTCATGAGTA TGTGGATGTGTATATGTACGTCCGCGACATCTGTATTTTTCATAACGTTTTCTGAAAAACAAAGAAAAAGAAAGATTAA CACAATTGAAAAACTAAAAAGTCAACTTGAAAATACTAAAATGAAATTTTCCAACGGTAATGC |

TABLE 1b-continued

| Rf Marker Sequences | | | |
|---|---|---|---|
| Marker | Size | SEQ ID | Sequence (5' -> 3') |
| RMB08 | 524 | NO. 177 | ACCAAAGACACCATAACGAGGGCCATGGGAAAAGGCACCGGCACGGTTGGCTAGATCGTGACTGGTTACCTTAGCAAGA TACGAGTTATCACCCGTGGCATAGTAGAGCCACGCTCCCCCCCATATGAGGTCATCCCAGTGATCTGCGCTTTTCCGCT TGGCGCTCATAGCCTCGGCGTAAAGGTAAACGGCTTTGGCACTGTTAACAAGTGTTGCAGAGTACTCGACTTGGTCACG GAATACGATCGAGGCTGAGGCCAGGGAAGCTGCCATCTCTGCAGCGAGATGCGGGCAGTCTGTGTAACATAGATTGACA GACCTTTGGTAATCAATGTCTTCTGGTCGCATCCAGCAGTATAGGTCACTAGTCACTTGGCTTCCTTGATTCATTCCTA TCTGTGAAAAGAAAAACAAAAAAAGTTTAGGACTGAACCGAATTGAGTATGCAAGAAGGAAGGGAAACAAAACTTTTAT ACCTGATACACCATTTCATAGATCGTATCAGAACTGCTGCTAAAAGTGCG |
| RMB09 | 316 | NO. 178 | CCCACTCTTGTTACCTTCAGCACCCTGCTCCACGGATTATGTGTGGATGTAAGTTTGAGAACTTGCTTATCTTTATTCA TCTTGCGTACAAGGTATATAACAGAGTTCTTGTTACAACAGATTTCTACAGACTCCTATATTACAGGAAGATAATATAT TTACAAAACAGATATGAGAATATCCGGAGTATATTCTTTCACCCTCCCGCAGTGAGAACGTCGGAGTCTCTGACGTTTA AGCTGGTTCTGAACGATCGGAAGAGGGAAGTTGGCAAACCTTTTGTGAATATATCAGCGTACTGGTAGGCTGTGGGAAC |
| RMB10 | 358 | NO. 179 | ATTGGATTTGAATGAGATGGAAGATTTGGTGTCGGAAAATGGTATAAACAAAAAGATTTGTTATGCAGAAAATCCCAAT GAAGCTATGTCCAAGAAGAGCTGGAGATGCAACAGCTGTTTATGCTTCAACTGAGAGAGCTGAGAAAGAACTCAAATGG AAGTAAGTCATTGGCTTTATCATTTTTCCGCATATAGATCATACAATCTTGCTTGTGAATCAAGATACAATAATATGTT CACTCTTTGCTACATAGAAGATTTTTACTGTTGGCATGAATAAAGGACTGATTCTTTGTGATTTTTGTTTTGTTTATTA GGGCACAATATGGAGTGGATGAGATGTGCAGAGATCAATGGA |
| OPF10 | 496 | NO. 180 | AACTTTTTGTGTTTGATTTCTTGCAGATTTGGTTCGGTGGCATATCTTCAGCAAATCTGGTGGTTTCAAGTGGATGGAG AAATCGATTTCCCGTTCCCAGCTGGAACCTACAGCGTCTTCTTCAGGCTTCACCTAGGCAAACCGGGAAAGCGGTTTGG GTTGGGAAGGTTTGCAACACTGAACAGATTCACGGTTGGGAACATTAAACCGGTTCGGGTTTCAGATTTGGACTGAAGA TGGTCAACACTCTTCGTCTCAATGCATGTTAACCGGATCGGGAAGCTGGAATCACTACCATGCTGGAGACTTGTGGGTT GGAAATCCCAAAAGCTCGTCGATGACTAAGCTTAAGTTCCTCCATGACGCAGATCGATTGTACACATACCCAAGGGAGG GTTGTGTGTGGATTCTGTGATTGTGTATCCGAGCTCGTGTAAGGACCGGTTGAGGCGGGTTTAAGTGTCTAAACCGATG TTTGGTTTTGTTTAGAAGGAGT |
| RMB11 | 317 | NO. 181 | AAGCTTGTCTCCTACGTACTTCTTCTATGTTCAACCGATAATGTCCTTGTCAGTTTTCTTGTATATTTGATTTTACAGT TGTTCTGAAGATTTTTATTTTTGGGTTCTTTATTGCTCTGAAGCTAAATTATCTTTTGTCGTTCTAATCTTTGTCATA TAAGCTCCATCAAAGTCTTGTCACTCATGTATCACTCTCCACATAGAAAGAGAAACACGAGAATTGATGTTTTTTTTAA TCGACGAATTGGATGTTTTAAAAAAAAAAAAATTCTCTTTTTTCTTTTTTGAAAATTTAGTGACGTGAAATATCTTTCTG A |
| RMB12 | 321 | NO. 182 | TGGACTAAGAAAGGGTCAGGTAATGGTTGTGGTTCTACCAAACGTGGCCGAGTATGGGATTATTGCCCTTGGCATTATG TCCGCCGGTGGAGTTTTCTCCGGCGCTAATCCTACGGCTCTTGTCTCGGAGATCAAGAAGCAAGTTGAAGCTTCTGGTG CTAGAGGAATCATCACTGATTCTACTAACTTCGAAAAGGTTAAGAATTTGGGTCTACCGGTAATATTGTTAGGTGAAGA GAAGATCGAAGGAGCAGTGAACTGGAAAGATATTCTAGAAGCAGGAGATAAATGTGGAGATAACAACAGAGTAGAGATT CTTCG |
| RMC01 | 356 | NO. 183 | AGGAAGTGAGAGGCAGTTGGCCTCGTCACGGGTTTTAGAGTTTAGAAAGCGTGTGCTTGAAAGTGTTCAGCAGCGCGCA TAGGATCATTGTGACAGGGGGAGAGTAGCTCGACCTGTCCTTGGGTAGATTAGGAATTGGTTCGTATCAAGTTCAGTTG AACGTTGTGTAATTCGAATTAGACAAGTCAAGTGTGATTGTCTAAGAGATTCTTAATAAAACAAGTTGTGTGTTTGAGT ATTGATCGAGTTCCATAAGGAATCGGTGTCCACTTGGTTTTACATTTGGTATCAGAGCGGGTCACCTCTGTGGACTCAC AGAGTCTACTCACAGGTTGAGATCCTAGGACACCCATGGA |
| RMC02 | 479 | NO. 184 | TGCGTAACACTTCTTTGCTTCACTCGTGAACAGCTCCACTCCTGGAACTAACATTCTCCCTCTTTTTATCTCAATGTGA CTTCCCTGCTACCTGCAACAGAAACACACTAGAACACACATTCTGACAGGCAACACGATTATGATAGTCAGCAAATCAA GGAGAACACCCCAAGAGATTATCCTTAAATTTCATCATGAAAACTAGGATATTACAGCCGATAGAAAAAGAGTTCACAG GTTCATGATAATTCAAATAAACACCGAAACAAGGATTAAACATCTGAGCAACAACACATTCATTAGTCGTTGTCTTGGT TTGCCGAGGCTGAGGTGCCACCGATGTCTCCATAATCTCCCCCTGCAGTGAAGCACAATGAGATAAAAAAACGAAAAGA AGTTAGCAAGATCAAGAGTTACCAAGAAACCTCCCCAGAGAAACCTTACTCTTGAGCCGAATGTGAATGGCTTTGAGTT CTGCA |
| RMC03 | 266 | NO. 185 | AAGCTTATTTTCATCCTGCAATGTCAACAACATACATAAATCTACTCAGCTTCTCTATACACATAACACAAGAAAGTAA ACACATATAGGCATAAGGCATGGTTGTTTTAAAAAGATATTTATAAGTATATACTTACGTCTTCAAAATGAAATATCAT TTATACTTAAATCACGTTTAAATACACTATTTTTACTCTTTCAAACAAATATACTATAGTTTACATAAACACAAATTTA ACTATATAATTACTGTGATGATGGTGATG |
| E38M60 | 116 | NO. 186 | TCCATAGAAGAAACTCTTTGCAACTATTTTCCTTTGAANAATGAAATCAATCGTCTCTTCCACAATTTGCAGAAACGTA AAATCTATTTACACTCTCAGATTAGTAAGTGTGTCGA |
| RMC04 | 213 | NO. 187 | TATTTTGTCCTCGGTTAGATCTTCTGTTGTACATTCTGATGCTCAGAGTGAGAGTCACACATACATTTTCAGTTTCTAG GTTTTGTCTGTGATTCTGCAAGTGATGAAGTTATTGGTTTGGTGTTGAGCTTTTTATTATGTGTGTGTCTCTGTCTTCA CGTTTTGATGTATCTGCTGTTCGTTTTTTTAAAACCCTAACCAAACACAAAGGAA |
| RMC05 | 500 | NO. 188 | TGCGAGTTTAATCCGGACGCCAAAGACCTGACGAAGCTCGCCAAGAACATAGATTTCGCGTGCACTTTCTCGGACTGTA CCGCGCTCGGTTACGGGTCTTCTTGCAATGGTCTGGATGCGAACGGGAACGCTTCGTATGCGTTTAACATGTATTTTCA GGTGAAGAACCAGGATGAGATGGCTTGTGTGTTCCAAGGTTTGGCCAGAGTTACAGATAAGAATATATCTCAGGGACAG TGTGAGTTCCCTGTTCAGATTGTTGCTTCTTCGTCTTCTTCTTCTTCTGTGTCTCTTTTTGTTTGGTTGATCATCGCTG GAGTTTTGTTTGTCTTGATGTTTTGAGGTCCCTTATTGATTATATATATTTCTATTTTGGTCTATGTGATAATATGTTG GATTTGGGTTAATCGTACAAGACAAAGACAAAAACAAAACATTGTTGAAATAAGTCTAGCATGTAAGTCGGTTAATTTG GTTATCTCTGAACCAGAATAACGCGG |

TABLE 1b-continued

| Rf Marker Sequences | | | |
|---|---|---|---|
| Marker | Size | SEQ ID | Sequence (5' -> 3') |
| RMC06 | 482 | NO. 189 | TTCCTCGGCAAGAACAACGCACCGATCACGATCAACATCTACCCTTTCTTGAGCCTCTACGGTAACGACGACTTCCCGC<br>TCAACTACGCCTTCTTCGACGGTGCTCAACCGATAGACGACCACGGTGTTAGCTACACGAACGTCTTCGACGCCAACTT<br>CGACACTTTGGTGTCGTCTCTGAAAGCTGTTGGTCATGGAGATATGCCGATTATAGTAGGAGAAGTTGGCTGGCCAACA<br>GAGGGTGACAAACACGCTAACACCGGTAACATATCTCTGAAACTAACATAGTGCTCAGGCCGTCTCGAATTATTTATGG<br>ACCATGTTAAAAAAATATTAATGATATATTTAATATATAATAGAATAGTTTTAAAAATTTATAGTTTTATATTATAACT<br>TATATATTTATTTTAAAAATTCTTAATTTTTCTTTTGTTTTTCAACTTGGATCATGTTAGTTCCGTTTGCACCTGCTGT<br>TAGACGGC |
| RMC07 | 466 | NO. 190 | CCGTATTTGAAAACGTGGCGATCTATAAGATATTTTGTATGCGTCTTCCCGTCTTCCGAATTAATCATATAGCATTTTT<br>GTATGGAACAGGGAATATACATGAAGGATAAGTTCTGAGCATCATTTTTTTAAGACTGATTCATAGAACTAGTGATGTT<br>GTGTTACTTGTCGCTTCTCTTGGTGCTCACGACTTTGCATGTATGGCTTTCTTTTGATCTGATGTTTATATCTGCTTTA<br>GGTTTTACTTGGAGACCCAAGGGCAGGATCCAATCAGCCAGAGATGCAGAGCTCTATTGTCTTCCATGCAGGATACGTT<br>GATTTTGTGAGTATTCCTTTACTTGTATGGGTTTTTACTCTCACGTTGTCTTTACGCATGATTTCAATATTACATTTTC<br>TTTTCTAGAATCTGATTTGAGAGATTTCCCTTGGCACCGTGTTTTCATATTCGACCCAAATTCACGGTTGA |
| RMC08 | 547 | NO. 191 | GAGGCGAAAACATAAACAAGGTTCAAACAAATAATTGACAATTCTTTGGACATACAAAAAATTATTTAATTTTTCCAAA<br>TAAAACATAATTGTTGAACTTTTTTTTGAACTGAACATAATTGCTTAACTTAAGAAGTAAATCTATTCATAATTGAGTT<br>TTAACTGCAATTATTAAAAAAAATTTTGTAATATTTGATCAAATATCAAAATATATATTAAATTAAAATACTGAATGGA<br>TTATACATTTAATAGTAAATATTCGGTTTGGTATAATATTTTGGGGAGAAATTTTAACTTTACTTAAAATTTAACATCA<br>CTTTTTAAATGATAGTTATGTTTATAAACATCTTAATGTGATATATTCACTAATCACTGACAAGAACATGTGTTACAAA<br>CATCTTAATGTGATATATTCACTAATCACTGACAAGAACATGTGTTACAATTCGCTGACAGCTCTATTGCCATCCATGC<br>GCGATACGTCAATTTGCTTTACATTTATACATTTGCATTCTCTTCTTCTTTTTCCTGAAACAGTTTTGGCGAT |
| RMC09 | 327 | NO. 192 | TCGGTTTTTCGAGGGTATCAAATTTAATTCTATTAGGATATTCTTAATTTTTAGGGAAATTAAGCCTAATAACAAAAAA<br>ACTATAATTCACTAAATAACAAAATCCTCACTCTCACTCCTACTTTTCTTCTTCCTATTTCTCTTTACTCTCATTCCTA<br>AAAGTTAATTTCCATTTTTTGGGTTATTTGACAAATAAACCATAAATTTTAATTCGGATTCGTTTTAAGTTTTTTCCCA<br>ATTCAGTTCGGATATAGTAACACATCGCAAACCCAGCTGAACCCACTAACACCGGATTATGTTCTAAAACAGGTTCGAT<br>TCTAAATCGGA |
| RMC10 | 466 | NO. 193 | TCCTGCAGTTTGAAATCCTTGGTAAATCCAATGATTTTAATATCAGACAATTAGATTTTAAAATAAATCAGATGAACTT<br>CAAAATCAAATCAATGGATTATTATAAATCAACAAAATGGATTTGTAGTATTAGTTTATGATAAAGTTAATAAATATAA<br>AAATATATCTTTTTCATTTTTTTCTTATATGTTCTCAAATTCTCATAACATATAGAATATCCCCACCTATTTGTTGTAA<br>TAGTTGTTCTTAACTGATTGATATGTTCTATATGCTGATTTTGGTTACAAGAAGTCAAGAACTTCTTCATCATTATTAT<br>TTTTAGATTTTTTTCATCATCAAAATCTTTTTTTTTGGGGTTATTTGTAAAAAATGTGTAATTAAAAATATAATTTTTT<br>GAACTAGAAAATATGATATTAAANATAGTGATAATAGAATCGAGNACNCGGAAGTTGGTTTGGGGAAACTT |
| RMC11 | 273 | NO. 194 | AAGCTTAATAGCGACTTCTTCGTTAGTCTGAACATCAGTTCCTGTAACCACCAACAAGAGTCATCAGAGATTCAACATA<br>CCTAATTGACGCCTAGTCTAGTCACACATGAATGAAAGAAAAAGTAGAAGAGTGAGAGAGTGAGAAGAGGAAGAAGGAA<br>CCGAGGTAAATCTCTCCGAAAGAGCCGCTCCCGATTTTGCGGCCAAGTCGGAACTTATTCCCAATACGAGACTCCATCT<br>TCCCGAGAGAGAGAGAGAGAGAGACTAGGGTTTTCA |
| RMC12 | 347 | NO. 195 | AATGGATGAACTCGAGACGGTTTATCTGACACAAGAAGCAAAACAAGTTAATCCATCAGTGAAAGTTGTAATAACAATT<br>GCAATACAGTGTACAAAGCAAGAGATACCATTTGATCAGCAAGCATGAGAACAGTCTTCAAAGAAAACTTGCGGTTGCA<br>ATAGCCAAAGAGATCCTCAAGGCTAGGACCAAGCAAATCCATGACTAAGACATTGTAGTCACCCTCAACACCAAACCAC<br>TTAATGTTTGGAATCCCAGCTGGGCATTAAAAACGCAAAAAAGAAAATGAACAAAACTAATAATAAACTGTAAAAAGAA<br>GAAGAAGAAGACAGGAAACGAGGGGTTATCA |
| RMC13 | 382 | NO. 196 | TGTCAGCATTCAGCAGAAGCTTATTATGAGTTTAATAGCCGGAGAGAGGAAATGAATTAAACCTTCACGAATGAAAAGG<br>TTGCGGAAGAGTCTCTTCAAATAAGCATAGTCTGGCTTATCATCAAACCTAAGTGAGCGGCAGTAATGAAAGTAGGATG<br>CAAACTCTGTTGGATGACCTCTGCATAACGTCTGAAAATAACACGGACTCAAAGTTACATTTCTATCTATATAATCAAC<br>CTTCTCTACTTCATCATTATTTCCTTCGTACATAGACTCATATAAGTTTCTGAGAGTGCACAAGAACTTACTTCGATGG<br>AAGTAGAAACCTTCTTTTCACTAATCTTGTCGTATTTCTGTTTCTTGTTCCCAGCTTTCAATCCCT |
| RMC14 | 533 | NO. 197 | TTGACGGTTACCCAAAATACCGAGAAAAAATAATAATAAGCCTTTGAATGTAAATGCATTTTATTCATGATGATTCAAC<br>ATTTCAAATTCAGGATAAAGAAATATAATAAAATAATAAATTCAAACAAAAAATAATAATAATAGATAATTACTAGTAT<br>TAATTTATGTTGATAAACTATTTTACTCATAAACTTTCGTTGAATATGCTGTTTTAGTCGCAGTGTTAATCAACCATTA<br>TAATTGACAAATAGTAGACCTAAACTGACTTTAAAGTTTTTATTTAGCAAAAACACTTTTTCCACAAAATGGGTTTTTA<br>ACTTTTGAAATAATTATCAGAGATAAGGAACTTAAAATACTTCGGTTTGTTTTATCTATACAATGGAGAAGACCAATGA<br>ACCATATAATTTAAGCACTTTGGTATAAATAAATCTCTATCCCTCCCTTATATCAAATCTCTAACTTCAAAGCCTTTCT<br>TCAGAAGAATCATAGACTACCTTCAAATCCTCAAGAAGGGGTGAGGGTGAAGCAATCAA |
| RMC15 | 711 | NO. 198 | AAAGCATCCTTTGCAAGGGGATCTTCTATATGCTATTGAAAGAGTGTTGAAGCTTTCAGTCCCAAATCTATACGTGTGG<br>CTCTGCATGTTCTACTGCTTCTTCCACCTTTGGTATGTATGCCGTGATCCTTTCTCCAAAGATGAACAACAGAAAAAGG<br>ATATATCTCATGAAGAAATTGATAACATTAGTTTTCTCACACAGTTTTGAGATGTAATTTCAGTTTCTGATCACAAATC<br>TCTTTGCATTGTGTTCTTGTCCACAGGTTAAACATATTGGCAGAGCTACTCTGCTTTGGGGACCGTGAGTTCTACAAAG<br>ATTGGTGGAATGCAAAAAGCGTAGGAGATGTGAGTTGTCATTAACCTTTTGTTACTAAAGAACATTGACGTTTTATGTT<br>GTCACACATGACTAACCAAATTTCATGTATTCACTTTCTTCCTTTGTCAGTATTGGAGAATGTGGAATATGGTATGGCT<br>CTCTTCCTAAAACATCGTCGTCTTCTTTTCTATACGAAACAGAAGCAGAAAGCTAACGGAGAGCTTTTTGTTTTTGTTT<br>TAACAGCCGGTTCATAAATGGATGGTTCGACATGTTTACTTTCCGTGCCTGCGCATAAAGATACCAAAAGTGAGTGTGT<br>ATATGTAGATTAGTGATTTGAGATGATCGAGATTGTTTTCTGTGTTTCATAGCTTTAACCATCCACTCATTTTTGGTTC |

TABLE 1b-continued

Rf Marker Sequences

| Marker | Size | SEQ ID | Sequence (5' -> 3') |
| --- | --- | --- | --- |
| RMC16 | 400 | NO. 199 | AAATTGTTACAAAGTATGAGAAATGAATATATCAAATCATACTCTTAAAGTGATTTGTGTTTGGTTTCAAAGTGAATGA<br>ATTTATTGAAATAATTTATACAATTGAAAGGGAAAAATAAGCTTATCTTATTGGCTCTCTGCATTTTAATAATTTATTG<br>AAATAATCTATACAATTAATAGGAAAAAATAAATTTACCTTATTACCTTAATTAATTAAACAAAAAATAAAAATGTATG<br>CATGTGTTATAATACATAGTATTCAACTATTACCAGCATAATTTATATTTAACTATTTTTATTAGTATTTTATAAAGGA<br>GCCTAAAATTAATTAAATAAAATATTAAAAATGCATGCTTATGTCATAATATATTTGTAGAGAATGAGTAAAATGTTTA<br>CTGAA |
| RMC17 | 554 | NO. 200 | TTTCCACACAAATCGGATTTAATAATTAAAAATCCAATAAAACTAAAATATTTGCTATTAACCTGTTAATCTACTCTGG<br>CAAAACCTAAAAGAAAAACTTATAATACTTTTTGAAAAATTAAATAAACTTCTCTTATACTTTATATAAAGTACATAAA<br>ACTAAATAAATTATTTGATTTGTCATAGTATATTTTTAAATTACACATAAAGAAGAAGGTTTGTTTGTTATTAGTTATT<br>CCTTTCATATATATATATATCTATCTTATTAAAACAGGAACATTACAACTTTTTCTAGGTGGATTTTTAAAGATGGACC<br>TCATATATTTAAATTAAATGTCTCATTCTTTATATATAATATGTACCATACTCTAACTTTGCATTGATGTATTTCCTTA<br>AATACAGTTCTTCTTTTTGTCCATATTCCATATATGATTTTTACATTTATTACATGTCGATTTAAATAAGATATATACT<br>AAGAATACTAAAAATATTAATCGTTCTATAATTACCCTATACAATTCATTTTAAATTGATCAGTAAACTTTCATTGGCC<br>A |
| RMC18 | 525 | NO. 201 | ACCAAACCGAGAACAAAATAGGTGTCTAAATTTTTAAAATACAAATTATATTCTTTCAAATATTACGTCTATTCGATTT<br>CTAAATAACCGAGTATCCTGAAAGTACTATTTATAAGCTAAATTATCCATAAAAATACCAGAATATTGTTTTCAAAATA<br>TTTAAAGTATTTGCATTATCTGATATTTTAACCCAACAATATGAACTACCTAATATTAAATTGAAAATCCTAAATTATC<br>CGATATATTTATCTATAAATTCGTGATTACCGGAAAACTCAGGACAAAGCAAAACTGAATTGGACCTATATTTTTCTGG<br>AATATTAGTCGGTTTCCAACTATACTACTAAAAAACAAACCAAAATAACAAAATAACAACACAACTAAAACCAGACCAT<br>TTTGTAAATAATTGAACGGTTCCTGAATTTGTAGAACCATAACACAACTAAAACCAGACCTTTTTGTAAATAATTGAAC<br>GGTTCCTAAATTTGTAGAACCAAAACACCAAAAAACCAAAGTATTCGAACC |
| RMC19 | 543 | NO. 202 | TGGAGGTGTCAAAGTGTGGCATCACATAAGAGTTTTAAGAGTTTGTTGTGCTTTAGTTTTTGAGTGAGTTTTCTAAGGC<br>AATAAGAAGAGTTATTTCTTTACGAGCAAGCTTCTTAGTTTCTTAAGTTCTCTGTTTCTACAGATTTTCTGTTTATATT<br>ACTTACTTGAAATATTCTTTTCCTATAAATTCTTATGCAAATTTTCAGAACAATCTTGTCTGCAGATACATTTTGATTT<br>TATAGTCTGCGCAAGGCAAATACAGTTTTGATTTAATGATACAGAACAGAGTGGGTTAGTTCCAGGTTTGGTCACGAAC<br>AATCATCTTTTACATTGGTCTATGTAAATCAAGTCATATCCAGAAAGCAGATAGGCTTGTTTAAGAGATGTGGGAGATG<br>GGTATTTGTACACACTGAGTTTTTTATAACACTTTTACCAAGGGTGTTTCTAGTGTTAACAATATCGATAAAGATCTTA<br>GATCTCTATCTCTTCGCTACTATATGGAGAATAATCATCATGGTATTAAGCCAAATAAAGTGACTTGCG |
| RMC20 | 463 | NO. 203 | GAACCACGACTTTGGGTCTGANATTTAACGGGACAGAACAGAGTATACCAAGACTCATGGGTTACAGTGACTCGTCTTA<br>TAACACTGNTCCANACNATGGGAAGAGCATCACAGGCCATGTATTCTACCTCAACGACAGCATGATCACTTGGTGTTCA<br>CAAAAACAAGAAATTGTTGCATTATCATCATGTGAGGCAGAATTTATGGCAGGTACAGAAGCAGCCAAACAAGCTATAT<br>GGTTACAAGAGTTACTCGGTGAAATCTTGGAGCAGTCGTGTGTAAAGGTGACTATACGGATCGATAATCAGTCTGCTAT<br>CGCTCTTACCAAGAATCCGGTCTTTCACGGAAGAAGCAAGCATATACATTCACGATACCACTTCATAAGAGAATGTGTT<br>GAAAAGGGACTGGTGAGTGTAGAACATGTTGCAGGGAGTCAACAGAAAGCCGACATTCTAACCAAAGC |
| RMC21 | 269 | NO. 204 | GAGAATATTGGAAGAAAGCGGAATGAAAGACTGTAACTTGGTACACACGCCAATGGAGTTAGGACTAAAGCTTTGCAGA<br>GCCGATGAAGAGGAGGAGATTGATGCTACAATATATCGAAGAAACGTGGGGTGTCTTAGGTATTTGCTTCACACCAGAC<br>CGGACCTAGCTTATACGGTTGGAGTTCTGAGCCGTTATATGTCGTCACCTAAAACTTCGCATGGAGCTGCCATGAAACA<br>TTGTTTGAGATACCTCAAAGGAACCACGACTT |
| RMC22 | 747 | NO. 205 | GCTCTACGAGTGAGGATCAAAGTCACGAGAATATGATCAAAGCAGAGCCTGCAGAAACAGAAACATTGAAGAAGAAGAC<br>AGTCATGAGAATCAAGAACCTGAAAGTGAGAATGAAGCGGTACCTCTAAGAAGAAGCGTGAGACAAACCATGACACCTA<br>AGTACCTGGAGGATTACGTTATGGTTGCGGAAGAAGAAGGAGAGTTGCTGTTGCTAAGTATTAACAACGAACCTATTAA<br>CTTTGCAGAGGCAAGTGAGCGTGAAGAATGGATAGCAGCCTGCAAAGACGAGATAGCAAGCATAGAAAGAAACAGAGTA<br>TGGGATCTAGTTGATCTTCCACTCGGAGTAAAGCCTATTGGTTTACGTTGGATCTTCAAGATAAAGCGAAACTCGGATG<br>GATCAATCAATAAGTTTAAAGCTCGACTGGTTGCAAAAGGGTATGTACAACAATATGGAATTGATTTTGAAGAAGTATT<br>TGCACCGGTGGCTCGTCTTGAGACTATAAGATTGCTTGTGGGTATAGCAGCTGCAAAAGGATGGGAAGTACATCACCTA<br>GATGTTAAAACGGCGTTCTTACATGGAGAATTAAAAGAGACCATTTATGTAACTCAACCAGAGGGCTTTGTGGTGAAAG<br>GAAGTGAACGAAAGGTGTATAAACTCAATAACGCATTGTACGGATTGAGGCAAGCACCAAGGGCGTGGAACCATAAGTT<br>GAATACTATTTTACTTGAGCTTGGATTCCGAAAGTG |
| RMC23 | 219 | NO. 206 | AGCTTATAGGCTTCTAGACCCAAAATCTCGAAAGATAGTAGTAAGCCGAGATGTTGTTTTCGATGAAACTAAAGGGTGG<br>AATTGGGGTGAACAAAACAAGGAAGATGAAAATTTTACTGTCAGTCTTGGAGAATTCGGAAATCATGGTATTCAAAGCT<br>CTACGAGTGAGGATCAAAGTCACGAGAATATGATCAAAGCAGAGCCTGCAGAAACAGAAAC |
| RMC24 | 363 | NO. 207 | AGCTTTAATTCATGTATTTTTACAAATTTTGTTACTAGAAAAAAAAAAAATTTAGTATTAATTAAAATAATTAGTGACT<br>AGTCAATTTTACTTATAACAAAATCTTTTTAGAAAAAATAAGAAAATCTTTAAAAAATTCAAATATATTTTTAGAAAAT<br>ACTGAATTAGTTTAGTAACAAAAAAATCAAAAATCATATAATCTTCCAAACTAAAAAATAATTGTGTAATTTTCTAAAT<br>GCCTCTTGACCAAGTATACAATTTAAAAAATAAATTAAAACTCAAAATGATAATATTCCAAGTTTTATAAAAATATAAAG<br>TCATACAAGTTAAAATATAAATTTTTGAAATGTATCACAAAAAAATT |
| OPC2 | 678 | NO. 208 | CTGTAACTTTCAACCCAACTCGTAGAAGTAAGGACATCGTGATCAAAGATCCACACATGCTTGATCAGCCTGCATCTCC<br>AACCTCGTCCTGAATAAACACACACAGAGCTATGAAAGGGTACAAAAAAAAACAAGTACTTAGGCAGCTATCTGGAATC<br>TAAACAGTTCAAGAAGGTTCTAGATGAAAACCCTAAGAAAGAAAGAAAGATTCTGAATGCCACTCAAAGCATTAACAGT<br>AGGAAGCTGACTTACTTTTGACCGAAACAGGCAGGAAGGTTAATGGAGGGGCACATGTCAATCACATAAAATAAAATGA<br>CACTTAACTTACATTAGCTTTAGTGGCCTCTGAAGTAAAGTATGTGGTGAGGAGGCCATTCAGTTTGGGTATAATATCA<br>ACTCTGCCACGGGATTGTCTTTGAGAAGACCCGTTGCTAATACTTCTTCCTGAAAAAAGCCAATTAACACAAGCTTTGA<br>TACCCAAAGACATAATTAAGATGTGAAGATATGGTTCATAGATAAGCTTTATACCTTCATTGCTTCAGATCTTGAAGGT<br>GCGTCAACAGCAAGAACAGCTCTTCGAGCTCTTCGCACAGTCTGTCCTACCAGTTCATATGGCAGCAATTCTCCTCTAT<br>GCTGCTGTGTGAACCTGAAGAAAGCTAAGAAGAGTAATCCCCAAAA |

TABLE 1b-continued

| Rf Marker Sequences | | | |
|---|---|---|---|
| Marker | Size | SEQ ID | Sequence (5' -> 3') |
| RMC25 | 364 | NO. 209 | AAGCTTGATCAAAGATCACAGTCTTACAAAGAAACAGAAAACAATTTCAGTGAAAGAACAGTATTTACCTTATTTACTC<br>TAAAATTTTTAAAACAGATTTTTTTCATGTTCAGTACCAACATAGATGGAATCAAAAATATTATTAAATCATCATACTC<br>CATCATGTATTACAAACTGGTGGATTTAGTATTTTTGAAGACCAGACATATGCTTAAAATCATAAGATTCCCGTTACTG<br>CTACTGTGCTACACCAGTCTAGCCGGTGACAGACACATAGCTGATATTGAAAGTTCCTTGAAGAACAATGAGTGTGGTC<br>AGAAGTTGCAATTATATTGTTTGCAAACCTGTTGCTCATTAGTTTGTT |
| RMC26 | 201 | NO. 210 | CAGACCGTTCAAGTTCATGGCGAAGAGAGAAAGAGGGTTCAGTTTCGCATTGTTGACGAAGAGTTTGTTTTCACAATTT<br>TTTTATTTCGTTAGCTTATATACGTGATATTGGTTGCTTAGTTTAATAGTTTATATGCTTTTATATTGACAGAGGAAAC<br>AATATTGCATGCTGTCTTTGGGGATCATATGCCGAGCAACTTG |
| RMC27 | 238 | NO. 211 | CCTTCTCCAAACCGGTAAACGGTTAGCCACCGCCGCGTCCCGTCGCCAGAGCATATCCTTATCCGACGACAGCTTCATC<br>CTCTTCTCCTCCGCCGACGCCGCTTCCTCTTCTCTCACCGAATCCGAAAGCGTCGCTCACGTGCTATCTCACATCAAGC<br>TCCTCTTACGACGGCGCGCCGCCGCACTCGCCGCTCTCGACGCCGGACTCTACACCGAATCGATCCGTCATTTCTCAAA<br>A |
| RMC28 | 623 | NO. 212 | AGACCAAGAGGAAGCGTAGCTTCCGCCTTCCCCTTCCTGATGTTATGAGTGGTCCTACGATATCCATGGACCACTTCAT<br>GAACGGGACGGAGCGGATATTGAGGATAGTTTTTCCGCAGGCTGATGTATAATCGGTGTATGCCTTTGGCATTTATCAC<br>ATGAAGAGGAGTAAACCTCACAGTCAGCGATAATGGTGGGCCAGAAATAGCCCTGTCTTTTGATTCAGATAGCTAGAGC<br>TCTGCCCCCAAGGTGGTTTCCACAGGAGCCGTCGTGCATTTCTTTCATAAGATTGATAGCATCGAGACCATGGACGCAT<br>TTTAGGTAAGGTCCGGAAATACTTCGTTTATGGAGGGCTGACTCGATTATGCAGTATCTTGCGCTTAATGCTTTGAGTT<br>TTCGGGCCTTACCCTCCAAGATGTACTGCATGATTGGTATTCTCCAATCCTCTCTCCCAAAGATTTTTTCATGAAGAGA<br>TGAGGGCGGGTGTTGTTCAGGTCCCTGTGTGTCGTGACCTGATGTCTTATTGCCCCCGGAGATATTGGTCGGATTAGGC<br>TCGAAGGAGTCTGAATTCTGAGGAATATCTCCAGTTCTGGTGTTGTTCTCCGGAGTCTGGGTTGTTTCTT |
| RMC29 | 198 | NO. 213 | CAATGATTTATACTTCGTTTTTGCTTTTTTTTTTTGTTTTTGNGAGCAGGTGGATGCCGTGGTGTACCTAGTGGATGCA<br>TACGACAAGGAGAGATTCGCAGAATCGAAAAAGGAACTGGACGCACTTCTCTCAGACGAATCTTTAGCCACCGTCCCCT<br>TCCTCATCCTAGGAAACAAGATAGACATACCGTACGCTGC |
| RMC30 | 525 | NO. 214 | CATTTGGTTTGTCCGTGTGTCCCATATGATTCAAAATCTGAGAGCTTATTATGTCTATATAAAACACCTTATTAAAATT<br>AAGGTCAATATCTCATAGGATTGTGTATAGATTCGGCTGTGTGTACTTAGCTACTCAAGTAATTAGAGCCCCACTTATC<br>TTATCCACTTTCACTAATAAATCACTCGTGCTTGAATAAAGAAGCTGGAACCGCTTAATTTTTATCAAAATCAAATACC<br>GGTTTAACAGCCGCCGAGATGCACATTCTCGACACCGGAGCTCGTTTCTCCGCCGTTAGATTCTCACCGGTATTCAATC<br>CTACTCCCCGCAGAAGATACGTCATCGTAAGGTATCTTCTTCATTTCTCCATCTTCTTCTACTTCACACTGAGTTGTCT<br>CTCTCTCGCTGCATCCAAATCATTGAGTCTCTCTCTCTCTCAGGGCCAATCTCCCGTTTCCGAAGCATCAAGCTAAGTA<br>CCACAAAGAGCTCGAAGCCGCCATCGATGCTGTTGAAAGAGGTTGTCGCCT |
| RMC31 | 379 | NO. 215 | CATTTTCTTTAACAACGCGCTTTTGATTTCCATTGACCGTACTTTGAAAAACACTCAATTCGGCCCATCACATGTCATA<br>CCTTTTTCTCAGCAATAGTTCATTTCGTATTTTATTAACTATTTTAGCTCTGTTCTGATCATACATCTATATATATGGA<br>TCATATACAATATGAAATAGGAGTCAAACATGAAGCTCCGAAGAAACAAACATCCTAAGCAGCAACGGCTAGCAACATA<br>GCCTAGTTGGCCACCTACTTTAATAGTTTTAAACGACGACTAAGAAAAATATAAAATGAGCACACCGTCTTTTAAAATA<br>TTCCATGTGGTGATGTATCCACGGTTTGCACACCTTCCTAACCGTACTACATGTCGCCGTCGT |
| RMC32 | 446 | NO. 216 | TCTCTCACACTTTCTCTCACCAGATCTAAAGCTGACCACAGTCAGCGATCACAACCTTCTTCGAGGTCCTTCCACTGTC<br>AGATCCAACCTTCTCAATGTTCCTAACGACATCCATCCCTTCGACAACCTGACCGAACACAACGTGCTTCCCATCCAGC<br>CACGACGTCTTCTCAGTGCAGATGAAAAACTGAGATCCGTTCGTGTTCGGACCAGCGTTGGCCATGGACAGGATGCCCG<br>GACCGGTGTGTTTCTTGACAAAGTTCTCGTCCTTGAACTTCATGCCGTAGATCGACTCTCCCCCGGTCCCGTTCCCGGC<br>GGTGAAATCTCCTCCCTGGCACATGAACTTGGGGATCACGCGGTGGAAGGCCGAGCCCTTGTAGTGGAGCGGCTTTCCG<br>GATTTGCCGACTCCCTTCTCNCCGGTGCAGAGGGCGCGGAAATTCTCGGCG |
| RMC33 | 275 | NO. 217 | CAAATCAATACCATTAAAAGTGGATCATTATCATTTTATACCATTAATGAAAATTTCATGTTTTTCAAAAATATCCTAA<br>TTTTACAAAGGATTATTAACTTTCATTAATAGCATTTTTGTCTTTTGATTTTGGTCATGCAGACATAAATTTAAATAGA<br>TCAATGAATAATGAGCTTACACATACTTACTTATAAAATATGCTATTTTTTATTTTATATAAATATTCTAATTTTAAAT<br>ATTATACATATATATTGTGAAAGGAAATTAATCAAAAA |
| E33M47 | 122 | NO. 218 | AATAGAGGGAGAGGATGAAAGAACCACAACCGCATACAGATACACATGTGTTAGTATATGAAAACGCACGTATGTTTTA<br>TAAATAAAATCCCTTACTTTATAACAAAACCTGTTAGGTAGCT |
| E32M50 | 252 | NO. 219 | TCACATTAGTAAAACGATTGTCCACCCAATTATAACCAAAAGCGGATCCCTATTCGTTACCCGTAAACCATAAACACAT<br>TTTTTTTCTATTTTCTAAAACCACACGATGTATCTCTTCTTTTCTAGAATTAGTGTTCATAGAAAGTGAGTCATGATTA<br>CTTTTCAAGACGAAAAATCGATCTGAGGAAGTTTTCTAAGATGAGTACGTGCGGTTCCTTTTTAGGACCACAAACGGAG<br>TCCAAAAAATCAATC |
| OPN20 | 587 | NO. 220 | CCTTAGTTTAGTTGTAGGTGGTGGAAACATATATGGACGACGGTTTCTGTTCTCACCTGTCGTCTGTTTTCTTCTTAAT<br>TTTTGCTCTCAGATCATCAGAGTTTGGTGGGAATGGTTAAATCGGACACTTCCTTATTTGGAATTTACCATTGGGAAGC<br>ATCAGAGGGAGGGAACTGAGAGTATGCTTGGAGGGATGGAACTGTCTTGTGTAGCCTTCTGAATCAGCTTAGTCCTGGT<br>TCTGTGACAACGGTACTTATGAATTTCTATTTACTAGGATAATGTACCTTGTCGTTTTCTTTTTTTTTCTTCCTTGTCT<br>TTGTCATTTGTTGCTAGCAGGGCCGGCTCTGAGAATTCGGGGGATATAGACGGTTTAAGAAGGAATTTATAAATTTGGG<br>GGCTGAAATTCCTATTTATATAAACTGGGGGTCTATCCATATATAATTTTTCAAAAAAATTTCGGGGGCTTAAAGGCTA<br>ATGTCTCATCCGGCTTGGCTCAGGGCCGGACCTGGTTGCTACCCTCACACTCTTCGGATATTTATATAGGGAGGCAGCT<br>TTGAGCCTGCTTATGTTAAAATTGAGCGGTTTCT |

TABLE 1b-continued

| Rf Marker Sequences | | | |
|---|---|---|---|
| Marker | Size | SEQ ID | Sequence (5' -> 3') |
| OPH15 | 637 | NO. 221 | CCTTGGCTATGTGCTTATGTATTTTCTTCGTGGAAGGTATATATCTGCTTCCCATTTGCTTTTATTTGGTTTCCATTTC<br>ACCTTACCCTCTGTTTCTTCTTGCTAGTCTGCCTTGGCAAGGCCTTCGTGCGGGTACGAAGAAGCAGAAGTATGACAAG<br>ATCAGCGAAAAGAAAAGGCTTACACCCGTTGAGGTAATTAGTCTTAAAAGGCACCTGAAGTGTCATTTACTTATCAAAA<br>GATATAATTTATTATCTCCATTGACAGGTTCTCTGTAAATCCTTTCCACCCGAGTTCACATCGTACTTTCTCTATGTAC<br>GATCATTGCGGTTTGAAGACAAACCAGATTATCCATACCTAAAGAGGCTTTTCAGGGATCTTGTTCATCCGAGAAGGTT<br>GGGGAAAACTACTTATGCTTTAATATTTCACATAAACACACAATATGTAAAGTTTTTTTTATAATGTTATAATATATTT<br>GCAGGTTATCAGTTTGACTATGTATTTGATTGGACAATCTTGAAGTATCCACAGTTCGGTTCAAGCTCCAGCTCCAGCT<br>CCAAACCAAGAGTAAGTAACTATCATTTTCAATTCCTCTTGAGCATACTATCAAACAAACCCTCACGATTGTCTCTGTG<br>TTTTA |
| IN6RS4 | 235 | NO. 222 | CATTGATACATGAATGCAAAGAAGAAAAAGTCCAGACCTTTGTTCACATTTTGGCCTCCAGGACCACCGCTTCTAGCAAA<br>GTTAAGCGTAACATGGTCTGCAAGTATATACCAAACAGATAAACAAATGAAACCATGAGTATGAACAGATCGAACTATA<br>ATTGTAATTCCATCAAAATCAGTATAAAATAGAGTTCTATAATAACATTTGTAGCATTGTCTGTAAATGTTTTCATC |
| E33M58 | 281 | NO. 223 | CTGCATAAAATTATCGAAGACAGATAACACAAAGAAAGGACATAATTGTTACATTGAAACAACATTGTTATTGTTACAT<br>GTAATTCCAACCCACTGGGTTCCACAAGGATCAGAGCCTTTCCAGTTCTCAGGAAACCTGGTCCATTCACTCTTCAAGG<br>CTTGTAATGCAGAAGCTGCGCCAATTTTGAAAAGAAATAAAATATTCCTATATCTGTCTGAATAACTCGGATCATGATC<br>TAATATACTTACCGTCTAAAGGATTTGTTAGCGCTGAAACAGAA |
| E32M59 A | 406 | NO. 224 | CTTTGTCATTGTGTGTGTGTGTGTGTGTGTACCGGGCCGATCTTTGTCATTGTGTGTCATTTTTAGCTGCAACAATGCA<br>TTTGAAAAAGCTGGAAAGAGACGAGAATCTAGTGGCTGCATTCTCTTACATCCATTGTGGATGAGCTCCAACTGTCCAA<br>CAGGCTTTGAAAGAGTTTGGTATAAATGATTCACATCTTGATGAAATGATCAAAGACATTGATCAAGACAATGTGAGTA<br>GCTATCTTTACAGCTTTCATTAGAGAGATGCTTATGGTGTATGGTTTTTGTAGGATGGACAAATAGACTATGGACAGTT<br>TGTGGCAATAATGAGAAAAGGTAATGGCAGTGGAGGGATTGGTAAGAGAACAATGAGACACACTCCACTTGGCAAATTG<br>GAAATCATATT |
| E32M59 B | 350 | NO. 225 | AATTCTTGCTCCATTATGATTTCACCAAGTCAACAAAATCTTCTTTCTACTAGTGCGATAGATCACTAAGCAGCGTAGT<br>ACAACAACCACATGGGAGGGAACACGATAATGAACAAACCTGTTGAATATTGATGCGGCGGGTGGGTGCTCAAGAAGCT<br>TACTCGTGAAATCGAGTCTTGCAAAGAAACCTAAGCTGAGTGTGAGTAATGAATTTATACATAAAATATAAATGGGCCT<br>GAACTCCAAGCTTATTCCAAGTACTATGGGCTTTAGGCCGTAATTCTGTAAGCAAAATAAAGCCCAAATAATCTTTTGA<br>TTTTTCTTTTTTTCTTTTTCCTGATCGTCTTGTG |
| OPH03 | 591 | NO. 226 | TCCACTCCTAGTTCACAATCTATTTTTTTCTTTTAAAAACATAGTAAACATACAATATAACTAATAGTATTTTATACGT<br>ACTATCATATAAATAATCACATATATTATATTTCAAATTTAATGTGAAGTACAAACACTTGTTACAATTTTGTTTGA<br>AAGATTTTATTTGTATATTAGAAGAAACTTGTTACAATATCCTTCTTTAAAAAAATCATGTGCAATTTTTTAAAAAAAT<br>ATGGTTAAAGATTGGAGCTGGTTAAAGATGGTTAGACAGAAGATAAATACTCTTTAACCATAACACAACCCATTAAAAT<br>GTTGAAAAAAAGAAAGGTATAGGGCTTTAATAATGAAAGATCCGTGAGATGCAAGATTAATATATAATCCAAACTCAAT<br>GTTTAATACCAGTGGCATTCTGATGTAAATAATGAGAAAAATTTAGGGTTATTTCTCATTTGCACTTCACTTTTAATAG<br>GATAGATAAGACCATGCTTTAAAAAATTGTTAGTAGTGTAGACAGATATGGTGTTTGTTAGATATATCGATCAATTTCA<br>GATGTTTTTGTCCCTTGTGTATTCCAACATTTTGTATA |
| RME01 | 454 | NO. 227 | TCCATTGCAGAATTCACCTGCGGAATGTAATTTCCTTCACCTAGTCGTCCACCTGCAACACAATCCGCAAGGGTGTGTT<br>GTAGCTTCTCCATTCCTTGAGATAAAGCGTCTTCAGCTTGCTGGCAAGATTGTCTTAGATTGCATACATCTAGAATCTG<br>CTGATCCGTCATGACATCAAAATGTGGCAAAAGAACCTGCAAAACAAAGATTTAAAAACATTGTATTAGATACAACGTT<br>CCAAGTCAAAAGTTAGAAGAGATCTTAAATAATATATAAAGAGAACGGCCTATAAGATTGATTTTTAGGTTAACACATT<br>ATTTTAGTTGTGTTTATTTTGATTGTTCTTTGTTACTTGTTTTCTACCTTGATAAGATCCGAGGGTCGAAAGCCGCCAA<br>TCCATATGAAAAAACGTTCTGCAGAAGTTCTCCACATTCCCGACATGACGAAGAAAACA |
| RME02 | 233 | NO. 228 | CTTGAGGGAAGGAGACGAGATGAGAGTCGTCATCAAAGATTCTACAGTGAAGAAGAAGAAGAAGATATTTTCGTCTCTT<br>GCTAACGGAGAAAGAGAGAGTGAAGTGAAGTGTGTGATATATCACGTGATCATCACGTGTGTTGATATCTTCGTCAATG<br>GCGCCATTTTTCAAGGCCGTATTTTGGGCTTTTAGTGATGGCCCCCAAATTTTTAAAAAAACCCATGACCCAAAAT |
| RME03 | 533 | NO. 229 | ATATCCTTAAACCCTTGCGCAATCTTCTGATCTTCTCCCACTGGCCTTTTAGCCTTCGCCTTTGCAGCTTTAACACCAA<br>CAGGCCTTTCCATAGCGTCATCATCCCCATTAACACTTGGCATAGAGCCTGATGCCTGAAAAGATTGTTCTTCCCCCAC<br>CCTCTTTCTTTTCGAACCTGAGCTTTGTTGACTAGTTCCTTGAGTCCCACACCATTTCTGATCATTCCTAAGCTCTCTC<br>CACGCATGTTCCAATGAGAACTTCACATTGTAATCGCTGAAGAATATTGCATATGCTGCTTTCAAGACGTCATCTTCAT<br>TCTGCCCACTGCTCCTCTGTTTTGTGGCAGCTTCAAATGACCCCACAAACTAGCAGACTCCTTCATTTATCTTCCCCCA<br>CCTTTGCTTACAGTGGGTCAGCTCTCTTGGAGGCAAACCAACCACCTTTGGACTTGCGTTGTAGTAAGCCGTGATCCTC<br>TTCCAAAAGGTTCCTGCTTTTTGCTCATTTCCAACGAGTGGGTCCTTGGAGGTATTCAA |
| RME04 | 699 | NO. 230 | GGTCTCAGGTTTTGTGGGAGTAATATCGGTTACCTCTTTTCCTATTACTTTGTCCTGTATAGAAAAATACTCATACCCA<br>TTATCATTTCCCTTGCGTAGAACTATATTTTATATAAATAGTTCTATTTTTTTTTTTAAATGAGTCGTTGAAACTTAGAA<br>CGCAAGAAAAGCTTTTATCTTTTGATCATGTCCTAATTCATAAGAAGATATCATTTATTTTTATAAAATATCAAGTTAT<br>ATCTAACGATTCTTAAACATGGTCGAATGTTCAGAAATAAAAATGAAGTCTTTCCAATAATAAATAAAATCTCTTCTAA<br>AAATATTTATTTTCAAAACAAACATGTTTATGTTTTTTTTTTTTTGTTTTTTGTTTTTTTTTGAGAATTCAAAACAGCCA<br>TGTTCTGATTGTATAACCCACTTACGTACAAACATTTAAATGATTTACGTACAGATAAATGTGGAAAACGTTACCTCGT<br>GAAACAAGGGACTGAGAGATTGGCTTTTGCCGTGTTCCTTCTTCACATCATCTTCAACCAGAATCTCTTTTCCTTTCTC<br>GCTCCGTCGTGCCGTAAGCAGCTGTATCAACCGCCTCGTTAGGAGCATTGCTCTGGCTCTTTTCCGCCGTAATCTTGTT<br>ATGATCACTCGGAGCCGCCATATCTCTCTCAACCGGAACCATATCCTCCTCGGAATCTTTGAGAACC |

TABLE 1b-continued

| Rf Marker Sequences | | | |
|---|---|---|---|
| Marker | Size | SEQ ID | Sequence (5' -> 3') |
| RME05 | 477 | NO. 231 | CTTGGTCACACCCATCTTCTCTCTGCGTAAATGTTATGCAGAGTTTGCAAAAGCATTTGTCCCTTGGTGTGAGAATCCT<br>CTGTGTGCTCTAAATGGACCCGGTTCGAATATATTCGATACTATCCATAAACACATCACAAACCAAGTAAGTTCTTTTC<br>TTCTAATGGGCTGATGATGTCCATTTAGTTTCCGTCCATTTTCCGATTTAACTTTAACGTAACGTTTATATGTCCATGC<br>ATAAGGACAATTAAGATACAAAGATAAATGAATCAGCCAATATGGAAATATAATTATTTATTTCCCTTGTTGTGTAATA<br>TCCCCTGCTTGATTCAGTATCAAAAACATTGAATATGCTTCCAAATAAATATATTTGAATATATATTCTACTACAAAAC<br>ATATCAATTTACGTCGTCTTAGGAAACCCTTATTTAATCAAATCTTTGTCTCTCTTTCTGGCCGCAGAGAGTTTATCGG<br>ACA |
| RME06 | 480 | NO. 232 | ATCAACCACGTTCATCCATGGATTTCTGGAAAAGGTATCAAATAAGAGGAAGAAGAAGATGGAGAAAAAGGGCATCAAG<br>TTAAGAAAACAAGTTTTTTTTGTTCGAATTGAACGTTTGATTAAATCTACAAACTAAGTGGATCTAAGAAGAAGTGCCC<br>AAGAAGAAGAACAAGGAGATCGAGTAGCAGAGAACAAGCTACAAAGAAGTGAGAAGAAGAAGAAGAGACTTGAGCCACA<br>AGAAACAAAAAAGTGAAGAAGAAAGGTGAGTGTGAGAACAAAAACAGAGTAAGTGAGTAACCAAGAACAAAGAGAGTAA<br>CAGAGAATAAGCTACAAAGAAGTGAGAAGAAGAAGATACTTGAGCCACGAGAAACAGAAAAGTGAAGAAGAAGTGTGAA<br>TGTGAGAACAAAAACAGAGAGTAAGTGAGTGAACAAGAGAAACAAAGATGATGGAGAGGCTGGGCTGGCCGAGAGTATT<br>TGAGTT |
| RME07 | 579 | NO. 233 | ATTTACCAAATGGATCACTCTGGATATTTGGGTTAGAATTTAATTTTAAATTTGTTAATGGGACATTATGTCAATTAAC<br>TTATTTAGTTAATTTTATTCTTGATAAACCCAAACAAAATATATTAAAATTTGGTGACTTGGTCAAAGTCACAATATTA<br>CTTTGCAAACTAACCTTCAAGATCAAGGAAATCAATTCCATAATTAGAATTGATATGTACGTTAGTTGACTCCTTTAAT<br>TTGCATAACGTGTACTTTCTCTTCAAGTTATAAAAAGAGATCACTTGTGCAGTTTTCTACGCACGGAGAAATAACAATT<br>CTCCATATTTCTTTTTTCTTTTGATTTGTTATTTTGAGTCTGAGAGTATACACAAAACTAGTTTCGTCGGGCTTCTGAT<br>AGAGTGACGCAAATCAGAATATTTTTTGCATTTGTATCTTGGGACTCATTACGTTATTGAACCGTCGCACTACGAGCGT<br>ATTTTGAATTAAAGAAAGAGATCTCGCCTCTGTAGTTGAATCATCATTTTCTTAATCTTTGGTATAATCTTATCAAATT<br>TATTCTTTACAATGTTCAATTCTCGG |
| RME08 | 496 | NO. 234 | CAATTCCACAACGTAGCAGAGCTTTGAAACGGAATAGATATCTGACTTTTCTAAAATTTGGTCAGATTGAACCAAATAT<br>TACACATGTGAAATTCGGTAATTAGTTAATATTTAAGAACTAAAAGTCGAGAGAAAGAGGCAGGCGGAAACGAGAGGTG<br>GGAAGGATTGGATACTTCCACGCAAAAGGGTATCTTCTTTTTTTTCCTCCTCGGATACTTCCGATCATGTTATTAATTT<br>GAGGTTCTTAATTTTTGATTTGACAGTTTTTTTTGTTTTAATTAAACTAAGAACCGACAGTTTTTTTTGTTTTTTTTT<br>CATAATTAGTAAAGGGTTCTTTGGGTGGAGTTCTTACCGAAATATAAGACTATGATTAATCCGGGTTTTTAGGCTGGGG<br>TTCTTAGCTTTGGTTAAGAACCATTTCTTAGCTTTTAACTAAAAAAAACTAAAAACCTGCTCTCAAAAAATAGATATAA<br>GAGCCGGTTCTTAGTCGAAAAG |
| RME09 | 574 | NO. 235 | AGCTTGGACTATGCCGTTTGCGTTCTGTACAAGAGAGAAGAAATGGTGTGAGTTTGCAGAGCCTGTTGATGGCGAATCA<br>ACAAAGTTTCTTCAAGAACTAGCCAAGAATTATAACATGGTGATTGTGAATCCTATCCTCGAAAGAGATATGGATCACG<br>GTGAAGTACTTTGGAACACAGCTGTGATTATAGGGAACAATGGAAACATCATTGGCAAACATAGGAAGGTTAACTTGCA<br>CTACAAGTCTCTTTTTGCTTCTGTCTTTTCTCTTGTGAGCTAACTTGTACTTCTTGGTTTGCTAGAACCACATACCGAG<br>GGTGGGAGATTTTAACGAGAGCACGTATTACATGGAAGGAGACACTGGACATCCTGTGTTTGAGACGGTGTTTGGGAAA<br>ATTGCAGTCAATATATGTTATGGAAGACACCATCCTCTAAACTGGTTAGCTTTTGGTCTAAATGGTGCTGAGATTGTCT<br>TCAACCCTTCAGCTACTGTTGGTGAACTCAGTGAACCAATGTGGCCTATTGAGGTTTAACTCCTAACTCCCCATTTTTC<br>ACACATAGCCGGTCCTGAAAT |
| RME10 | 570 | NO. 236 | TCGAGAATCCTCTACAAACGCACACCTTGGACATGCTCAGAACGGATATTAAAATCGACAAAACCGCCGCACCAGTCAT<br>GAACTGGCATTGGTTTCTTTGTGTCTTCCCCATTTTTAACAGCGGAAACACACCTCATGAACATGTTACGATTCACTCT<br>GCTGTGTACAAGCAGAGCTCGTAAACCTGTCCTCGCAGCTAGTTGACTCATGACTCGATACACACACTCGTTTCAGATC<br>ATATGGTCTAATGGATTTGGATATTATTCACTTCTCGGTAAGTCTTGCAGATGTTAGGAGAAAGGAGAAAATGTGACAG<br>CAGCTGTGTTCGCGGCAAGTGCTGCTAAGTACACGTGGTTCGAGTCTAACCGTTGTTTCATACTAAAAATATTTCTTCT<br>AACGGTCGTGATTTGATCATTTGAGTAGTGCAAGCAAGCGTAGGTGAATACACTAACCAGGGTGCTTAAGTGGGGTGCT<br>TAATAATTTTTGGATTTAAAACAAAAAAAAATATCCTAAAAAATAAAAAATGCTACTTGAGGGGTACTTAATTAAGCTG<br>TCGAATAAGTGGTGCTT |
| IN10 RS4 | 288 | NO. 237 | CAGAACACAGTTCTATGACACTGTCGATAGTAACATCCTCTGCAAGTACCAAAGAGATAGCAAATGAAACTATGTAAAC<br>AAATCAAAATTCTAAATTTCTCCATCACAAGGACCTACAGAATAGAGTTATCATAACATTTTCTGTAAATATTTCCATC<br>AAAATGACTAGAGAACAGAGTTCTTATAACATTATCTGTAAATGTTCCAACAAAACCACTACATAGCAGAGTTCTTATA<br>ACATTGTCTGTAAATGTCCAATCAAAACCACTACAGAACAAAGCTCCTATA |

TABLE 5

| Summary of Pedigree Leading to SRF Lines | | | | | | |
|---|---|---|---|---|---|---|
| Line | Gnrtn | Pedigree | Genotype | Phtp | Female | Genotype |
| 01SM001 | M1F1 | M143/96DHS60 | Rf^1rf/rfrf | S | SNH09984-M143 | Rf^1rf |
| 01SM002 | M1F1 | M336/96DHS60 | Rf^2rf/rfrf | S | SNH09984-M336 | Rf^2rf |
| 01SM005 | M1F1 | M662/96DHS60 | Rf^5rf/rfrf | S | SNH09984-M662 | Rf^5rf |
| 02SM008 | M2F1 | 01SM001-23/NS4302MC | Rf^1Rf/rfRf | F | 01SM0001-23 | Rf^1rf |
| 02SM009 | M2F1 | 01SM002-15/NS4302MC | Rf^2Rf/rfRf | F | 01SM0002-15 | Rf^2rf |
| 02SM011 | M2F1 | 01SM005-02/NS4302MC | Rf^5Rf/rfRf | F | 01SM0005-02 | Rf^5rf |
| 02SM086 | M3F1 | 96DHS60/02SM020)X | Rf^1rf/rfRf | F | 96DHS60 | rfrf |
| 02SM087 | M3F1 | 96DHS60/02SM024)X | Rf^2rf/rfRf | F | 96DHS60 | rfrf |
| 02SM088 | M3F1 | 96DHS60/02SM034)X | Rf^5rf/rfRf | F | 96DHS60 | rfrf |
| 03SM104 | M3F2 | 02SM086)A6 | rfrf/Rf^1rf/Rf^1Rf^1 | F | 02SM086-16 | Rf^1rf |

TABLE 5-continued

Summary of Pedigree Leading to SRF Lines

| | | | | | | |
|---|---|---|---|---|---|---|
| 03SM113 | M3F2 | 02SM087)7 | rfrf/Rf^2rf/Rf^2Rf^2 | F | 02SM087-07 | Rf^2rf |
| 03SM118 | M3F2 | 02SM088)9 | rfrf/Rf^5rf/Rf^5Rf^5 | F | 02SM088-09 | Rf^5rf |
| 04SM140 | M4F1 | NS4304MC/03SM104)X | Rf^1Rf | F | NS4304MC | RfRf |
| 04SM141 | M4F1 | NS4304MC/03SM113)X | Rf^2Rf | F | NS4304MC | RfRf |
| 04SM142 | M4F1 | NS4304MC/03SM118)X | Rf^5Rf | F | NS4304MC | RfRf |
| 04SM166 | M5F1 | NS2173FC/04SM140)X | rfRf^1/rfRf/rfRf* | S/F | NS2173FC | rfrf |
| 04SM167 | M5F1 | NS2173FC/04SM141)X | rfRf^2/rfRf/rfRf* | S/F | NS2173FC | rfrf |
| 04SM168 | M5F1 | NS2173FC/04SM142)X | rfRf^5/rfRf/rfRf* | S/F | NS2173FC | rfrf |
| 05SM194 | M6F2 | 04SM166)1439 | rfrf/rfRf$^{1439}$/Rf$^{1439}$Rf$^{1439}$ | S/F | 04SM166-1439 | rfRf$^{1439}$ |
| 05SM197 | M6F2 | 04SM166)1815 | rfrf/rfRf$^{1815}$/Rf$^{1815}$Rf$^{1815}$ | S/F | 04SM166-1815 | rfRf$^{1815}$ |
| 05SM198 | M6F2 | 04SM166)1931 | rfrf/rfRf$^{1931}$/Rf$^{1931}$Rf$^{1931}$ | S/F | 04SM166-1931 | rfRf$^{1931}$ |
| 05SM205 | M7BC0 | 04SM166-1439/NS1822BC | rfrf/rfRf$^{1439}$ | S/F | NS1822FC | rfrf |
| 05SM208 | M7BC0 | 04SM166-1815/NS1822BC | rfrf/rfRf$^{1815}$ | S/F | NS1822FC | rfrf |
| 05SM209 | M7BC0 | 04SM166-1931/NS1822BC | rfrf/rfRf$^{1931}$ | S/F | NS1822FC | rfrf |
| 05SM234 | M8BC1 | NS1822FC/05SM205)X | rfrf/rfRf$^{1439}$ | S/F | NS1822FC | rfrf |
| 05SM235 | M8BC1 | NS1822FC/05SM208)X | rfrf/rfRf$^{1815}$ | S/F | NS1822FC | rfrf |
| 05SM236 | M8BC1 | NS1822FC/05SM209)X | rfrf/rfRf$^{1931}$ | S/F | NS1822FC | rfrf |
| 06SM330 | M9BC2 | NS1822FC/05SM234)X | rfrf/rfRf$^{1439}$ | S/F | NS1822FC | rfrf |
| 06SM331 | M9BC2 | NS1822FC/05SM235)X | rfrf/rfRf$^{1815}$ | S/F | NS1822FC | rfrf |
| 06SM332 | M9BC2 | NS1822FC/05SM236)X | rfrf/rfRf$^{1931}$ | S/F | NS1822FC | rfrf |
| 06SM341 | M6DHS1 | (05SM194DH)1 | Rf$^{1439}$Rf$^{1439}$ | F | 05SM194DH1 | Rf$^{1439}$Rf$^{1439}$ |
| 06SM350 | M6DHS1 | (05SM197DH)i7 | Rf$^{1815}$Rf$^{1815}$ | F | 05SM197DH97 | Rf$^{1815}$Rf$^{1815}$ |
| 06SM351 | M6DHS1 | (05SM198DH)1 | Rf$^{1931}$Rf$^{1931}$ | F | 05SM198DH1 | Rf$^{1931}$Rf$^{1931}$ |
| 06SM399 | M10BC3 | NS1822FC/06SM330)X | rfrf/rfRf$^{1439}$ | S/F | NS1822FC | rfrf |
| 06SM400 | M10BC3 | NS1822FC/06SM331)X | rfrf/rfRf$^{1815}$ | S/F | NS1822FC | rfrf |
| 06SM401 | M10BC3 | NS1822FC/06SM332)X | rfrf/rfRf$^{1931}$ | S/F | NS1822FC | rfrf |
| 06SM403 | BC2S1 | 06SM330)X | rfrf/rfRf$^{1439}$/Rf$^{1439}$Rf$^{1439}$ | S/F | 06SM330blk | rfRf$^{1439}$ |
| 06SM404 | BC2S1 | 06SM331)X | rfrf/rfRf$^{1815}$/Rf$^{1815}$Rf$^{1815}$ | S/F | 06SM331blk | rfRf$^{1815}$ |
| 06SM405 | BC2S1 | 06SM332)X | rfrf/rfRf$^{1931}$/Rf$^{1931}$Rf$^{1931}$ | S/F | 06SM332blk | rfRf$^{1931}$ |
| 06SM408 | M6DHS2 | 06SM342)1 | Rf$^{1439}$Rf$^{1439}$ | F | 06SM342-1 | Rf$^{1439}$Rf$^{1439}$ |
| 06SM410 | M6DHS2 | 06SM350)1 | Rf$^{1815}$Rf$^{1815}$ | F | 06SM350-1 | Rf$^{1815}$Rf$^{1815}$ |
| 06SM412 | M6DHS2 | 06SM354)1 | Rf$^{1931}$Rf$^{1931}$ | F | 06SM354-1 | Rf$^{1931}$Rf$^{1931}$ |
| 06SM414 | M11BC4 | NS1822FC/06SM399)X | rfrf/rfRf$^{1439}$ | S/F | NS1822FC | rfrf |
| 06SM415 | M11BC4 | NS1822FC/06SM400)X | rfrf/rfRf$^{1815}$ | S/F | NS1822FC | rfrf |
| 06SM416 | M11BC4 | NS1822FC/06SM401)X | rfrf/rfRf$^{1931}$ | S/F | NS1822FC | rfrf |
| 06SM420 | BC2S2 | 06SM403)3 | Rf$^{1439}$Rf$^{1439}$ | F | 06SM403-3 | Rf$^{1439}$Rf$^{1439}$ |
| 06SM426 | BC2S2 | 06SM404)2 | Rf$^{1815}$Rf$^{1815}$ | F | 06SM404-2 | Rf$^{1815}$Rf$^{1815}$ |
| 06SM432 | BC2S2 | 06SM405)7 | Rf$^{1931}$Rf$^{1931}$ | F | 06SM405-7 | Rf$^{1931}$Rf$^{1931}$ |
| 06SM438 | BC4S1 | 06SM414)X | rfrf/rfRf$^{1439}$/Rf$^{1439}$Rf$^{1439}$ | S/F | 06SM414blk | rfRf$^{1439}$ |
| 06SM439 | BC4S1 | 06SM415)X | rfrf/rfRf$^{1815}$/Rf$^{1815}$Rf$^{1815}$ | S/F | 06SM415blk | rfRf$^{1815}$ |
| 06SM440 | BC4S1 | 06SM416)X | rfrf/rfRf$^{1931}$/Rf$^{1931}$Rf$^{1931}$ | S/F | 06SM416blk | rfRf$^{1931}$ |
| 07SM441 | BC4S2 | 06SM438)X | Rf$^{1439}$Rf$^{1439}$ | F | 06SM438blk | Rf$^{1439}$Rf$^{1439}$ |
| 07SM442 | BC4S2 | 06SM439)X | Rf$^{1815}$Rf$^{1815}$ | F | 06SM439blk | Rf$^{1815}$Rf$^{1815}$ |
| 07SM443 | BC4S2 | 06SM440)X | Rf$^{1931}$Rf$^{1931}$ | F | 06SM440blk | Rf$^{1931}$Rf$^{1931}$ |

| | | | Marker | | | | |
|---|---|---|---|---|---|---|---|
| Line | Male | Genotype | Y5N | OPC2 | RMB12 | RMA07 | CMS |
| 01SM001 | 96DHS60 | rfrf | + | ± | − | − | + |
| 01SM002 | 96DHS60 | rfrf | + | ± | − | ± | + |
| 01SM005 | 96DHS60 | rfrf | + | − | − | ± | + |
| 02SM008 | NS4302MC | RfRf | ± | + | + | + | + |
| 02SM009 | NS4302MC | RfRf | ± | + | + | + | + |
| 02SM011 | NS4302MC | RfRf | ± | + | + | + | + |
| 02SM086 | 02SM008-6 | Rf^1Rf | + | + | ± | ± | − |
| 02SM087 | 02SM009-6 | Rf^2Rf | + | + | ± | + | − |
| 02SM088 | 02SM011-7 | Rf^5Rf | + | ± | ± | + | − |
| 03SM104 | 02SM086-16 | Rf^1rf | ± | + | − | − | − |
| 03SM113 | 02SM087-07 | Rf^2rf | ± | + | − | + | − |
| 03SM118 | 02SM088-09 | Rf^5rf | ± | − | − | + | − |
| 04SM140 | 03SM104blk | Rf^1Rf^1 | − | + | + | + | + |
| 04SM141 | 03SM113blk | Rf^2Rf^2 | − | + | + | + | + |
| 04SM142 | 03SM118blk | Rf^5Rf^5 | − | + | + | + | + |
| 04SM166 | 04SM140blk | Rf^1Rf | + | + | ± | ± | + |
| 04SM167 | 04SM141blk | Rf^2Rf | + | + | ± | + | + |
| 04SM168 | 04SM142blk | Rf^5Rf | + | ± | ± | + | + |
| 05SM194 | 04SM166-1439 | rfRf$^{1439}$ | ± | − | ± | − | + |
| 05SM197 | 04SM166-1815 | rfRf$^{1815}$ | ± | − | ± | − | + |
| 05SM198 | 04SM166-1931 | rfRf$^{1931}$ | ± | − | ± | − | + |
| 05SM205 | 04SM166-1439 | rfRf$^{1439}$ | ± | − | ± | − | + |
| 05SM208 | 04SM166-1815 | rfRf$^{1815}$ | ± | − | ± | − | + |
| 05SM209 | 04SM166-1931 | rfRf$^{1931}$ | ± | − | ± | − | + |
| 05SM234 | 05SM205blk | rfRf$^{1439}$ | ± | − | ± | − | + |
| 05SM235 | 05SM208blk | rfRf$^{1815}$ | ± | − | ± | − | + |
| 05SM236 | 05SM209blk | rfRf$^{1931}$ | ± | − | ± | − | + |
| 06SM330 | 05SM234blk | rfRf$^{1439}$ | ± | − | ± | − | + |
| 06SM331 | 05SM235blk | rfRf$^{1815}$ | ± | − | ± | − | + |

TABLE 5-continued

Summary of Pedigree Leading to SRF Lines

| | | | | | | | |
|---|---|---|---|---|---|---|---|
| 06SM332 | 05SM236blk | $rfRf^{1931}$ | ± | − | ± | − | + |
| 06SM341 | 05SM194DH1 | $Rf^{1439}Rf^{1439}$ | − | − | + | − | + |
| 06SM350 | 05SM197DH97 | $Rf^{1815}Rf^{1815}$ | − | − | + | − | + |
| 06SM351 | 05SM198DH1 | $Rf^{1931}Rf^{1931}$ | − | − | + | − | + |
| 06SM399 | 06SM330blk | $rfRf^{1439}$ | ± | − | ± | − | + |
| 06SM400 | 06SM331blk | $rfRf^{1815}$ | ± | − | ± | − | + |
| 06SM401 | 06SM332blk | $rfRf^{1931}$ | ± | − | ± | − | + |
| 06SM403 | 06SM330blk | $rfRf^{1439}$ | ± | − | ± | − | + |
| 06SM404 | 06SM331blk | $rfRf^{1815}$ | ± | − | ± | − | + |
| 06SM405 | 06SM332blk | $rfRf^{1931}$ | ± | − | ± | − | + |
| 06SM408 | 06SM342-1 | $Rf^{1439}Rf^{1439}$ | − | − | + | − | + |
| 06SM410 | 06SM350-1 | $Rf^{1815}Rf^{1815}$ | − | − | + | − | + |
| 06SM412 | 06SM354-1 | $Rf^{1931}Rf^{1931}$ | − | − | + | − | + |
| 06SM414 | 06SM399blk | $rfRf^{1439}$ | ± | − | ± | − | + |
| 06SM415 | 06SM400blk | $rfRf^{1815}$ | ± | − | ± | − | + |
| 06SM416 | 06SM401blk | $rfRf^{1931}$ | ± | − | ± | − | + |
| 06SM420 | 06SM403-3 | $Rf^{1439}Rf^{1439}$ | − | − | + | − | + |
| 06SM426 | 06SM404-2 | $Rf^{1815}Rf^{1815}$ | − | − | + | − | + |
| 06SM432 | 06SM405-7 | $Rf^{1931}Rf^{1931}$ | − | − | + | − | + |
| 06SM438 | 06SM414blk | $rfRf^{1439}$ | ± | − | ± | − | + |
| 06SM439 | 06SM415blk | $rfRf^{1815}$ | ± | − | ± | − | + |
| 06SM440 | 06SM416blk | $rfRf^{1931}$ | ± | − | ± | − | + |
| 07SM441 | 06SM438blk | $Rf^{1439}Rf^{1439}$ | − | − | + | − | + |
| 07SM442 | 06SM439blk | $Rf^{1815}Rf^{1815}$ | − | − | + | − | + |
| 07SM443 | 06SM440blk | $Rf^{1931}Rf^{1931}$ | − | − | + | − | + |

What is claimed is:

1. A *Brassica* plant comprising a fertility gene for *Ogura* cytoplasmic male sterility, wherein the fertility gene is on a *Raphanus* fragment introgressed from *Raphanus sativa*, and the *Raphanus* fragment lacks markers RMA01, RMA02, RMA03, RMA04, RMA05, RMA06, RMA07, RMA08, RMA09, RMA10, RMC24, OPC2, RMC25, RMC26, RMC27, RMC28, RMC29, RMC30, RMC31, RMC32 and RMC33; and wherein said *Raphanus* fragment comprises a molecular marker selected from the group consisting of RMB01, E35M62, RMB02, RMB03, RMB04, RMB05, RMB06, RMB07, RMB08, RMB09, RMB10, OPF10, RMB11, RMB12, RMC01, RMC02, RMC03, E38M60, RMC04, RMC05, RMC06, RMC07, RMC08, RMC17, RMC18, RMC19, RMC20, RMC21, RMC22 and RMC23.

2. The *Brassica* plant of claim 1 designated R1439, representative seed of which have been deposited under NCIMB Accession Number 41510, or an F1 progeny produced by crossing R1439 with a second plant.

3. A progeny or descendent plant of the *Brassica* plant of claim 2, wherein the progeny or descendent plant comprises a *Raphanus* fragment which lacks markers RMA01, RMA02, RMA03, RMA04, RMA05, RMA06, RMA07, RMA08, RMA09, RMA10, RMC09, RMC10, RMC11, RMC12, RMC13, RMC14, RMC15, RMC16, RMC24, OPC2, RMC25, RMC26, RMC27, RMC28, RMC29, RMC30, RMC31, RMC32 and RMC33; and wherein said *Raphanus* fragment comprises a molecular marker selected from the group consisting of RMB01, E35M62, RMB02, RMB03, RMB04, RMB05, RMB06, RMB07, RMB08, RMB09, RMB10, OPF10, RMB11, RMB12, RMC01, RMC02, RMC03, E38M60, RMC04, RMC05, RMC06, RMC07, RMC08, RMC17, RMC18, RMC19, RMC20, RMC21, RMC22 and RMC23.

4. A plant cell from the *Brassica* plant of claim 1.

5. A part of the *Brassica* plant of claim 1.

6. A *Brassica* plant comprising the recombination event of R1439, the recombination event comprising a shortened *Raphanus* fragment comprising the fertility restorer gene for *Ogura* cytoplasmic male sterility and having about 51% marker loss as compared to first phase recombinant restorer material NW1717.

* * * * *